(12) United States Patent
Xu et al.

(10) Patent No.: US 11,225,522 B2
(45) Date of Patent: Jan. 18, 2022

(54) SINGLE DOMAIN ANTIBODY AND DERIVATIVE PROTEINS THEREOF AGAINST PROGRAMMED DEATH-LIGAND (PDL1)

(71) Applicant: Suzhou Alphamab Co., LTD., Jiangsu (CN)

(72) Inventors: Ting Xu, Jiangsu (CN); Yanrong Dong, Jiangsu (CN); Pilin Wang, Jiangsu (CN); Ting Chen, Jiangsu (CN)

(73) Assignee: Suzhou Alphamab Co., LTD., Jiangsu (CN)

( * ) Notice: Subject to any disclaimer, the term of this patent is extended or adjusted under 35 U.S.C. 154(b) by 0 days.

(21) Appl. No.: 15/748,421

(22) PCT Filed: Aug. 1, 2016

(86) PCT No.: PCT/CN2016/092679
§ 371 (c)(1),
(2) Date: Jan. 29, 2018

(87) PCT Pub. No.: WO2017/020801
PCT Pub. Date: Feb. 9, 2017

(65) Prior Publication Data
US 2018/0327494 A1    Nov. 15, 2018

(30) Foreign Application Priority Data

Jul. 31, 2015    (CN) .......................... 201510465481.8

(51) Int. Cl.
| *C07K 16/28* | (2006.01) |
| *A61K 39/395* | (2006.01) |
| *C12N 5/10* | (2006.01) |
| *C12N 15/85* | (2006.01) |
| *A61P 35/00* | (2006.01) |
| *A61K 45/06* | (2006.01) |
| *C07K 16/30* | (2006.01) |
| *A61K 47/68* | (2017.01) |
| *G01N 33/574* | (2006.01) |
| *A61K 39/00* | (2006.01) |
| *A61N 5/10* | (2006.01) |

(52) U.S. Cl.
CPC ........ *C07K 16/2827* (2013.01); *A61K 39/395* (2013.01); *A61K 39/3955* (2013.01); *A61K 39/39558* (2013.01); *A61K 45/06* (2013.01); *A61K 47/6849* (2017.08); *A61P 35/00* (2018.01); *C07K 16/28* (2013.01); *C07K 16/30* (2013.01); *C12N 5/10* (2013.01); *C12N 15/85* (2013.01); *G01N 33/574* (2013.01); *A61K 2039/505* (2013.01); *A61K 2039/545* (2013.01); *A61N 5/10* (2013.01); *C07K 2317/24* (2013.01); *C07K 2317/30* (2013.01); *C07K 2317/52* (2013.01); *C07K 2317/565* (2013.01); *C07K 2317/569* (2013.01); *C07K 2317/72* (2013.01); *C07K 2317/732* (2013.01); *C07K 2317/734* (2013.01); *C07K 2317/76* (2013.01); *C07K 2317/92* (2013.01); *C07K 2317/94* (2013.01); *C07K 2319/30* (2013.01)

(58) Field of Classification Search
CPC ................ A61K 47/6849; C07K 16/28; C07K 2317/24; C07K 2317/565; C07K 2317/569
See application file for complete search history.

(56) References Cited

U.S. PATENT DOCUMENTS

| 2017/0029508 | A1* | 2/2017 | Eisenbach-Schwartz ................... C07K 16/2818 |
| 2018/0009893 | A1* | 1/2018 | Eisenbach-Schwartz ................... C07K 16/2827 |
| 2018/0291103 | A1* | 10/2018 | Xu ........................ A61K 45/06 |
| 2019/0016814 | A1* | 1/2019 | Humphrey ............ A61K 47/65 |
| 2019/0055236 | A1* | 2/2019 | Glick ................. A61K 31/5377 |
| 2019/0135825 | A1* | 5/2019 | Wiles ................... C07D 403/14 |
| 2019/0321370 | A1* | 10/2019 | Sorrentino ........... A61K 33/243 |
| 2019/0352404 | A1* | 11/2019 | Xu ........................ A61K 39/395 |
| 2020/0024358 | A1* | 1/2020 | Borras .................. C07K 16/30 |
| 2020/0062858 | A1* | 2/2020 | Borras .............. G01N 33/5011 |

FOREIGN PATENT DOCUMENTS

| CN | 102264762 A | 11/2011 |
| CN | 104479018 A | 4/2015 |
| JP | 2012504970 A | 3/2012 |
| JP | 2013511959 A | 4/2013 |
| JP | 2018529375 A | 10/2018 |
| WO | 2008071447 | 6/2008 |
| WO | 2010077634 | 7/2010 |
| WO | 2011066389 | 6/2011 |
| WO | 2017157334 | 9/2017 |
| WO | 2018170168 | * 9/2018 |

(Continued)

OTHER PUBLICATIONS

Luan et al. (International Immunopharmacology 31:248-256; Epub Jan. 12, 2016 (Feb. 2016)).*

(Continued)

*Primary Examiner* — Lynn A Bristol

(74) *Attorney, Agent, or Firm* — Schwegman Lundberg & Woessner, P.A.

(57) ABSTRACT

The present invention relates to the field of medical biology and discloses a single domain antibody and derivative proteins thereof against programmed death ligand (PDL1). In particular, the present invention discloses a programmed death ligand 1 (PDL1) binding molecule and the use thereof, especially the use for treating and/or preventing or diagnosing PDL1 relevant diseases such as tumor.

20 Claims, 20 Drawing Sheets
Specification includes a Sequence Listing.

(56) References Cited

FOREIGN PATENT DOCUMENTS

| WO | WO 2018/170168 | * | 9/2018 | ............. C07K 14/74 |
| WO | WO 2018223002 A1 | * | 12/2018 | |
| WO | WO 2018223004 A1 | * | 12/2018 | |
| WO | WO 2019/047885 | * | 3/2019 | ............. C07K 16/46 |
| WO | WO 2020/089722 | * | 5/2020 | ............. A16K 45/06 |

OTHER PUBLICATIONS

Tang et al. (CancerCell. 29(3):285-296 (Mar. 14, 2016)).*
Zhang et al. (Cell Discov. 3:17004 (Mar. 7, 2017)).*
Li et al., (Mol Pharm. 15(4): 1674-1681 (Apr. 2, 2018)).*
Li et al., (Mol Pharm. 16(8):3469-3476 (Aug. 5, 2019)).*
"International Application No. PCT/CN2016/092679, International Search Report dated Nov. 08, 2016", w/ English Translation, (Nov. 8, 2016), 12 pgs.
"International Application No. PCT/CN2016/092679, Written Opinion dated Nov. 8, 2016", (Nov. 8, 2016), 5 pgs.
"European Application Serial No. 16832289.9 Search Report dated Mar. 27, 2019", 20 pgs.
Lecocq, Quentin, "Nanobody-mediated imaging and inhibition of the immune checkpoint ligand PD-L1", XP05553650, (Jan. 2, 2016), 53 pgs.
Strohl, William R, "Optimization of Fc-mediated effector functions of monoclonal antibodies", Science Direct current Opinion in Biotechnology vol. 20, No. 6, (2009), 8 pgs.
Zhang, Fei, "Structural basis of a novel PD-L1 nanobody for immune checkpoint blockade", Cell Discovery 3, 17004, (Mar. 7, 2017), 12 pgs.
"U.S. Appl. No. 15/748,438, Preliminary Amendment filed Jan. 29, 2018", 4 pgs.
"U.S. Appl. No. 15/748,438, Supplemental Preliminary Amendment filed Jun. 25, 2018", 7 pgs.
"U.S. Appl. No. 15/748,438, Final Office Action dated Oct. 20, 2020", 9 pgs.
"U.S. Appl. No. 15/748,438, Non Final Office Action dated May 18, 2020", 9 pgs.
"U.S. Appl. No. 15/748,438, Response filed Mar. 9, 2020 to Restriction Requirement dated Jan. 8, 2020", 9 pgs.
"U.S. Appl. No. 15/748,438, Response filed Sep. 2, 2020 to Non Final Office Action dated May 18, 2020", 8 pgs.
"U.S. Appl. No. 15/748,438, Restriction Requirement dated Jan. 8, 2020", 8 pgs.
"European Application Serial No. 16832290.7, Extended European Search Report dated Mar. 14, 2019", 12 pgs.
"International Application No. PCT/CN2016/092680, International Search Report dated Nov. 10, 2016", w/ English Translation, (Nov. 10, 2016), 12 pgs.
"International Application No. PCT/CN2016/092680, Written Opinion dated Nov. 10, 2016", (Nov. 10, 2016), 5 pgs.
"Japanese Application Serial No. 2018-524526, Office Action dated Nov. 7, 2019", w/English Translation, 12 pgs.
Ishiichi, et al., "Molecular Design of Antibody Pharmaceuticals", Pharmacology Medicine vol. 74, (2014), 4-11.
Ji, et al., "Covalently dimerized Camelidae antihuman TNFa single-domain antibodies expressed in yeast *Pichia pastoris* show superior neutralizing activity", AMB, 97, (2013), 8547-8558.
Kato, Yoshinori, et al., "A Depolymerize Antibody Fragment", Clinical Chemistry vol. 36, (2007), 16 pgs.
"Japanese Application Serial No. 2018-524525, Office Action dated Apr. 2, 2020", w/ English Translation, (Apr. 2, 2020), 13 pgs.

\* cited by examiner

SEQUENCE LISTING

<160> NUMBER OF SEQ ID NOS: 85

<210> SEQ ID NO 1
<211> LENGTH: 5
<212> TYPE: PRT
<213> ORGANISM: Artificial Sequence
<220> FEATURE:
<223> OTHER INFORMATION: A synthetic 10CDR1

<400> SEQUENCE: 1

Ser Tyr Cys Met Gly
1               5

<210> SEQ ID NO 2
<211> LENGTH: 16
<212> TYPE: PRT
<213> ORGANISM: Artificial Sequence
<220> FEATURE:
<223> OTHER INFORMATION: A synthetic 10CDR2

<400> SEQUENCE: 2

Ala Ile Asp Ser Asp Gly Thr Thr Lys Tyr Ala Asp Ser Met Lys Gly
1               5                   10                  15

<210> SEQ ID NO 3
<211> LENGTH: 16
<212> TYPE: PRT
<213> ORGANISM: Artificial Sequence
<220> FEATURE:
<223> OTHER INFORMATION: A synthetic 10CDR3

<400> SEQUENCE: 3

Arg Leu Asn Cys Pro Gly Pro Val Asp Trp Val Pro Met Phe Pro Tyr
1               5                   10                  15

<210> SEQ ID NO 4
<211> LENGTH: 5
<212> TYPE: PRT
<213> ORGANISM: Artificial Sequence
<220> FEATURE:
<223> OTHER INFORMATION: A synthetic 27CDR1

<400> SEQUENCE: 4

Arg Arg Cys Met Ala
1               5

<210> SEQ ID NO 5
<211> LENGTH: 17
<212> TYPE: PRT
<213> ORGANISM: Artificial Sequence
<220> FEATURE:
<223> OTHER INFORMATION: A synthetic 27CDR2

```
<400> SEQUENCE: 5

Asn Ile Leu Thr Thr Thr Gly Asn Thr Tyr Leu Ala Asp Ser Val Lys
1               5                   10                  15

Gly

<210> SEQ ID NO 6
<211> LENGTH: 19
<212> TYPE: PRT
<213> ORGANISM: Artificial Sequence
<220> FEATURE:
<223> OTHER INFORMATION: A synthetic 27CDR3

<400> SEQUENCE: 6

Asp Ser Phe His Asp Pro Thr Cys Thr Val Val Ala Ser Ser Gly Ala
1               5                   10                  15

Phe Gln Tyr

<210> SEQ ID NO 7
<211> LENGTH: 5
<212> TYPE: PRT
<213> ORGANISM: Artificial Sequence
<220> FEATURE:
<223> OTHER INFORMATION: A synthetic 38CDR1

<400> SEQUENCE: 7

Arg Arg Cys Met Gly
1               5

<210> SEQ ID NO 8
<211> LENGTH: 16
<212> TYPE: PRT
<213> ORGANISM: Artificial Sequence
<220> FEATURE:
<223> OTHER INFORMATION: A synthetic 38CDR2

<400> SEQUENCE: 8

Asn Ile Thr Gly Thr Gly Asn Thr Tyr Leu Ala Asp Ser Val Lys Gly
1               5                   10                  15

<210> SEQ ID NO 9
<211> LENGTH: 17
<212> TYPE: PRT
<213> ORGANISM: Artificial Sequence
<220> FEATURE:
<223> OTHER INFORMATION: A synthetic 38CDR3

<400> SEQUENCE: 9

Asp Ser Phe Pro Thr Cys Thr Val Val Ala Ser Ser Gly Ala Phe Gln
1               5                   10                  15

Tyr

<210> SEQ ID NO 10
<211> LENGTH: 5
<212> TYPE: PRT
<213> ORGANISM: Artificial Sequence
<220> FEATURE:
<223> OTHER INFORMATION: A synthetic 56CDR1

<400> SEQUENCE: 10

Arg Arg Cys Met Ala
1               5

<210> SEQ ID NO 11
```

```
<211> LENGTH: 17
<212> TYPE: PRT
<213> ORGANISM: Artificial Sequence
<220> FEATURE:
<223> OTHER INFORMATION: A synthetic 56CDR2

<400> SEQUENCE: 11

Lys Leu Leu Thr Thr Ser Gly Ser Thr Tyr Leu Ala Asp Ser Val Lys
1               5                   10                  15

Gly

<210> SEQ ID NO 12
<211> LENGTH: 19
<212> TYPE: PRT
<213> ORGANISM: Artificial Sequence
<220> FEATURE:
<223> OTHER INFORMATION: A synthetic 56CDR3

<400> SEQUENCE: 12

Asp Ser Phe Glu Asp Pro Thr Cys Thr Leu Val Thr Ser Ser Gly Ala
1               5                   10                  15

Phe Gln Tyr

<210> SEQ ID NO 13
<211> LENGTH: 5
<212> TYPE: PRT
<213> ORGANISM: Artificial Sequence
<220> FEATURE:
<223> OTHER INFORMATION: A synthetic 69CDR1

<400> SEQUENCE: 13

Ser Tyr Cys Met Ala
1               5

<210> SEQ ID NO 14
<211> LENGTH: 17
<212> TYPE: PRT
<213> ORGANISM: Artificial Sequence
<220> FEATURE:
<223> OTHER INFORMATION: A synthetic 69CDR2

<400> SEQUENCE: 14

Lys Ile Leu Thr Thr Pro Gly Asn Thr Tyr Leu Ala Asp Ser Val Lys
1               5                   10                  15

Gly

<210> SEQ ID NO 15
<211> LENGTH: 19
<212> TYPE: PRT
<213> ORGANISM: Artificial Sequence
<220> FEATURE:
<223> OTHER INFORMATION: A synthetic 69CDR3

<400> SEQUENCE: 15

Asp Ser Phe Gln Lys Pro Thr Cys Thr Val Val Ala Ser Trp Pro Ala
1               5                   10                  15

Phe Gln Tyr

<210> SEQ ID NO 16
<211> LENGTH: 5
<212> TYPE: PRT
<213> ORGANISM: Artificial Sequence
<220> FEATURE:
<223> OTHER INFORMATION: A synthetic 81CDR1
```

```
<400> SEQUENCE: 16

Val Arg Cys Met Ala
1               5

<210> SEQ ID NO 17
<211> LENGTH: 17
<212> TYPE: PRT
<213> ORGANISM: Artificial Sequence
<220> FEATURE:
<223> OTHER INFORMATION: A synthetic 81CDR2

<400> SEQUENCE: 17

Asn Ile Leu Thr Thr Thr Ile Ser Thr Tyr Leu Ala Asp Ser Val Lys
1               5                   10                  15

Gly

<210> SEQ ID NO 18
<211> LENGTH: 19
<212> TYPE: PRT
<213> ORGANISM: Artificial Sequence
<220> FEATURE:
<223> OTHER INFORMATION: A synthetic 81CDR3

<400> SEQUENCE: 18

Asp Ser Phe Gly Tyr Pro Thr Cys Pro Gly Pro Ala Ser Ser Gly Ala
1               5                   10                  15

Phe Gln Tyr

<210> SEQ ID NO 19
<211> LENGTH: 5
<212> TYPE: PRT
<213> ORGANISM: Artificial Sequence
<220> FEATURE:
<223> OTHER INFORMATION: A synthetic 87CDR1

<400> SEQUENCE: 19

Ser Cys Gly Met Gly
1               5

<210> SEQ ID NO 20
<211> LENGTH: 16
<212> TYPE: PRT
<213> ORGANISM: Artificial Sequence
<220> FEATURE:
<223> OTHER INFORMATION: A synthetic 87CDR2

<400> SEQUENCE: 20

Thr Ile Ser Ser Asp Gly Thr Thr Ser Tyr Ala Asp Ser Val Lys Gly
1               5                   10                  15

<210> SEQ ID NO 21
<211> LENGTH: 21
<212> TYPE: PRT
<213> ORGANISM: Artificial Sequence
<220> FEATURE:
<223> OTHER INFORMATION: A synthetic 87CDR3

<400> SEQUENCE: 21

Asp Cys Pro Pro Ile Pro Glu Phe Thr Ser Cys Ser Gly Gly Tyr Cys
1               5                   10                  15

Leu Ser Gly Asp Tyr
            20

<210> SEQ ID NO 22
```

```
<211> LENGTH: 5
<212> TYPE: PRT
<213> ORGANISM: Artificial Sequence
<220> FEATURE:
<223> OTHER INFORMATION: A synthetic 94CDR1

<400> SEQUENCE: 22

Ser Tyr Cys Met Gly
1               5

<210> SEQ ID NO 23
<211> LENGTH: 16
<212> TYPE: PRT
<213> ORGANISM: Artificial Sequence
<220> FEATURE:
<223> OTHER INFORMATION: A synthetic 94CDR2

<400> SEQUENCE: 23

Thr Ile Asp Ser Asp Gly Thr Thr Arg Tyr Val Asp Ser Val Lys Gly
1               5                   10                  15

<210> SEQ ID NO 24
<211> LENGTH: 16
<212> TYPE: PRT
<213> ORGANISM: Artificial Sequence
<220> FEATURE:
<223> OTHER INFORMATION: A synthetic 94CDR3

<400> SEQUENCE: 24

Arg Leu Asn Cys Pro Gly Pro Val Asp Trp Val Pro Met Phe Pro Tyr
1               5                   10                  15

<210> SEQ ID NO 25
<211> LENGTH: 124
<212> TYPE: PRT
<213> ORGANISM: Artificial Sequence
<220> FEATURE:
<223> OTHER INFORMATION: A synthetic antibody No.10

<400> SEQUENCE: 25

Gln Val Gln Leu Gln Glu Ser Gly Gly Gly Ser Val Gln Ala Gly Gly
1               5                   10                  15

Ser Leu Arg Leu Ser Cys Ala Ala Ser Gly Asn Ile Val Ser Ser Tyr
            20                  25                  30

Cys Met Gly Trp Phe Arg Gln Ala Pro Gly Lys Glu Arg Val Gly Val
        35                  40                  45

Ala Ala Ile Asp Ser Asp Gly Thr Thr Lys Tyr Ala Asp Ser Met Lys
    50                  55                  60

Gly Arg Phe Thr Ile Ser Lys Asp Asn Ala Lys Asn Thr Leu Asp Leu
65                  70                  75                  80

Gln Met Asn Ser Leu Lys Pro Glu Asp Thr Ala Met Tyr Tyr Cys Val
                85                  90                  95

Ala Arg Leu Asn Cys Pro Gly Pro Val Asp Trp Val Pro Met Phe Pro
            100                 105                 110

Tyr Arg Gly Gln Gly Thr Gln Val Thr Val Ser Ser
        115                 120

<210> SEQ ID NO 26
<211> LENGTH: 128
<212> TYPE: PRT
<213> ORGANISM: Artificial Sequence
<220> FEATURE:
<223> OTHER INFORMATION: A synthetic antibody No.27
```

```
<400> SEQUENCE: 26

Gln Val Gln Leu Gln Glu Ser Gly Gly Gly Ser Val Gln Ala Gly Gly
1               5                   10                  15

Ser Leu Arg Leu Ser Cys Ala Ala Ser Gly Asn Ile Ser Ser Arg Arg
            20                  25                  30

Cys Met Ala Trp Phe Arg Gln Ala Pro Gly Lys Glu Arg Glu Arg Val
        35                  40                  45

Ala Asn Ile Leu Thr Thr Thr Gly Asn Thr Tyr Leu Ala Asp Ser Val
    50                  55                  60

Lys Gly Arg Phe Thr Ile Ser Gln Asn Asn Ala Lys Ser Thr Val Tyr
65                  70                  75                  80

Leu Gln Met Asn Ser Leu Lys Pro Glu Asp Thr Ala Met Tyr Tyr Cys
                85                  90                  95

Ala Ala Asp Ser Phe His Asp Pro Thr Cys Thr Val Val Ala Ser Ser
            100                 105                 110

Gly Ala Phe Gln Tyr Trp Gly Gln Gly Thr Gln Val Thr Val Ser Ser
        115                 120                 125

<210> SEQ ID NO 27
<211> LENGTH: 125
<212> TYPE: PRT
<213> ORGANISM: Artificial Sequence
<220> FEATURE:
<223> OTHER INFORMATION: A synthetic antibody No.38

<400> SEQUENCE: 27

Gln Val Gln Leu Gln Glu Ser Gly Gly Gly Ser Val Gln Ala Gly Gly
1               5                   10                  15

Ser Leu Arg Leu Ser Cys Ala Val Ser Gly Phe Ile Ser Ser Arg Arg
            20                  25                  30

Cys Met Gly Trp Phe Arg Gln Ala Pro Gly Lys Glu Arg Val Gly Val
        35                  40                  45

Ala Asn Ile Thr Gly Thr Gly Asn Thr Tyr Leu Ala Asp Ser Val Lys
    50                  55                  60

Gly Arg Phe Thr Ile Ser Gln Asn Asn Ala Lys Ser Thr Val Tyr Leu
65                  70                  75                  80

Gln Met Asn Ser Leu Lys Pro Glu Asp Thr Ala Met Tyr Tyr Cys Ala
                85                  90                  95

Ala Asp Ser Phe Pro Thr Cys Thr Val Val Ala Ser Ser Gly Ala Phe
            100                 105                 110

Gln Tyr Trp Gly Gln Gly Thr Gln Val Thr Val Ser Ser
        115                 120                 125

<210> SEQ ID NO 28
<211> LENGTH: 128
<212> TYPE: PRT
<213> ORGANISM: Artificial Sequence
<220> FEATURE:
<223> OTHER INFORMATION: A synthetic antibody No.56

<400> SEQUENCE: 28

Gln Val Gln Leu Gln Glu Ser Gly Gly Gly Leu Val Gln Pro Gly Gly
1               5                   10                  15

Ser Leu Arg Leu Ser Cys Ala Ala Ser Gly Lys Met Ser Ser Arg Arg
            20                  25                  30

Cys Met Ala Trp Phe Arg Gln Ala Pro Gly Lys Glu Arg Glu Arg Val
        35                  40                  45
```

Ala Lys Leu Leu Thr Thr Ser Gly Ser Thr Tyr Leu Ala Asp Ser Val
        50                  55                  60

Lys Gly Arg Phe Thr Ile Ser Gln Asn Asn Ala Lys Ser Thr Val Tyr
65                  70                  75                  80

Leu Gln Met Asn Ser Leu Lys Pro Glu Asp Thr Ala Met Tyr Tyr Cys
                85                  90                  95

Ala Ala Asp Ser Phe Glu Asp Pro Thr Cys Thr Leu Val Thr Ser Ser
                100                 105                 110

Gly Ala Phe Gln Tyr Trp Gly Gln Gly Thr Gln Val Thr Val Ser Ser
            115                 120                 125

<210> SEQ ID NO 29
<211> LENGTH: 128
<212> TYPE: PRT
<213> ORGANISM: Artificial Sequence
<220> FEATURE:
<223> OTHER INFORMATION: A synthetic antibody No.69

<400> SEQUENCE: 29

Gln Val Gln Leu Gln Glu Ser Gly Gly Gly Ser Val Gln Ala Gly Gly
1               5                   10                  15

Ser Leu Arg Leu Ser Cys Ala Val Gln Arg Asn Ile Ser Ser Tyr
            20                  25                  30

Cys Met Ala Trp Phe Arg Gln Ala Pro Gly Lys Gln Arg Glu Arg Val
            35                  40                  45

Asp Lys Ile Leu Thr Thr Pro Gly Asn Thr Tyr Leu Ala Asp Ser Val
        50                  55                  60

Lys Gly Arg Phe Thr Ile Ser Gln Asn Asn Ala Lys Ser Thr Val Tyr
65                  70                  75                  80

Leu Gln Met Asn Ser Leu Lys Pro Glu Asp Thr Ala Met Tyr Tyr Cys
                85                  90                  95

Ala Ala Asp Ser Phe Gln Lys Pro Thr Cys Thr Val Val Ala Ser Trp
                100                 105                 110

Pro Ala Phe Gln Tyr Trp Gly Gln Gly Thr Gln Val Thr Val Ser Ser
            115                 120                 125

<210> SEQ ID NO 30
<211> LENGTH: 128
<212> TYPE: PRT
<213> ORGANISM: Artificial Sequence
<220> FEATURE:
<223> OTHER INFORMATION: A synthetic antibody No.81

<400> SEQUENCE: 30

Gln Val Gln Leu Gln Glu Ser Gly Gly Gly Ser Val Gln Ala Gly Gly
1               5                   10                  15

Ser Leu Arg Leu Ser Cys Ala Ala Ser Gly Asn Ile Ile Arg Val Arg
            20                  25                  30

Cys Met Ala Trp Phe Arg Gln Ala Pro Gly Lys Glu Arg Glu Arg Gly
            35                  40                  45

Pro Asn Ile Leu Thr Thr Thr Ile Ser Thr Tyr Leu Ala Asp Ser Val
        50                  55                  60

Lys Gly Arg Phe Thr Ile Ser Gln Asn Asn Ala Lys Ser Thr Val Tyr
65                  70                  75                  80

Leu Gln Met Asn Ser Leu Lys Pro Glu Asp Thr Ala Met Tyr Tyr Cys
                85                  90                  95

Ala Ala Asp Ser Phe Gly Tyr Pro Thr Cys Pro Gly Pro Ala Ser Ser
                100                 105                 110

```
Gly Ala Phe Gln Tyr Trp Gly Gln Gly Thr Gln Val Thr Val Ser Ser
        115                 120                 125
```

<210> SEQ ID NO 31
<211> LENGTH: 129
<212> TYPE: PRT
<213> ORGANISM: Artificial Sequence
<220> FEATURE:
<223> OTHER INFORMATION: A synthetic antibody No.87

<400> SEQUENCE: 31

```
Gln Val Gln Leu Gln Glu Ser Gly Gly Ser Val Gln Ala Gly Gly
1               5                   10                  15

Ser Leu Lys Leu Ser Cys Ala Ala Ser Gly Tyr Ile Phe Ser Ser Cys
                20                  25                  30

Gly Met Gly Trp Tyr Arg Gln Ala Pro Gly Lys Glu Arg Glu Leu Val
            35                  40                  45

Ser Thr Ile Ser Ser Asp Gly Thr Thr Ser Tyr Ala Asp Ser Val Lys
        50                  55                  60

Gly Arg Phe Thr Ile Ser Gln Asp Asn Ala Lys Asn Thr Leu Tyr Leu
65                  70                  75                  80

Gln Met Asn Ser Leu Lys Thr Glu Asp Thr Ala Val Tyr Tyr Cys Val
                85                  90                  95

Ala Asp Cys Pro Pro Ile Pro Glu Phe Thr Ser Cys Ser Gly Gly Tyr
            100                 105                 110

Cys Leu Ser Gly Asp Tyr Trp Gly Gln Gly Thr Gln Val Thr Val Ser
        115                 120                 125

Ser
```

<210> SEQ ID NO 32
<211> LENGTH: 124
<212> TYPE: PRT
<213> ORGANISM: Artificial Sequence
<220> FEATURE:
<223> OTHER INFORMATION: A synthetic antibody No.94

<400> SEQUENCE: 32

```
Gln Val Gln Leu Gln Glu Ser Gly Gly Ser Val Gln Ala Gly Gly
1               5                   10                  15

Ser Leu Arg Leu Ser Cys Ala Ala Ser Leu Asn Ile Phe Ser Ser Tyr
                20                  25                  30

Cys Met Gly Trp Phe Arg Gln Ala Pro Gly Lys Gln Arg Val Gly Val
            35                  40                  45

Ala Thr Ile Asp Ser Asp Gly Thr Thr Arg Tyr Val Asp Ser Val Lys
        50                  55                  60

Gly Arg Phe Thr Ile Ser Lys Asp Asn Ala Lys Asn Thr Leu Asp Leu
65                  70                  75                  80

Gln Met Asn Ser Leu Lys Pro Glu Asp Thr Ala Met Tyr Tyr Cys Ala
                85                  90                  95

Ala Arg Leu Asn Cys Pro Gly Pro Val Asp Trp Val Pro Met Phe Pro
            100                 105                 110

Tyr Arg Gly Gln Gly Thr Gln Val Thr Val Ser Ser
        115                 120
```

<210> SEQ ID NO 33
<211> LENGTH: 128
<212> TYPE: PRT
<213> ORGANISM: Artificial Sequence -continued

```
<220> FEATURE:
<223> OTHER INFORMATION: A synthetic Hu56V1

<400> SEQUENCE: 33

Gln Val Gln Leu Val Glu Ser Gly Gly Gly Leu Val Gln Pro Gly Gly
1               5                   10                  15

Ser Leu Arg Leu Ser Cys Ala Ala Ser Gly Lys Met Ser Ser Arg Arg
            20                  25                  30

Cys Met Ala Trp Phe Arg Gln Ala Pro Gly Lys Glu Arg Glu Arg Val
        35                  40                  45

Ala Lys Leu Leu Thr Thr Ser Gly Ser Thr Tyr Leu Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Ala Glu Asp Thr Ala Val Tyr Tyr Cys
                85                  90                  95

Ala Ala Asp Ser Phe Glu Asp Pro Thr Cys Thr Leu Val Thr Ser Ser
            100                 105                 110

Gly Ala Phe Gln Tyr Trp Gly Gln Gly Thr Leu Val Thr Val Ser Ser
        115                 120                 125

<210> SEQ ID NO 34
<211> LENGTH: 128
<212> TYPE: PRT
<213> ORGANISM: Artificial Sequence
<220> FEATURE:
<223> OTHER INFORMATION: A synthetic Hu56V2

<400> SEQUENCE: 34

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Arg
            20                  25                  30

Cys Met Ala Trp Phe Arg Gln Ala Pro Gly Lys Glu Arg Glu Arg Val
        35                  40                  45

Ala Lys Leu Leu Thr Thr Ser Gly Ser Thr Tyr Leu Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Ala Glu Asp Thr Ala Val Tyr Tyr Cys
                85                  90                  95

Ala Ala Asp Ser Phe Glu Asp Pro Thr Cys Thr Leu Val Thr Ser Ser
            100                 105                 110

Gly Ala Phe Gln Tyr Trp Gly Gln Gly Thr Leu Val Thr Val Ser Ser
        115                 120                 125

<210> SEQ ID NO 35
<211> LENGTH: 128
<212> TYPE: PRT
<213> ORGANISM: Artificial Sequence
<220> FEATURE:
<223> OTHER INFORMATION: A synthetic Hu56V3

<400> SEQUENCE: 35

Gln Val Gln Leu Val Glu Ser Gly Gly Gly Leu Val Gln Pro Gly Gly
1               5                   10                  15

Ser Leu Arg Leu Ser Cys Ala Ser Gly Lys Met Ser Ser Arg Arg
            20                  25                  30
```

Cys Met Ala Trp Phe Arg Gln Ala Pro Gly Lys Gly Leu Glu Arg Val
            35                  40                  45

Ala Lys Leu Leu Thr Thr Ser Gly Ser Thr Tyr Leu Ala Asp Ser Val
        50                  55                  60

Lys Gly Arg Phe Thr Ile Ser Arg Asp Asn Ser Lys Asn Thr Val Tyr
 65                  70                  75                  80

Leu Gln Met Asn Ser Leu Arg Ala Glu Asp Thr Ala Val Tyr Tyr Cys
                85                  90                  95

Ala Ala Asp Ser Phe Glu Asp Pro Thr Cys Thr Leu Val Thr Ser Ser
            100                 105                 110

Gly Ala Phe Gln Tyr Trp Gly Gln Gly Thr Leu Val Thr Val Ser Ser
            115                 120                 125

<210> SEQ ID NO 36
<211> LENGTH: 128
<212> TYPE: PRT
<213> ORGANISM: Artificial Sequence
<220> FEATURE:
<223> OTHER INFORMATION: A synthetic Hu56V4

<400> SEQUENCE: 36

Gln Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Arg Arg
            20                  25                  30

Cys Met Ala Trp Phe Arg Gln Ala Pro Gly Lys Gly Leu Glu Arg Val
            35                  40                  45

Ala Lys Leu Leu Thr Thr Ser Gly Ser Thr Tyr Leu Ala Asp Ser Val
        50                  55                  60

Lys Gly Arg Phe Thr Ile Ser Arg Asp Asn Ser Lys Asn Thr Val Tyr
 65                  70                  75                  80

Leu Gln Met Asn Ser Leu Arg Ala Glu Asp Thr Ala Val Tyr Tyr Cys
                85                  90                  95

Ala Ala Asp Ser Phe Glu Asp Pro Thr Cys Thr Leu Val Thr Ser Ser
            100                 105                 110

Gly Ala Phe Gln Tyr Trp Gly Gln Gly Thr Leu Val Thr Val Ser Ser
            115                 120                 125

<210> SEQ ID NO 37
<211> LENGTH: 128
<212> TYPE: PRT
<213> ORGANISM: Artificial Sequence
<220> FEATURE:
<223> OTHER INFORMATION: A synthetic Hu56V5

<400> SEQUENCE: 37

Gln Val Gln Leu Val Glu Ser Gly Gly Gly Leu Val Gln Pro Gly Gly
 1               5                  10                  15

Ser Leu Arg Leu Ser Cys Ala Ser Gly Lys Met Ser Ser Arg Arg
            20                  25                  30

Cys Met Ala Trp Phe Arg Gln Ala Pro Gly Lys Glu Arg Glu Arg Val
            35                  40                  45

Ala Lys Leu Leu Thr Thr Ser Gly Ser Thr Tyr Leu Ala Asp Ser Val
        50                  55                  60

Lys Gly Arg Phe Thr Ile Ser Arg Asp Asn Ser Lys Asn Thr Val Tyr
 65                  70                  75                  80

Leu Gln Met Asn Ser Leu Lys Ala Glu Asp Thr Ala Val Tyr Tyr Cys
                85                  90                  95

```
Ala Ala Asp Ser Phe Glu Asp Pro Thr Cys Thr Leu Val Thr Ser Ser
            100                 105                 110

Gly Ala Phe Gln Tyr Trp Gly Gln Gly Thr Leu Val Thr Val Ser Ser
            115                 120                 125

<210> SEQ ID NO 38
<211> LENGTH: 232
<212> TYPE: PRT
<213> ORGANISM: Artificial Sequence
<220> FEATURE:
<223> OTHER INFORMATION: A synthetic human IgG1 Fc

<400> SEQUENCE: 38

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
            35                  40                  45

Val Asp Val Ser His Glu Asp Pro Glu Val Lys Phe Asn Trp Tyr Val
50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
            115                 120                 125

Arg Glu Pro Gln Val Tyr Thr Leu Pro Pro Ser Arg Asp Glu Leu Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
            195                 200                 205

Ser Cys Ser Val Met His Glu Ala Leu His Asn His Tyr Thr Gln Lys
210                 215                 220

Ser Leu Ser Leu Ser Pro Gly Lys
225                 230

<210> SEQ ID NO 39
<211> LENGTH: 356
<212> TYPE: PRT
<213> ORGANISM: Artificial Sequence
<220> FEATURE:
<223> OTHER INFORMATION: A synthetic 10-Fc

<400> SEQUENCE: 39

Gln Val Gln Leu Gln Glu Ser Gly Gly Gly Ser Val Gln Ala Gly Gly
1               5                   10                  15

Ser Leu Arg Leu Ser Cys Ala Ala Ser Gly Asn Ile Val Ser Ser Tyr
            20                  25                  30

Cys Met Gly Trp Phe Arg Gln Ala Pro Gly Lys Glu Arg Val Gly Val
```

```
                35                  40                  45
Ala Ala Ile Asp Ser Asp Gly Thr Thr Lys Tyr Ala Asp Ser Met Lys
50                  55                  60

Gly Arg Phe Thr Ile Ser Lys Asp Asn Ala Lys Asn Thr Leu Asp Leu
65                  70                  75                  80

Gln Met Asn Ser Leu Lys Pro Glu Asp Thr Ala Met Tyr Tyr Cys Val
                85                  90                  95

Ala Arg Leu Asn Cys Pro Gly Pro Val Asp Trp Val Pro Met Phe Pro
            100                 105                 110

Tyr Arg Gly Gln Gly Thr Gln Val Thr Val Ser Ser Glu Pro Lys Ser
        115                 120                 125

Cys Asp Lys Thr His Thr Cys Pro Pro Cys Pro Ala Pro Glu Leu Leu
    130                 135                 140

Gly Gly Pro Ser Val Phe Leu Phe Pro Pro Lys Pro Lys Asp Thr Leu
145                 150                 155                 160

Met Ile Ser Arg Thr Pro Glu Val Thr Cys Val Val Val Asp Val Ser
                165                 170                 175

His Glu Asp Pro Glu Val Lys Phe Asn Trp Tyr Val Asp Gly Val Glu
            180                 185                 190

Val His Asn Ala Lys Thr Lys Pro Arg Glu Glu Gln Tyr Asn Ser Thr
        195                 200                 205

Tyr Arg Val Val Ser Val Leu Thr Val Leu His Gln Asp Trp Leu Asn
    210                 215                 220

Gly Lys Glu Tyr Lys Cys Lys Val Ser Asn Lys Ala Leu Pro Ala Pro
225                 230                 235                 240

Ile Glu Lys Thr Ile Ser Lys Ala Lys Gly Gln Pro Arg Glu Pro Gln
                245                 250                 255

Val Tyr Thr Leu Pro Pro Ser Arg Asp Glu Leu Thr Lys Asn Gln Val
            260                 265                 270

Ser Leu Thr Cys Leu Val Lys Gly Phe Tyr Pro Ser Asp Ile Ala Val
        275                 280                 285

Glu Trp Glu Ser Asn Gly Gln Pro Glu Asn Asn Tyr Lys Thr Thr Pro
    290                 295                 300

Pro Val Leu Asp Ser Asp Gly Ser Phe Phe Leu Tyr Ser Lys Leu Thr
305                 310                 315                 320

Val Asp Lys Ser Arg Trp Gln Gln Gly Asn Val Phe Ser Cys Ser Val
                325                 330                 335

Met His Glu Ala Leu His Asn His Tyr Thr Gln Lys Ser Leu Ser Leu
            340                 345                 350

Ser Pro Gly Lys
        355

<210> SEQ ID NO 40
<211> LENGTH: 360
<212> TYPE: PRT
<213> ORGANISM: Artificial Sequence
<220> FEATURE:
<223> OTHER INFORMATION: A synthetic 27-Fc

<400> SEQUENCE: 40

Gln Val Gln Leu Gln Glu Ser Gly Gly Gly Ser Val Gln Ala Gly Gly
1               5                   10                  15

Ser Leu Arg Leu Ser Cys Ala Ala Ser Gly Asn Ile Ser Ser Arg Arg
            20                  25                  30

Cys Met Ala Trp Phe Arg Gln Ala Pro Gly Lys Glu Arg Glu Arg Val
```

```
                35                  40                  45
Ala Asn Ile Leu Thr Thr Thr Gly Asn Thr Tyr Leu Ala Asp Ser Val
     50                  55                  60

Lys Gly Arg Phe Thr Ile Ser Gln Asn Asn Ala Lys Ser Thr Val Tyr
 65                  70                  75                  80

Leu Gln Met Asn Ser Leu Lys Pro Glu Asp Thr Ala Met Tyr Tyr Cys
                 85                  90                  95

Ala Ala Asp Ser Phe His Asp Pro Thr Cys Thr Val Val Ala Ser Ser
             100                 105                 110

Gly Ala Phe Gln Tyr Trp Gly Gln Gly Thr Gln Val Thr Val Ser Ser
         115                 120                 125

Glu Pro Lys Ser Cys Asp Lys Thr His Thr Cys Pro Pro Cys Pro Ala
     130                 135                 140

Pro Glu Leu Leu Gly Gly Pro Ser Val Phe Leu Phe Pro Pro Lys Pro
145                 150                 155                 160

Lys Asp Thr Leu Met Ile Ser Arg Thr Pro Glu Val Thr Cys Val Val
                165                 170                 175

Val Asp Val Ser His Glu Asp Pro Glu Val Lys Phe Asn Trp Tyr Val
            180                 185                 190

Asp Gly Val Glu Val His Asn Ala Lys Thr Lys Pro Arg Glu Glu Gln
        195                 200                 205

Tyr Asn Ser Thr Tyr Arg Val Val Ser Val Leu Thr Val Leu His Gln
    210                 215                 220

Asp Trp Leu Asn Gly Lys Glu Tyr Lys Cys Lys Val Ser Asn Lys Ala
225                 230                 235                 240

Leu Pro Ala Pro Ile Glu Lys Thr Ile Ser Lys Ala Lys Gly Gln Pro
                245                 250                 255

Arg Glu Pro Gln Val Tyr Thr Leu Pro Pro Ser Arg Asp Glu Leu Thr
            260                 265                 270

Lys Asn Gln Val Ser Leu Thr Cys Leu Val Lys Gly Phe Tyr Pro Ser
        275                 280                 285

Asp Ile Ala Val Glu Trp Glu Ser Asn Gly Gln Pro Glu Asn Asn Tyr
    290                 295                 300

Lys Thr Thr Pro Pro Val Leu Asp Ser Asp Gly Ser Phe Phe Leu Tyr
305                 310                 315                 320

Ser Lys Leu Thr Val Asp Lys Ser Arg Trp Gln Gln Gly Asn Val Phe
                325                 330                 335

Ser Cys Ser Val Met His Glu Ala Leu His Asn His Tyr Thr Gln Lys
            340                 345                 350

Ser Leu Ser Leu Ser Pro Gly Lys
        355                 360

<210> SEQ ID NO 41
<211> LENGTH: 357
<212> TYPE: PRT
<213> ORGANISM: Artificial Sequence
<220> FEATURE:
<223> OTHER INFORMATION: A synthetic 38-Fc

<400> SEQUENCE: 41

Gln Val Gln Leu Gln Glu Ser Gly Gly Gly Ser Val Gln Ala Gly Gly
  1               5                  10                  15

Ser Leu Arg Leu Ser Cys Ala Val Ser Gly Phe Ile Ser Ser Arg Arg
             20                  25                  30

Cys Met Gly Trp Phe Arg Gln Ala Pro Gly Lys Glu Arg Val Gly Val
```

```
                35                  40                  45
Ala Asn Ile Thr Gly Thr Gly Asn Thr Tyr Leu Ala Asp Ser Val Lys
            50                  55                  60

Gly Arg Phe Thr Ile Ser Gln Asn Asn Ala Lys Ser Thr Val Tyr Leu
65                  70                  75                  80

Gln Met Asn Ser Leu Lys Pro Glu Asp Thr Ala Met Tyr Tyr Cys Ala
                85                  90                  95

Ala Asp Ser Phe Pro Thr Cys Thr Val Val Ala Ser Ser Gly Ala Phe
            100                 105                 110

Gln Tyr Trp Gly Gln Gly Thr Gln Val Thr Val Ser Ser Glu Pro Lys
        115                 120                 125

Ser Cys Asp Lys Thr His Thr Cys Pro Pro Cys Pro Ala Pro Glu Leu
    130                 135                 140

Leu Gly Gly Pro Ser Val Phe Leu Phe Pro Pro Lys Pro Lys Asp Thr
145                 150                 155                 160

Leu Met Ile Ser Arg Thr Pro Glu Val Thr Cys Val Val Val Asp Val
                165                 170                 175

Ser His Glu Asp Pro Glu Val Lys Phe Asn Trp Tyr Val Asp Gly Val
            180                 185                 190

Glu Val His Asn Ala Lys Thr Lys Pro Arg Glu Glu Gln Tyr Asn Ser
        195                 200                 205

Thr Tyr Arg Val Val Ser Val Leu Thr Val Leu His Gln Asp Trp Leu
    210                 215                 220

Asn Gly Lys Glu Tyr Lys Cys Lys Val Ser Asn Lys Ala Leu Pro Ala
225                 230                 235                 240

Pro Ile Glu Lys Thr Ile Ser Lys Ala Lys Gly Gln Pro Arg Glu Pro
                245                 250                 255

Gln Val Tyr Thr Leu Pro Pro Ser Arg Asp Glu Leu Thr Lys Asn Gln
            260                 265                 270

Val Ser Leu Thr Cys Leu Val Lys Gly Phe Tyr Pro Ser Asp Ile Ala
        275                 280                 285

Val Glu Trp Glu Ser Asn Gly Gln Pro Glu Asn Asn Tyr Lys Thr Thr
    290                 295                 300

Pro Pro Val Leu Asp Ser Asp Gly Ser Phe Phe Leu Tyr Ser Lys Leu
305                 310                 315                 320

Thr Val Asp Lys Ser Arg Trp Gln Gln Gly Asn Val Phe Ser Cys Ser
                325                 330                 335

Val Met His Glu Ala Leu His Asn His Tyr Thr Gln Lys Ser Leu Ser
            340                 345                 350

Leu Ser Pro Gly Lys
        355

<210> SEQ ID NO 42
<211> LENGTH: 360
<212> TYPE: PRT
<213> ORGANISM: Artificial Sequence
<220> FEATURE:
<223> OTHER INFORMATION: A synthetic 56-Fc

<400> SEQUENCE: 42

Gln Val Gln Leu Gln Glu Ser Gly Gly Gly Leu Val Gln Pro Gly Gly
1               5                   10                  15

Ser Leu Arg Leu Ser Cys Ala Ala Ser Gly Lys Met Ser Ser Arg Arg
            20                  25                  30

Cys Met Ala Trp Phe Arg Gln Ala Pro Gly Lys Glu Arg Glu Arg Val
```

```
            35                  40                  45
Ala Lys Leu Leu Thr Thr Ser Gly Ser Thr Tyr Leu Ala Asp Ser Val
 50                  55                  60

Lys Gly Arg Phe Thr Ile Ser Gln Asn Asn Ala Lys Ser Thr Val Tyr
 65                  70                  75                  80

Leu Gln Met Asn Ser Leu Lys Pro Glu Asp Thr Ala Met Tyr Tyr Cys
                 85                  90                  95

Ala Ala Asp Ser Phe Glu Asp Pro Thr Cys Thr Leu Val Thr Ser Ser
                100                 105                 110

Gly Ala Phe Gln Tyr Trp Gly Gln Gly Thr Gln Val Thr Val Ser Ser
            115                 120                 125

Glu Pro Lys Ser Cys Asp Lys Thr His Thr Cys Pro Pro Cys Pro Ala
130                 135                 140

Pro Glu Leu Leu Gly Gly Pro Ser Val Phe Leu Phe Pro Pro Lys Pro
145                 150                 155                 160

Lys Asp Thr Leu Met Ile Ser Arg Thr Pro Glu Val Thr Cys Val Val
                165                 170                 175

Val Asp Val Ser His Glu Asp Pro Glu Val Lys Phe Asn Trp Tyr Val
            180                 185                 190

Asp Gly Val Glu Val His Asn Ala Lys Thr Lys Pro Arg Glu Glu Gln
        195                 200                 205

Tyr Asn Ser Thr Tyr Arg Val Val Ser Val Leu Thr Val Leu His Gln
    210                 215                 220

Asp Trp Leu Asn Gly Lys Glu Tyr Lys Cys Lys Val Ser Asn Lys Ala
225                 230                 235                 240

Leu Pro Ala Pro Ile Glu Lys Thr Ile Ser Lys Ala Lys Gly Gln Pro
                245                 250                 255

Arg Glu Pro Gln Val Tyr Thr Leu Pro Pro Ser Arg Asp Glu Leu Thr
            260                 265                 270

Lys Asn Gln Val Ser Leu Thr Cys Leu Val Lys Gly Phe Tyr Pro Ser
        275                 280                 285

Asp Ile Ala Val Glu Trp Glu Ser Asn Gly Gln Pro Glu Asn Asn Tyr
    290                 295                 300

Lys Thr Thr Pro Pro Val Leu Asp Ser Asp Gly Ser Phe Phe Leu Tyr
305                 310                 315                 320

Ser Lys Leu Thr Val Asp Lys Ser Arg Trp Gln Gln Gly Asn Val Phe
                325                 330                 335

Ser Cys Ser Val Met His Glu Ala Leu His Asn His Tyr Thr Gln Lys
            340                 345                 350

Ser Leu Ser Leu Ser Pro Gly Lys
        355                 360

<210> SEQ ID NO 43
<211> LENGTH: 360
<212> TYPE: PRT
<213> ORGANISM: Artificial Sequence
<220> FEATURE:
<223> OTHER INFORMATION: A synthetic 69-Fc

<400> SEQUENCE: 43

Gln Val Gln Leu Gln Glu Ser Gly Gly Gly Ser Val Gln Ala Gly Gly
 1               5                  10                  15

Ser Leu Arg Leu Ser Cys Ala Val Gln Arg Asn Ile Ser Ser Ser Tyr
             20                  25                  30

Cys Met Ala Trp Phe Arg Gln Ala Pro Gly Lys Gln Arg Glu Arg Val
```

```
                35                  40                  45
Asp Lys Ile Leu Thr Thr Pro Gly Asn Thr Tyr Leu Ala Asp Ser Val
 50                  55                  60

Lys Gly Arg Phe Thr Ile Ser Gln Asn Asn Ala Lys Ser Thr Val Tyr
 65                  70                  75                  80

Leu Gln Met Asn Ser Leu Lys Pro Glu Asp Thr Ala Met Tyr Tyr Cys
                 85                  90                  95

Ala Ala Asp Ser Phe Gln Lys Pro Thr Cys Thr Val Val Ala Ser Trp
                100                 105                 110

Pro Ala Phe Gln Tyr Trp Gly Gln Gly Thr Gln Val Thr Val Ser Ser
                115                 120                 125

Glu Pro Lys Ser Cys Asp Lys Thr His Thr Cys Pro Pro Cys Pro Ala
130                 135                 140

Pro Glu Leu Leu Gly Gly Pro Ser Val Phe Leu Phe Pro Pro Lys Pro
145                 150                 155                 160

Lys Asp Thr Leu Met Ile Ser Arg Thr Pro Glu Val Thr Cys Val Val
                165                 170                 175

Val Asp Val Ser His Glu Asp Pro Glu Val Lys Phe Asn Trp Tyr Val
                180                 185                 190

Asp Gly Val Glu Val His Asn Ala Lys Thr Lys Pro Arg Glu Glu Gln
                195                 200                 205

Tyr Asn Ser Thr Tyr Arg Val Val Ser Val Leu Thr Val Leu His Gln
210                 215                 220

Asp Trp Leu Asn Gly Lys Glu Tyr Lys Cys Lys Val Ser Asn Lys Ala
225                 230                 235                 240

Leu Pro Ala Pro Ile Glu Lys Thr Ile Ser Lys Ala Lys Gly Gln Pro
                245                 250                 255

Arg Glu Pro Gln Val Tyr Thr Leu Pro Pro Ser Arg Asp Glu Leu Thr
                260                 265                 270

Lys Asn Gln Val Ser Leu Thr Cys Leu Val Lys Gly Phe Tyr Pro Ser
                275                 280                 285

Asp Ile Ala Val Glu Trp Glu Ser Asn Gly Gln Pro Glu Asn Asn Tyr
290                 295                 300

Lys Thr Thr Pro Pro Val Leu Asp Ser Asp Gly Ser Phe Phe Leu Tyr
305                 310                 315                 320

Ser Lys Leu Thr Val Asp Lys Ser Arg Trp Gln Gln Gly Asn Val Phe
                325                 330                 335

Ser Cys Ser Val Met His Glu Ala Leu His Asn His Tyr Thr Gln Lys
                340                 345                 350

Ser Leu Ser Leu Ser Pro Gly Lys
                355                 360

<210> SEQ ID NO 44
<211> LENGTH: 360
<212> TYPE: PRT
<213> ORGANISM: Artificial Sequence
<220> FEATURE:
<223> OTHER INFORMATION: A synthetic 81-Fc

<400> SEQUENCE: 44

Gln Val Gln Leu Gln Glu Ser Gly Gly Gly Ser Val Gln Ala Gly Gly
  1               5                  10                  15

Ser Leu Arg Leu Ser Cys Ala Ala Ser Gly Asn Ile Ile Arg Val Arg
                 20                  25                  30

Cys Met Ala Trp Phe Arg Gln Ala Pro Gly Lys Glu Arg Glu Arg Gly
```

```
                35                  40                  45
Pro Asn Ile Leu Thr Thr Thr Ile Ser Thr Tyr Leu Ala Asp Ser Val
 50                  55                  60

Lys Gly Arg Phe Thr Ile Ser Gln Asn Asn Ala Lys Ser Thr Val Tyr
 65                  70                  75                  80

Leu Gln Met Asn Ser Leu Lys Pro Glu Asp Thr Ala Met Tyr Tyr Cys
                 85                  90                  95

Ala Ala Asp Ser Phe Gly Tyr Pro Thr Cys Pro Gly Pro Ala Ser Ser
                100                 105                 110

Gly Ala Phe Gln Tyr Trp Gly Gln Gly Thr Gln Val Thr Val Ser Ser
                115                 120                 125

Glu Pro Lys Ser Cys Asp Lys Thr His Thr Cys Pro Pro Cys Pro Ala
130                 135                 140

Pro Glu Leu Leu Gly Gly Pro Ser Val Phe Leu Phe Pro Pro Lys Pro
145                 150                 155                 160

Lys Asp Thr Leu Met Ile Ser Arg Thr Pro Glu Val Thr Cys Val Val
                165                 170                 175

Val Asp Val Ser His Glu Asp Pro Glu Val Lys Phe Asn Trp Tyr Val
                180                 185                 190

Asp Gly Val Glu Val His Asn Ala Lys Thr Lys Pro Arg Glu Glu Gln
                195                 200                 205

Tyr Asn Ser Thr Tyr Arg Val Val Ser Val Leu Thr Val Leu His Gln
                210                 215                 220

Asp Trp Leu Asn Gly Lys Glu Tyr Lys Cys Lys Val Ser Asn Lys Ala
225                 230                 235                 240

Leu Pro Ala Pro Ile Glu Lys Thr Ile Ser Lys Ala Lys Gly Gln Pro
                245                 250                 255

Arg Glu Pro Gln Val Tyr Thr Leu Pro Pro Ser Arg Asp Glu Leu Thr
                260                 265                 270

Lys Asn Gln Val Ser Leu Thr Cys Leu Val Lys Gly Phe Tyr Pro Ser
                275                 280                 285

Asp Ile Ala Val Glu Trp Glu Ser Asn Gly Gln Pro Glu Asn Asn Tyr
290                 295                 300

Lys Thr Thr Pro Pro Val Leu Asp Ser Asp Gly Ser Phe Phe Leu Tyr
305                 310                 315                 320

Ser Lys Leu Thr Val Asp Lys Ser Arg Trp Gln Gln Gly Asn Val Phe
                325                 330                 335

Ser Cys Ser Val Met His Glu Ala Leu His Asn His Tyr Thr Gln Lys
                340                 345                 350

Ser Leu Ser Leu Ser Pro Gly Lys
            355                 360

<210> SEQ ID NO 45
<211> LENGTH: 361
<212> TYPE: PRT
<213> ORGANISM: Artificial Sequence
<220> FEATURE:
<223> OTHER INFORMATION: A synthetic 87-Fc

<400> SEQUENCE: 45

Gln Val Gln Leu Gln Glu Ser Gly Gly Gly Ser Val Gln Ala Gly Gly
  1               5                  10                  15

Ser Leu Lys Leu Ser Cys Ala Ala Ser Gly Tyr Ile Phe Ser Ser Cys
                 20                  25                  30

Gly Met Gly Trp Tyr Arg Gln Ala Pro Gly Lys Glu Arg Glu Leu Val
```

```
            35                  40                  45
Ser Thr Ile Ser Ser Asp Gly Thr Thr Ser Tyr Ala Asp Ser Val Lys
        50                  55                  60

Gly Arg Phe Thr Ile Ser Gln Asp Asn Ala Lys Asn Thr Leu Tyr Leu
65                  70                  75                  80

Gln Met Asn Ser Leu Lys Thr Glu Asp Thr Ala Val Tyr Tyr Cys Val
                85                  90                  95

Ala Asp Cys Pro Pro Ile Pro Glu Phe Thr Ser Cys Ser Gly Gly Tyr
            100                 105                 110

Cys Leu Ser Gly Asp Tyr Trp Gly Gln Gly Thr Gln Val Thr Val Ser
        115                 120                 125

Ser Glu Pro Lys Ser Cys Asp Lys Thr His Thr Cys Pro Pro Cys Pro
130                 135                 140

Ala Pro Glu Leu Leu Gly Gly Pro Ser Val Phe Leu Phe Pro Pro Lys
145                 150                 155                 160

Pro Lys Asp Thr Leu Met Ile Ser Arg Thr Pro Glu Val Thr Cys Val
                165                 170                 175

Val Val Asp Val Ser His Glu Asp Pro Glu Val Lys Phe Asn Trp Tyr
            180                 185                 190

Val Asp Gly Val Glu Val His Asn Ala Lys Thr Lys Pro Arg Glu Glu
        195                 200                 205

Gln Tyr Asn Ser Thr Tyr Arg Val Val Ser Val Leu Thr Val Leu His
    210                 215                 220

Gln Asp Trp Leu Asn Gly Lys Glu Tyr Lys Cys Lys Val Ser Asn Lys
225                 230                 235                 240

Ala Leu Pro Ala Pro Ile Glu Lys Thr Ile Ser Lys Ala Lys Gly Gln
                245                 250                 255

Pro Arg Glu Pro Gln Val Tyr Thr Leu Pro Pro Ser Arg Asp Glu Leu
            260                 265                 270

Thr Lys Asn Gln Val Ser Leu Thr Cys Leu Val Lys Gly Phe Tyr Pro
        275                 280                 285

Ser Asp Ile Ala Val Glu Trp Glu Ser Asn Gly Gln Pro Glu Asn Asn
    290                 295                 300

Tyr Lys Thr Thr Pro Pro Val Leu Asp Ser Asp Gly Ser Phe Phe Leu
305                 310                 315                 320

Tyr Ser Lys Leu Thr Val Asp Lys Ser Arg Trp Gln Gln Gly Asn Val
                325                 330                 335

Phe Ser Cys Ser Val Met His Glu Ala Leu His Asn His Tyr Thr Gln
            340                 345                 350

Lys Ser Leu Ser Leu Ser Pro Gly Lys
        355                 360

<210> SEQ ID NO 46
<211> LENGTH: 356
<212> TYPE: PRT
<213> ORGANISM: Artificial Sequence
<220> FEATURE:
<223> OTHER INFORMATION: A synthetic 94-Fc

<400> SEQUENCE: 46

Gln Val Gln Leu Gln Glu Ser Gly Gly Gly Ser Val Gln Ala Gly Gly
1               5                   10                  15

Ser Leu Arg Leu Ser Cys Ala Ala Ser Leu Asn Ile Phe Ser Ser Tyr
            20                  25                  30

Cys Met Gly Trp Phe Arg Gln Ala Pro Gly Lys Gln Arg Val Gly Val
```

```
                35                  40                  45
Ala Thr Ile Asp Ser Asp Gly Thr Thr Arg Tyr Val Asp Ser Val Lys
 50                  55                  60
Gly Arg Phe Thr Ile Ser Lys Asp Asn Ala Lys Asn Thr Leu Asp Leu
 65                  70                  75                  80
Gln Met Asn Ser Leu Lys Pro Glu Asp Thr Ala Met Tyr Tyr Cys Ala
                 85                  90                  95
Ala Arg Leu Asn Cys Pro Gly Pro Val Asp Trp Val Pro Met Phe Pro
                100                 105                 110
Tyr Arg Gly Gln Gly Thr Gln Val Thr Val Ser Ser Glu Pro Lys Ser
                115                 120                 125
Cys Asp Lys Thr His Thr Cys Pro Pro Cys Pro Ala Pro Glu Leu Leu
                130                 135                 140
Gly Gly Pro Ser Val Phe Leu Phe Pro Pro Lys Pro Lys Asp Thr Leu
145                 150                 155                 160
Met Ile Ser Arg Thr Pro Glu Val Thr Cys Val Val Val Asp Val Ser
                165                 170                 175
His Glu Asp Pro Glu Val Lys Phe Asn Trp Tyr Val Asp Gly Val Glu
                180                 185                 190
Val His Asn Ala Lys Thr Lys Pro Arg Glu Glu Gln Tyr Asn Ser Thr
                195                 200                 205
Tyr Arg Val Val Ser Val Leu Thr Val Leu His Gln Asp Trp Leu Asn
                210                 215                 220
Gly Lys Glu Tyr Lys Cys Lys Val Ser Asn Lys Ala Leu Pro Ala Pro
225                 230                 235                 240
Ile Glu Lys Thr Ile Ser Lys Ala Lys Gly Gln Pro Arg Glu Pro Gln
                245                 250                 255
Val Tyr Thr Leu Pro Pro Ser Arg Asp Glu Leu Thr Lys Asn Gln Val
                260                 265                 270
Ser Leu Thr Cys Leu Val Lys Gly Phe Tyr Pro Ser Asp Ile Ala Val
                275                 280                 285
Glu Trp Glu Ser Asn Gly Gln Pro Glu Asn Asn Tyr Lys Thr Thr Pro
                290                 295                 300
Pro Val Leu Asp Ser Asp Gly Ser Phe Phe Leu Tyr Ser Lys Leu Thr
305                 310                 315                 320
Val Asp Lys Ser Arg Trp Gln Gln Gly Asn Val Phe Ser Cys Ser Val
                325                 330                 335
Met His Glu Ala Leu His Asn His Tyr Thr Gln Lys Ser Leu Ser Leu
                340                 345                 350
Ser Pro Gly Lys
            355

<210> SEQ ID NO 47
<211> LENGTH: 360
<212> TYPE: PRT
<213> ORGANISM: Artificial Sequence
<220> FEATURE:
<223> OTHER INFORMATION: A synthetic Hu56V1-Fc

<400> SEQUENCE: 47

Gln Val Gln Leu Val Glu Ser Gly Gly Gly Leu Val Gln Pro Gly Gly
  1               5                  10                  15
Ser Leu Arg Leu Ser Cys Ala Ala Ser Gly Lys Met Ser Ser Arg Arg
                 20                  25                  30
Cys Met Ala Trp Phe Arg Gln Ala Pro Gly Lys Glu Arg Glu Arg Val
```

```
                35                  40                  45
Ala Lys Leu Leu Thr Thr Ser Gly Ser Thr Tyr Leu Ala Asp Ser Val
 50                  55                  60
Lys Gly Arg Phe Thr Ile Ser Arg Asp Asn Ser Lys Asn Thr Val Tyr
 65                  70                  75                  80
Leu Gln Met Asn Ser Leu Arg Ala Glu Asp Thr Ala Val Tyr Tyr Cys
                 85                  90                  95
Ala Ala Asp Ser Phe Glu Asp Pro Thr Cys Thr Leu Val Thr Ser Ser
                100                 105                 110
Gly Ala Phe Gln Tyr Trp Gly Gln Gly Thr Leu Val Thr Val Ser Ser
                115                 120                 125
Glu Pro Lys Ser Cys Asp Lys Thr His Thr Cys Pro Pro Cys Pro Ala
130                 135                 140
Pro Glu Leu Leu Gly Gly Pro Ser Val Phe Leu Phe Pro Pro Lys Pro
145                 150                 155                 160
Lys Asp Thr Leu Met Ile Ser Arg Thr Pro Glu Val Thr Cys Val Val
                165                 170                 175
Val Asp Val Ser His Glu Asp Pro Glu Val Lys Phe Asn Trp Tyr Val
                180                 185                 190
Asp Gly Val Glu Val His Asn Ala Lys Thr Lys Pro Arg Glu Glu Gln
                195                 200                 205
Tyr Asn Ser Thr Tyr Arg Val Val Ser Val Leu Thr Val Leu His Gln
                210                 215                 220
Asp Trp Leu Asn Gly Lys Glu Tyr Lys Cys Lys Val Ser Asn Lys Ala
225                 230                 235                 240
Leu Pro Ala Pro Ile Glu Lys Thr Ile Ser Lys Ala Lys Gly Gln Pro
                245                 250                 255
Arg Glu Pro Gln Val Tyr Thr Leu Pro Pro Ser Arg Asp Glu Leu Thr
                260                 265                 270
Lys Asn Gln Val Ser Leu Thr Cys Leu Val Lys Gly Phe Tyr Pro Ser
                275                 280                 285
Asp Ile Ala Val Glu Trp Glu Ser Asn Gly Gln Pro Glu Asn Asn Tyr
290                 295                 300
Lys Thr Thr Pro Pro Val Leu Asp Ser Asp Gly Ser Phe Phe Leu Tyr
305                 310                 315                 320
Ser Lys Leu Thr Val Asp Lys Ser Arg Trp Gln Gln Gly Asn Val Phe
                325                 330                 335
Ser Cys Ser Val Met His Glu Ala Leu His Asn His Tyr Thr Gln Lys
                340                 345                 350
Ser Leu Ser Leu Ser Pro Gly Lys
                355                 360
```

<210> SEQ ID NO 48
<211> LENGTH: 360
<212> TYPE: PRT
<213> ORGANISM: Artificial Sequence
<220> FEATURE:
<223> OTHER INFORMATION: A synthetic Hu56V2-Fc

<400> SEQUENCE: 48

```
Gln Val Gln Leu Val Glu Ser Gly Gly Gly Leu Val Gln Pro Gly Gly
  1               5                  10                  15
Ser Leu Arg Leu Ser Cys Ala Ala Ser Gly Phe Thr Phe Ser Arg Arg
                 20                  25                  30
Cys Met Ala Trp Phe Arg Gln Ala Pro Gly Lys Glu Arg Glu Arg Val
```

```
                35                  40                  45
Ala Lys Leu Leu Thr Thr Ser Gly Ser Thr Tyr Leu Ala Asp Ser Val
 50                  55                  60

Lys Gly Arg Phe Thr Ile Ser Arg Asp Asn Ser Lys Asn Thr Val Tyr
 65                  70                  75                  80

Leu Gln Met Asn Ser Leu Arg Ala Glu Asp Thr Ala Val Tyr Tyr Cys
                 85                  90                  95

Ala Ala Asp Ser Phe Glu Asp Pro Thr Cys Thr Leu Val Thr Ser Ser
                100                 105                 110

Gly Ala Phe Gln Tyr Trp Gly Gln Gly Thr Leu Val Thr Val Ser Ser
            115                 120                 125

Glu Pro Lys Ser Cys Asp Lys Thr His Thr Cys Pro Pro Cys Pro Ala
130                 135                 140

Pro Glu Leu Leu Gly Gly Pro Ser Val Phe Leu Phe Pro Pro Lys Pro
145                 150                 155                 160

Lys Asp Thr Leu Met Ile Ser Arg Thr Pro Glu Val Thr Cys Val Val
                165                 170                 175

Val Asp Val Ser His Glu Asp Pro Glu Val Lys Phe Asn Trp Tyr Val
            180                 185                 190

Asp Gly Val Glu Val His Asn Ala Lys Thr Lys Pro Arg Glu Glu Gln
        195                 200                 205

Tyr Asn Ser Thr Tyr Arg Val Val Ser Val Leu Thr Val Leu His Gln
210                 215                 220

Asp Trp Leu Asn Gly Lys Glu Tyr Lys Cys Lys Val Ser Asn Lys Ala
225                 230                 235                 240

Leu Pro Ala Pro Ile Glu Lys Thr Ile Ser Lys Ala Lys Gly Gln Pro
                245                 250                 255

Arg Glu Pro Gln Val Tyr Thr Leu Pro Pro Ser Arg Asp Glu Leu Thr
            260                 265                 270

Lys Asn Gln Val Ser Leu Thr Cys Leu Val Lys Gly Phe Tyr Pro Ser
        275                 280                 285

Asp Ile Ala Val Glu Trp Glu Ser Asn Gly Gln Pro Glu Asn Asn Tyr
290                 295                 300

Lys Thr Thr Pro Pro Val Leu Asp Ser Asp Gly Ser Phe Phe Leu Tyr
305                 310                 315                 320

Ser Lys Leu Thr Val Asp Lys Ser Arg Trp Gln Gln Gly Asn Val Phe
                325                 330                 335

Ser Cys Ser Val Met His Glu Ala Leu His Asn His Tyr Thr Gln Lys
            340                 345                 350

Ser Leu Ser Leu Ser Pro Gly Lys
        355                 360

<210> SEQ ID NO 49
<211> LENGTH: 360
<212> TYPE: PRT
<213> ORGANISM: Artificial Sequence
<220> FEATURE:
<223> OTHER INFORMATION: A synthetic Hu56V3-Fc

<400> SEQUENCE: 49

Gln Val Gln Leu Val Glu Ser Gly Gly Gly Leu Val Gln Pro Gly Gly
  1               5                  10                  15

Ser Leu Arg Leu Ser Cys Ala Ala Ser Gly Lys Met Ser Ser Arg Arg
             20                  25                  30

Cys Met Ala Trp Phe Arg Gln Ala Pro Gly Lys Gly Leu Glu Arg Val
```

```
            35                  40                  45
Ala Lys Leu Leu Thr Thr Ser Gly Ser Thr Tyr Leu Ala Asp Ser Val
 50                  55                  60
Lys Gly Arg Phe Thr Ile Ser Arg Asp Asn Ser Lys Asn Thr Val Tyr
 65                  70                  75                  80
Leu Gln Met Asn Ser Leu Arg Ala Glu Asp Thr Ala Val Tyr Tyr Cys
                 85                  90                  95
Ala Ala Asp Ser Phe Glu Asp Pro Thr Cys Thr Leu Val Thr Ser Ser
            100                 105                 110
Gly Ala Phe Gln Tyr Trp Gly Gln Gly Thr Leu Val Thr Val Ser Ser
        115                 120                 125
Glu Pro Lys Ser Cys Asp Lys Thr His Thr Cys Pro Pro Cys Pro Ala
130                 135                 140
Pro Glu Leu Leu Gly Gly Pro Ser Val Phe Leu Phe Pro Pro Lys Pro
145                 150                 155                 160
Lys Asp Thr Leu Met Ile Ser Arg Thr Pro Glu Val Thr Cys Val Val
                165                 170                 175
Val Asp Val Ser His Glu Asp Pro Glu Val Lys Phe Asn Trp Tyr Val
            180                 185                 190
Asp Gly Val Glu Val His Asn Ala Lys Thr Lys Pro Arg Glu Glu Gln
        195                 200                 205
Tyr Asn Ser Thr Tyr Arg Val Val Ser Val Leu Thr Val Leu His Gln
210                 215                 220
Asp Trp Leu Asn Gly Lys Glu Tyr Lys Cys Lys Val Ser Asn Lys Ala
225                 230                 235                 240
Leu Pro Ala Pro Ile Glu Lys Thr Ile Ser Lys Ala Lys Gly Gln Pro
                245                 250                 255
Arg Glu Pro Gln Val Tyr Thr Leu Pro Pro Ser Arg Asp Glu Leu Thr
            260                 265                 270
Lys Asn Gln Val Ser Leu Thr Cys Leu Val Lys Gly Phe Tyr Pro Ser
        275                 280                 285
Asp Ile Ala Val Glu Trp Glu Ser Asn Gly Gln Pro Glu Asn Asn Tyr
290                 295                 300
Lys Thr Thr Pro Pro Val Leu Asp Ser Asp Gly Ser Phe Phe Leu Tyr
305                 310                 315                 320
Ser Lys Leu Thr Val Asp Lys Ser Arg Trp Gln Gln Gly Asn Val Phe
                325                 330                 335
Ser Cys Ser Val Met His Glu Ala Leu His Asn His Tyr Thr Gln Lys
            340                 345                 350
Ser Leu Ser Leu Ser Pro Gly Lys
        355                 360

<210> SEQ ID NO 50
<211> LENGTH: 360
<212> TYPE: PRT
<213> ORGANISM: Artificial Sequence
<220> FEATURE:
<223> OTHER INFORMATION: A synthetic Hu56V4-Fc

<400> SEQUENCE: 50

Gln Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Arg Arg
             20                  25                  30

Cys Met Ala Trp Phe Arg Gln Ala Pro Gly Lys Gly Leu Glu Arg Val
```

```
            35                  40                  45
Ala Lys Leu Leu Thr Thr Ser Gly Ser Thr Tyr Leu Ala Asp Ser Val
 50                  55                  60

Lys Gly Arg Phe Thr Ile Ser Arg Asp Asn Ser Lys Asn Thr Val Tyr
 65                  70                  75                  80

Leu Gln Met Asn Ser Leu Arg Ala Glu Asp Thr Ala Val Tyr Tyr Cys
                 85                  90                  95

Ala Ala Asp Ser Phe Glu Asp Pro Thr Cys Thr Leu Val Thr Ser Ser
                100                 105                 110

Gly Ala Phe Gln Tyr Trp Gly Gln Gly Thr Leu Val Thr Val Ser Ser
                115                 120                 125

Glu Pro Lys Ser Cys Asp Lys Thr His Thr Cys Pro Pro Cys Pro Ala
130                 135                 140

Pro Glu Leu Leu Gly Gly Pro Ser Val Phe Leu Phe Pro Pro Lys Pro
145                 150                 155                 160

Lys Asp Thr Leu Met Ile Ser Arg Thr Pro Glu Val Thr Cys Val Val
                165                 170                 175

Val Asp Val Ser His Glu Asp Pro Glu Val Lys Phe Asn Trp Tyr Val
                180                 185                 190

Asp Gly Val Glu Val His Asn Ala Lys Thr Lys Pro Arg Glu Glu Gln
                195                 200                 205

Tyr Asn Ser Thr Tyr Arg Val Val Ser Val Leu Thr Val Leu His Gln
                210                 215                 220

Asp Trp Leu Asn Gly Lys Glu Tyr Lys Cys Lys Val Ser Asn Lys Ala
225                 230                 235                 240

Leu Pro Ala Pro Ile Glu Lys Thr Ile Ser Lys Ala Lys Gly Gln Pro
                245                 250                 255

Arg Glu Pro Gln Val Tyr Thr Leu Pro Pro Ser Arg Asp Glu Leu Thr
                260                 265                 270

Lys Asn Gln Val Ser Leu Thr Cys Leu Val Lys Gly Phe Tyr Pro Ser
                275                 280                 285

Asp Ile Ala Val Glu Trp Glu Ser Asn Gly Gln Pro Glu Asn Asn Tyr
290                 295                 300

Lys Thr Thr Pro Pro Val Leu Asp Ser Asp Gly Ser Phe Phe Leu Tyr
305                 310                 315                 320

Ser Lys Leu Thr Val Asp Lys Ser Arg Trp Gln Gln Gly Asn Val Phe
                325                 330                 335

Ser Cys Ser Val Met His Glu Ala Leu His Asn His Tyr Thr Gln Lys
                340                 345                 350

Ser Leu Ser Leu Ser Pro Gly Lys
                355                 360

<210> SEQ ID NO 51
<211> LENGTH: 360
<212> TYPE: PRT
<213> ORGANISM: Artificial Sequence
<220> FEATURE:
<223> OTHER INFORMATION: A synthetic Hu56V5-Fc

<400> SEQUENCE: 51

Gln Val Gln Leu Val Glu Ser Gly Gly Gly Leu Val Gln Pro Gly Gly
 1               5                  10                  15

Ser Leu Arg Leu Ser Cys Ala Ala Ser Gly Lys Met Ser Ser Arg Arg
                20                  25                  30

Cys Met Ala Trp Phe Arg Gln Ala Pro Gly Lys Glu Arg Glu Arg Val
```

```
                35                  40                  45
Ala Lys Leu Leu Thr Thr Ser Gly Ser Thr Tyr Leu Ala Asp Ser Val
 50                  55                  60

Lys Gly Arg Phe Thr Ile Ser Arg Asp Asn Ser Lys Asn Thr Val Tyr
 65                  70                  75                  80

Leu Gln Met Asn Ser Leu Lys Ala Glu Asp Thr Ala Val Tyr Tyr Cys
                 85                  90                  95

Ala Ala Asp Ser Phe Glu Asp Pro Thr Cys Thr Leu Val Thr Ser Ser
                100                 105                 110

Gly Ala Phe Gln Tyr Trp Gly Gln Gly Thr Leu Val Thr Val Ser Ser
                115                 120                 125

Glu Pro Lys Ser Cys Asp Lys Thr His Thr Cys Pro Pro Cys Pro Ala
130                 135                 140

Pro Glu Leu Leu Gly Gly Pro Ser Val Phe Leu Phe Pro Pro Lys Pro
145                 150                 155                 160

Lys Asp Thr Leu Met Ile Ser Arg Thr Pro Glu Val Thr Cys Val Val
                165                 170                 175

Val Asp Val Ser His Glu Asp Pro Glu Val Lys Phe Asn Trp Tyr Val
                180                 185                 190

Asp Gly Val Glu Val His Asn Ala Lys Thr Lys Pro Arg Glu Glu Gln
                195                 200                 205

Tyr Asn Ser Thr Tyr Arg Val Val Ser Val Leu Thr Val Leu His Gln
                210                 215                 220

Asp Trp Leu Asn Gly Lys Glu Tyr Lys Cys Lys Val Ser Asn Lys Ala
225                 230                 235                 240

Leu Pro Ala Pro Ile Glu Lys Thr Ile Ser Lys Ala Lys Gly Gln Pro
                245                 250                 255

Arg Glu Pro Gln Val Tyr Thr Leu Pro Pro Ser Arg Asp Glu Leu Thr
                260                 265                 270

Lys Asn Gln Val Ser Leu Thr Cys Leu Val Lys Gly Phe Tyr Pro Ser
                275                 280                 285

Asp Ile Ala Val Glu Trp Glu Ser Asn Gly Gln Pro Glu Asn Asn Tyr
290                 295                 300

Lys Thr Thr Pro Pro Val Leu Asp Ser Asp Gly Ser Phe Phe Leu Tyr
305                 310                 315                 320

Ser Lys Leu Thr Val Asp Lys Ser Arg Trp Gln Gln Gly Asn Val Phe
                325                 330                 335

Ser Cys Ser Val Met His Glu Ala Leu His Asn His Tyr Thr Gln Lys
                340                 345                 350

Ser Leu Ser Leu Ser Pro Gly Lys
                355                 360

<210> SEQ ID NO 52
<211> LENGTH: 448
<212> TYPE: PRT
<213> ORGANISM: Artificial Sequence
<220> FEATURE:
<223> OTHER INFORMATION: A synthetic human PDL1-Fc

<400> SEQUENCE: 52

Thr Val Thr Val Pro Lys Asp Leu Tyr Val Val Glu Tyr Gly Ser Asn
 1               5                  10                  15

Met Thr Ile Glu Cys Lys Phe Pro Val Glu Lys Gln Leu Asp Leu Ala
                 20                  25                  30

Ala Leu Ile Val Tyr Trp Glu Met Glu Asp Lys Asn Ile Ile Gln Phe
```

```
            35                  40                  45
Val His Gly Glu Glu Asp Leu Lys Val Gln His Ser Ser Tyr Arg Gln
 50                  55                  60

Arg Ala Arg Leu Leu Lys Asp Gln Leu Ser Leu Gly Asn Ala Ala Leu
 65                  70                  75                  80

Gln Ile Thr Asp Val Lys Leu Gln Asp Ala Gly Val Tyr Arg Cys Met
                 85                  90                  95

Ile Ser Tyr Gly Gly Ala Asp Tyr Lys Arg Ile Thr Val Lys Val Asn
                100                 105                 110

Ala Pro Tyr Asn Lys Ile Asn Gln Arg Ile Leu Val Val Asp Pro Val
            115                 120                 125

Thr Ser Glu His Glu Leu Thr Cys Gln Ala Glu Gly Tyr Pro Lys Ala
130                 135                 140

Glu Val Ile Trp Thr Ser Ser Asp His Gln Val Leu Ser Gly Lys Thr
145                 150                 155                 160

Thr Thr Thr Asn Ser Lys Arg Glu Glu Asn Leu Phe Asn Val Thr Ser
                165                 170                 175

Thr Leu Arg Ile Asn Thr Thr Asn Glu Ile Phe Tyr Cys Thr Phe
                180                 185                 190

Arg Arg Leu Asp Pro Glu Glu Asn His Thr Ala Glu Leu Val Ile Pro
            195                 200                 205

Glu Leu Pro Leu Ala His Pro Pro Asn Glu Arg Thr Asp Asp Lys Thr
210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
                260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
                340                 345                 350

Pro Pro Ser Arg Asp Glu Leu Thr Lys Asn Gln Val Ser Leu Thr Cys
            355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
                420                 425                 430

Leu His Asn His Tyr Thr Gln Lys Ser Leu Ser Leu Ser Pro Gly Lys
            435                 440                 445

<210> SEQ ID NO 53
```

```
<211> LENGTH: 448
<212> TYPE: PRT
<213> ORGANISM: Artificial Sequence
<220> FEATURE:
<223> OTHER INFORMATION: A synthetic mouse PDL1-Fc

<400> SEQUENCE: 53
```

Phe Thr Ile Thr Ala Pro Lys Asp Leu Tyr Val Glu Tyr Gly Ser
1               5                   10                  15

Asn Val Thr Met Glu Cys Arg Phe Pro Val Glu Arg Glu Leu Asp Leu
            20                  25                  30

Leu Ala Leu Val Val Tyr Trp Glu Lys Glu Asp Glu Gln Val Ile Gln
        35                  40                  45

Phe Val Ala Gly Glu Glu Asp Leu Lys Pro Gln His Ser Asn Phe Arg
    50                  55                  60

Gly Arg Ala Ser Leu Pro Lys Asp Gln Leu Leu Lys Gly Asn Ala Ala
65                  70                  75                  80

Leu Gln Ile Thr Asp Val Lys Leu Gln Asp Ala Gly Val Tyr Cys Cys
                85                  90                  95

Ile Ile Ser Tyr Gly Gly Ala Asp Tyr Lys Arg Ile Thr Leu Lys Val
            100                 105                 110

Asn Ala Pro Tyr Arg Lys Ile Asn Gln Arg Ile Ser Val Asp Pro Ala
        115                 120                 125

Thr Ser Glu His Glu Leu Ile Cys Gln Ala Glu Gly Tyr Pro Glu Ala
    130                 135                 140

Glu Val Ile Trp Thr Asn Ser Asp His Gln Pro Val Ser Gly Lys Arg
145                 150                 155                 160

Ser Val Thr Thr Ser Arg Thr Glu Gly Met Leu Leu Asn Val Thr Ser
                165                 170                 175

Ser Leu Arg Val Asn Ala Thr Ala Asn Asp Val Phe Tyr Cys Thr Phe
            180                 185                 190

Trp Arg Ser Gln Pro Gly Gln Asn His Thr Ala Glu Leu Ile Ile Pro
        195                 200                 205

Glu Leu Pro Ala Thr His Pro Pro Gln Asn Arg Thr His Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

```
Asn Gly Gln Pro Glu Asn Asn Tyr Lys Thr Thr Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 54
<211> LENGTH: 374
<212> TYPE: PRT
<213> ORGANISM: Artificial Sequence
<220> FEATURE:
<223> OTHER INFORMATION: A synthetic human PD1-Fc

<400> SEQUENCE: 54

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Ser Phe Val Leu Asn Trp Tyr
        35                  40                  45

Arg Met Ser Pro Ser Asn Gln Thr Asp Lys Leu Ala Ala Phe Pro Glu
    50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Gly Ala Ile Ser Leu Ala Pro Lys Ala
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Asp Lys Thr His Thr Cys Pro Pro Cys Pro Ala Pro Glu
145                 150                 155                 160

Leu Leu Gly Gly Pro Ser Val Phe Leu Phe Pro Pro Lys Pro Lys Asp
                165                 170                 175

Thr Leu Met Ile Ser Arg Thr Pro Glu Val Thr Cys Val Val Val Asp
            180                 185                 190

Val Ser His Glu Asp Pro Glu Val Lys Phe Asn Trp Tyr Val Asp Gly
        195                 200                 205

Val Glu Val His Asn Ala Lys Thr Lys Pro Arg Glu Glu Gln Tyr Asn
    210                 215                 220

Ser Thr Tyr Arg Val Val Ser Val Leu Thr Val Leu His Gln Asp Trp
225                 230                 235                 240

Leu Asn Gly Lys Glu Tyr Lys Cys Lys Val Ser Asn Lys Ala Leu Pro
                245                 250                 255

Ala Pro Ile Glu Lys Thr Ile Ser Lys Ala Lys Gly Gln Pro Arg Glu
            260                 265                 270

Pro Gln Val Tyr Thr Leu Pro Pro Ser Arg Asp Glu Leu Thr Lys Asn
        275                 280                 285

Gln Val Ser Leu Thr Cys Leu Val Lys Gly Phe Tyr Pro Ser Asp Ile
    290                 295                 300
```

Ala Val Glu Trp Glu Ser Asn Gly Gln Pro Glu Asn Tyr Lys Thr
305                 310                 315                 320

Thr Pro Pro Val Leu Asp Ser Asp Gly Ser Phe Phe Leu Tyr Ser Lys
                325                 330                 335

Leu Thr Val Asp Lys Ser Arg Trp Gln Gln Gly Asn Val Phe Ser Cys
                340                 345                 350

Ser Val Met His Glu Ala Leu His Asn His Tyr Thr Gln Lys Ser Leu
        355                 360                 365

Ser Leu Ser Pro Gly Lys
    370

<210> SEQ ID NO 55
<211> LENGTH: 231
<212> TYPE: PRT
<213> ORGANISM: Artificial Sequence
<220> FEATURE:
<223> OTHER INFORMATION: A synthetic PDL1-Chis

<400> SEQUENCE: 55

Thr Val Thr Val Pro Lys Asp Leu Tyr Val Val Glu Tyr Gly Ser Asn
1               5                   10                  15

Met Thr Ile Glu Cys Lys Phe Pro Val Glu Lys Gln Leu Asp Leu Ala
            20                  25                  30

Ala Leu Ile Val Tyr Trp Glu Met Glu Asp Lys Asn Ile Ile Gln Phe
        35                  40                  45

Val His Gly Glu Glu Asp Leu Lys Val Gln His Ser Ser Tyr Arg Gln
    50                  55                  60

Arg Ala Arg Leu Leu Lys Asp Gln Leu Ser Leu Gly Asn Ala Ala Leu
65                  70                  75                  80

Gln Ile Thr Asp Val Lys Leu Gln Asp Ala Gly Val Tyr Arg Cys Met
                85                  90                  95

Ile Ser Tyr Gly Gly Ala Asp Tyr Lys Arg Ile Thr Val Lys Val Asn
            100                 105                 110

Ala Pro Tyr Asn Lys Ile Asn Gln Arg Ile Leu Val Val Asp Pro Val
        115                 120                 125

Thr Ser Glu His Glu Leu Thr Cys Gln Ala Glu Gly Tyr Pro Lys Ala
    130                 135                 140

Glu Val Ile Trp Thr Ser Ser Asp His Gln Val Leu Ser Gly Lys Thr
145                 150                 155                 160

Thr Thr Thr Asn Ser Lys Arg Glu Glu Asn Leu Phe Asn Val Thr Ser
                165                 170                 175

Thr Leu Arg Ile Asn Thr Thr Asn Glu Ile Phe Tyr Cys Thr Phe
            180                 185                 190

Arg Arg Leu Asp Pro Glu Glu Asn His Thr Ala Glu Leu Val Ile Pro
        195                 200                 205

Glu Leu Pro Leu Ala His Pro Pro Asn Glu Arg Thr Asp Gly Ser His
    210                 215                 220

His His His His His His
225                 230

<210> SEQ ID NO 56
<211> LENGTH: 435
<212> TYPE: PRT
<213> ORGANISM: Artificial Sequence
<220> FEATURE:
<223> OTHER INFORMATION: A synthetic CD80-Chis

```
<400> SEQUENCE: 56

Val Ile His Val Thr Lys Glu Val Glu Val Ala Thr Leu Ser Cys
1               5                   10                  15

Gly His Asn Val Ser Val Glu Glu Leu Ala Gln Thr Arg Ile Tyr Trp
                20                  25                  30

Gln Lys Glu Lys Lys Met Val Leu Thr Met Met Ser Gly Asp Met Asn
            35                  40                  45

Ile Trp Pro Glu Tyr Lys Asn Arg Thr Ile Phe Asp Ile Thr Asn Asn
    50                  55                  60

Leu Ser Ile Val Ile Leu Ala Leu Arg Pro Ser Asp Glu Gly Thr Tyr
65                  70                  75                  80

Glu Cys Val Val Leu Lys Tyr Glu Lys Asp Ala Phe Lys Arg Glu His
                85                  90                  95

Leu Ala Glu Val Thr Leu Ser Val Lys Ala Asp Phe Pro Thr Pro Ser
            100                 105                 110

Ile Ser Asp Phe Glu Ile Pro Thr Ser Asn Ile Arg Arg Ile Ile Cys
        115                 120                 125

Ser Thr Ser Gly Gly Phe Pro Glu Pro His Leu Ser Trp Leu Glu Asn
130                 135                 140

Gly Glu Glu Leu Asn Ala Ile Asn Thr Thr Val Ser Gln Asp Pro Glu
145                 150                 155                 160

Thr Glu Leu Tyr Ala Val Ser Ser Lys Leu Asp Phe Asn Met Thr Thr
                165                 170                 175

Asn His Ser Phe Met Cys Leu Ile Lys Tyr Gly His Leu Arg Val Asn
            180                 185                 190

Gln Thr Phe Asn Trp Asn Thr Thr Lys Gln Glu His Phe Pro Asp Asn
        195                 200                 205

Asp Lys Thr His Thr Cys Pro Pro Cys Pro Ala Pro Glu Leu Leu Gly
    210                 215                 220

Gly Pro Ser Val Phe Leu Phe Pro Pro Lys Pro Lys Asp Thr Leu Met
225                 230                 235                 240

Ile Ser Arg Thr Pro Glu Val Thr Cys Val Val Val Asp Val Ser His
                245                 250                 255

Glu Asp Pro Glu Val Lys Phe Asn Trp Tyr Val Asp Gly Val Glu Val
            260                 265                 270

His Asn Ala Lys Thr Lys Pro Arg Glu Glu Gln Tyr Asn Ser Thr Tyr
        275                 280                 285

Arg Val Val Ser Val Leu Thr Val Leu His Gln Asp Trp Leu Asn Gly
    290                 295                 300

Lys Glu Tyr Lys Cys Lys Val Ser Asn Lys Ala Leu Pro Ala Pro Ile
305                 310                 315                 320

Glu Lys Thr Ile Ser Lys Ala Lys Gly Gln Pro Arg Glu Pro Gln Val
                325                 330                 335

Tyr Thr Leu Pro Pro Ser Arg Asp Glu Leu Thr Lys Asn Gln Val Ser
            340                 345                 350

Leu Thr Cys Leu Val Lys Gly Phe Tyr Pro Ser Asp Ile Ala Val Glu
        355                 360                 365

Trp Glu Ser Asn Gly Gln Pro Glu Asn Asn Tyr Lys Thr Thr Pro Pro
    370                 375                 380

Val Leu Asp Ser Asp Gly Ser Phe Phe Leu Tyr Ser Lys Leu Thr Val
385                 390                 395                 400

Asp Lys Ser Arg Trp Gln Gln Gly Asn Val Phe Ser Cys Ser Val Met
                405                 410                 415
```

```
His Glu Ala Leu His Asn His Tyr Thr Gln Lys Ser Leu Ser Leu Ser
            420                 425                 430

Pro Gly Lys
        435

<210> SEQ ID NO 57
<211> LENGTH: 272
<212> TYPE: PRT
<213> ORGANISM: Artificial Sequence
<220> FEATURE:
<223> OTHER INFORMATION: A synthetic monkey PDL1

<400> SEQUENCE: 57

Phe Thr Val Thr Val Pro Lys Asp Leu Tyr Val Val Glu Tyr Gly Ser
1               5                   10                  15

Asn Met Thr Ile Glu Cys Lys Phe Pro Val Lys Gln Leu Asp Leu
            20                  25                  30

Thr Ser Leu Ile Val Tyr Trp Glu Met Glu Asp Lys Asn Ile Ile Gln
        35                  40                  45

Phe Val His Gly Glu Glu Asp Leu Lys Val Gln His Ser Asn Tyr Arg
    50                  55                  60

Gln Arg Ala Gln Leu Leu Lys Asp Gln Leu Ser Leu Gly Asn Ala Ala
65                  70                  75                  80

Leu Arg Ile Thr Asp Val Lys Leu Gln Asp Ala Gly Val Tyr Arg Cys
                85                  90                  95

Met Ile Ser Tyr Gly Gly Ala Asp Tyr Lys Arg Ile Thr Val Lys Val
            100                 105                 110

Asn Ala Pro Tyr Asn Lys Ile Asn Gln Arg Ile Leu Val Val Asp Pro
        115                 120                 125

Val Thr Ser Glu His Glu Leu Thr Cys Gln Ala Glu Gly Tyr Pro Lys
    130                 135                 140

Ala Glu Val Ile Trp Thr Ser Ser Asp His Gln Val Leu Ser Gly Lys
145                 150                 155                 160

Thr Thr Thr Thr Asn Ser Lys Arg Glu Glu Lys Leu Leu Asn Val Thr
                165                 170                 175

Ser Thr Leu Arg Ile Asn Thr Thr Ala Asn Glu Ile Phe Tyr Cys Ile
            180                 185                 190

Phe Arg Arg Leu Asp Pro Glu Glu Asn His Thr Ala Glu Leu Val Ile
        195                 200                 205

Pro Glu Leu Pro Leu Ala Leu Pro Pro Asn Glu Arg Thr His Leu Val
    210                 215                 220

Ile Leu Gly Ala Ile Phe Leu Leu Gly Val Ala Leu Thr Phe Ile
225                 230                 235                 240

Phe Tyr Leu Arg Lys Gly Arg Met Met Asp Met Lys Lys Ser Gly Ile
                245                 250                 255

Arg Val Thr Asn Ser Lys Lys Gln Arg Asp Thr Gln Leu Glu Glu Thr
            260                 265                 270

<210> SEQ ID NO 58
<211> LENGTH: 372
<212> TYPE: DNA
<213> ORGANISM: Artificial Sequence
<220> FEATURE:
<223> OTHER INFORMATION: A synthetic antibody No.10

<400> SEQUENCE: 58
caggtgcagc tgcaggagtc tgggggaggc tcggtgcagg ctggagggtc tctgcgactc    60
```

```
tcctgtgcag cctctggaaa cattgttagt agctactgta tgggctggtt ccgacaggct    120
ccagggaaag agcgcgtggg ggtcgccgct attgatagtg atggtaccac aaaatacgca    180
gactccatga agggccgatt caccatctcc aaagacaacg ccaagaacac tctagatctc    240
caaatgaaca gcctgaaacc tgaggacact gccatgtact actgtgtggc acgtttgaac    300
tgccccggac cagttgattg ggtcccgatg ttcccttaca ggggccaggg gacccaggtc    360
accgtctcct ca                                                        372
```

<210> SEQ ID NO 59
<211> LENGTH: 384
<212> TYPE: DNA
<213> ORGANISM: Artificial Sequence
<220> FEATURE:
<223> OTHER INFORMATION: A synthetic antibody No.27

<400> SEQUENCE: 59

```
caggtgcagc tgcaggagtc tggaggaggc tcggtgcagg ctggagggtc tctgagactc     60
tcctgtgcag cctctggaaa catcagcagt aggcgatgta tggcctggtt ccgccaggct    120
ccagggaagg agcgcgaaag agtcgcgaac attctaacta ctactggtaa cacatacttg    180
gccgactccg tgaagggccg attcaccatc tcccaaaaca cgccaagag cacggtgtat    240 ctgcaaatga acagcctgaa acctgaggac actgccatgt actgtgcggc agattctttt    300
ttccatgatc cgacttgtac ggtggtagct agttcgggg cctttcagta ctggggccag    360
gggacccagg tcaccgtctc ctca                                          384
```

<210> SEQ ID NO 60
<211> LENGTH: 375
<212> TYPE: DNA
<213> ORGANISM: Artificial Sequence
<220> FEATURE:
<223> OTHER INFORMATION: A synthetic antibody No.38

<400> SEQUENCE: 60

```
caggtgcagc tgcaggagtc tggaggaggc tcggtgcagg ctggagggtc tctgagactc     60
tcctgtgcag tatctggttt catcagcagt aggcgatgta tgggctggtt ccgacaggct    120
ccagggaagg agcgcgtggg ggtcgcgaac attactggta ctggtaacac atacttggcc    180
gactccgtga agggccgatt caccatctcc caaaacaacg ccaagagcac ggtgtatctg    240
caaatgaaca gcctgaaacc tgaggacact gccatgtact actgtgcggc agattctttc    300
ccgacttgta cggtggtagc tagttcgggg cctttcagt actggggcca ggggacccag    360
gtcaccgtct cctca                                                    375
```

<210> SEQ ID NO 61
<211> LENGTH: 384
<212> TYPE: DNA
<213> ORGANISM: Artificial Sequence
<220> FEATURE:
<223> OTHER INFORMATION: A synthetic antibody No.56

<400> SEQUENCE: 61

```
caggtgcagc tgcaggagtc tgggggaggc ttggtgcagc ctgggggggtc cctgagactc     60 tcctgtgcag cctctggaaa gatgtccagt aggcgatgta tggcctggtt ccgccaggct    120
ccagggaagg agcgcgaaag ggtcgcgaag ctgcttacta ctagtggtag cacatacttg    180
gccgactccg tgaagggccg attcaccatc tcccaaaaca cgccaagagc cacggtgtat    240
```

```
ctgcaaatga atagcctgaa acctgaggac actgccatgt actactgtgc ggcagattct      300
ttcgaagatc ctacttgtac gctagtaact agttcggggg cctttcagta ctggggccag      360
gggacccagg tcaccgtctc ctca                                             384
```

```
<210> SEQ ID NO 62
<211> LENGTH: 384
<212> TYPE: DNA
<213> ORGANISM: Artificial Sequence
<220> FEATURE:
<223> OTHER INFORMATION: A synthetic antibody No.69

<400> SEQUENCE: 62
```

```
caggtgcagc tgcaggagtc tggaggaggc tcggtgcagg ctggagggtc tctgagactc       60
tcctgtgcag ttcaacgaaa catcagcagt agctactgta tggcctggtt ccgccaggct      120
ccagggaagc agcgcgaaag agtcgataag attctaacta ctccaggtaa cacatacttg      180
gccgactccg tgaagggccg attcaccatc tcccaaaaca cgccaagag cacggtgtat       240 ctgcaaatga acagcctgaa acctgaggac actgccatgt actactgtgc ggcagattct      300
ttccaaaagc cgacttgtac ggtggtagct tcttggccag cctttcagta ctggggccag      360
gggacccagg tcaccgtctc ctca                                             384
```

```
<210> SEQ ID NO 63
<211> LENGTH: 384
<212> TYPE: DNA
<213> ORGANISM: Artificial Sequence
<220> FEATURE:
<223> OTHER INFORMATION: A synthetic antibody No.81

<400> SEQUENCE: 63
```

```
caggtgcagc tgcaggagtc tggggggaggc tcggtgcagg ctggagggtc tctgagactc      60
tcctgtgcag cctctggaaa catcattcgt gtgcgatgta tggcctggtt ccgccaggct      120
ccagggaagg agcgcgaaag aggcccgaac attctaacta ctactattag cacatacttg      180
gccgactccg tgaagggccg attcaccatc tcccaaaaca cgccaagag cacggtgtat       240 ctgcaaatga acagcctgaa acctgaggac actgccatgt actactgtgc ggcagattct      300
ttcggttatc cgacttgccc cggaccagct agttcggggg cctttcagta ctggggccag      360
gggacccagg tcaccgtctc ctca                                             384
```

```
<210> SEQ ID NO 64
<211> LENGTH: 387
<212> TYPE: DNA
<213> ORGANISM: Artificial Sequence
<220> FEATURE:
<223> OTHER INFORMATION: A synthetic antibody No.87

<400> SEQUENCE: 64
```

```
caggtgcagc tgcaggagtc tggggggaggc tcggtgcagg ctggagggtc tctgaaactc      60
tcctgtgcag cctctggata catcttcagt agctgcggaa tgggctggta ccgccaggct      120
ccagggaagg agcgcgagtt ggtctcaact attagtagtg atggtaccac aagctatgca      180
gactccgtga agggccgatt caccatctcc aagacaatg ccaagaacac gctgtatctg       240
caaatgaaca gcctgaaaac tgaggacacg gccgtgtatt actgtgtggc agattgtcca      300
cccataccgg aatttacaag ttgtagtggt ggttactgct tgagtggcga ctactggggc      360
caggggaccc aggtcaccgt ctcctca                                          387
```

```
<210> SEQ ID NO 65
<211> LENGTH: 372
<212> TYPE: DNA
<213> ORGANISM: Artificial Sequence
<220> FEATURE:
<223> OTHER INFORMATION: A synthetic antibody No.94

<400> SEQUENCE: 65
caggtgcagc tgcaggagtc tgggggaggc tcggtgcagg ctggagggtc tctgagactc      60
tcctgtgcag cctctctaaa tattttagt agctactgta tgggctggtt ccgccaggct     120
ccagggaagc agcgcgtggg ggtcgcgact attgatagtg atggtactac aagatacgta     180
gactccgtga agggccgatt caccatctcc aagacaacg ccaagaacac tctagatctc     240
caaatgaaca gcctgaaacc tgaggacact gccatgtact actgtgcggc acgtttgaac     300
tgccccgggc cagttgattg ggtcccgatg tttccttaca ggggccaggg gacccaggtc     360
accgtctcct ca                                                       372

<210> SEQ ID NO 66
<211> LENGTH: 24
<212> TYPE: DNA
<213> ORGANISM: Artificial Sequence
<220> FEATURE:
<223> OTHER INFORMATION: A synthetic first round PCR primer Forward

<400> SEQUENCE: 66
gtcctggctg ctcttctaca aggc                                            24

<210> SEQ ID NO 67
<211> LENGTH: 23
<212> TYPE: DNA
<213> ORGANISM: Artificial Sequence
<220> FEATURE:
<223> OTHER INFORMATION: A synthetic first round PCR primer Reverse

<400> SEQUENCE: 67
ggtacgtgct gttgaactgt tcc                                             23

<210> SEQ ID NO 68
<211> LENGTH: 29
<212> TYPE: DNA
<213> ORGANISM: Artificial Sequence
<220> FEATURE:
<223> OTHER INFORMATION: A synthetic second round PCR primer Forward

<400> SEQUENCE: 68
gatgtgcagc tgcaggagtc tggrggagg                                       29

<210> SEQ ID NO 69
<211> LENGTH: 35
<212> TYPE: DNA
<213> ORGANISM: Artificial Sequence
<220> FEATURE:
<223> OTHER INFORMATION: A synthetic second round PCR primer Reverse

<400> SEQUENCE: 69
ggactagtgc ggccgctgga gacggtgacc tgggt                                35

<210> SEQ ID NO 70
<211> LENGTH: 232
<212> TYPE: PRT
<213> ORGANISM: Artificial Sequence
<220> FEATURE:
<223> OTHER INFORMATION: A synthetic mutant Fc IgG1-Fc-m1
```

<400> SEQUENCE: 70

```
Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
                20                  25                  30

Lys Asp Thr Leu Met Ile Ser Arg Thr Pro Glu Val Thr Cys Val Val
            35                  40                  45

Val Ala Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Gly Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230
```

<210> SEQ ID NO 71
<211> LENGTH: 232
<212> TYPE: PRT
<213> ORGANISM: Artificial Sequence
<220> FEATURE:
<223> OTHER INFORMATION: A synthetic mutant Fc IgG1-Fc-m2

<400> SEQUENCE: 71

```
Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
                20                  25                  30

Lys Asp Thr Leu Met Ile Ser Arg Thr Pro Glu Val Thr Cys Val Val
            35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Ala Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
```

```
                115                 120                 125
Arg Glu Pro Gln Val Tyr Thr Leu Pro Pro Ser Arg Asp Glu Leu Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
                180                 185                 190

Ser Lys Leu Thr Val Asp Lys Ser Arg Trp Gln Gln Gly Asn Val Phe
                195                 200                 205

Ser Cys Ser Val Met His Glu Ala Leu His Asn His Tyr Thr Gln Lys
                210                 215                 220

Ser Leu Ser Leu Ser Pro Gly Lys
225                 230

<210> SEQ ID NO 72
<211> LENGTH: 360
<212> TYPE: PRT
<213> ORGANISM: Artificial Sequence
<220> FEATURE:
<223> OTHER INFORMATION: A synthetic 56-Fc-m2

<400> SEQUENCE: 72

Gln Val Gln Leu Gln Glu Ser Gly Gly Gly Leu Val Gln Pro Gly Gly
1               5                   10                  15

Ser Leu Arg Leu Ser Cys Ala Ala Ser Gly Lys Met Ser Ser Arg Arg
                20                  25                  30

Cys Met Ala Trp Phe Arg Gln Ala Pro Gly Lys Glu Arg Glu Arg Val
                35                  40                  45

Ala Lys Leu Leu Thr Thr Ser Gly Ser Thr Tyr Leu Ala Asp Ser Val
                50                  55                  60

Lys Gly Arg Phe Thr Ile Ser Gln Asn Asn Ala Lys Ser Thr Val Tyr
65                  70                  75                  80

Leu Gln Met Asn Ser Leu Lys Pro Glu Asp Thr Ala Met Tyr Tyr Cys
                85                  90                  95

Ala Ala Asp Ser Phe Glu Asp Pro Thr Cys Thr Leu Val Thr Ser Ser
                100                 105                 110

Gly Ala Phe Gln Tyr Trp Gly Gln Gly Thr Gln Val Thr Val Ser Ser
                115                 120                 125

Glu Pro Lys Ser Ser Asp Lys Thr His Thr Cys Pro Pro Cys Pro Ala
                130                 135                 140

Pro Glu Leu Leu Gly Gly Pro Ser Val Phe Leu Phe Pro Pro Lys Pro
145                 150                 155                 160

Lys Asp Thr Leu Met Ile Ser Arg Thr Pro Glu Val Thr Cys Val Val
                165                 170                 175

Val Asp Val Ser His Glu Asp Pro Glu Val Lys Phe Asn Trp Tyr Val
                180                 185                 190

Asp Gly Val Glu Val His Asn Ala Lys Thr Lys Pro Arg Glu Glu Gln
                195                 200                 205

Tyr Ala Ser Thr Tyr Arg Val Val Ser Val Leu Thr Val Leu His Gln
                210                 215                 220

Asp Trp Leu Asn Gly Lys Glu Tyr Lys Cys Lys Val Ser Asn Lys Ala
225                 230                 235                 240

Leu Pro Ala Pro Ile Glu Lys Thr Ile Ser Lys Ala Lys Gly Gln Pro
```

```
                        245                 250                 255
Arg Glu Pro Gln Val Tyr Thr Leu Pro Pro Ser Arg Asp Glu Leu Thr
                260                 265                 270

Lys Asn Gln Val Ser Leu Thr Cys Leu Val Lys Gly Phe Tyr Pro Ser
            275                 280                 285

Asp Ile Ala Val Glu Trp Glu Ser Asn Gly Gln Pro Glu Asn Asn Tyr
        290                 295                 300

Lys Thr Thr Pro Pro Val Leu Asp Ser Asp Gly Ser Phe Phe Leu Tyr
305                 310                 315                 320

Ser Lys Leu Thr Val Asp Lys Ser Arg Trp Gln Gln Gly Asn Val Phe
                325                 330                 335

Ser Cys Ser Val Met His Glu Ala Leu His Asn His Tyr Thr Gln Lys
                340                 345                 350

Ser Leu Ser Leu Ser Pro Gly Lys
            355                 360

<210> SEQ ID NO 73
<211> LENGTH: 360
<212> TYPE: PRT
<213> ORGANISM: Artificial Sequence
<220> FEATURE:
<223> OTHER INFORMATION: A synthetic Hu56V1-Fc-m2

<400> SEQUENCE: 73

Gln Val Gln Leu Val Glu Ser Gly Gly Gly Leu Val Gln Pro Gly Gly
1               5                   10                  15

Ser Leu Arg Leu Ser Cys Ala Ala Ser Gly Lys Met Ser Ser Arg Arg
            20                  25                  30

Cys Met Ala Trp Phe Arg Gln Ala Pro Gly Lys Glu Arg Glu Arg Val
        35                  40                  45

Ala Lys Leu Leu Thr Thr Ser Gly Ser Thr Tyr Leu Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Ala Glu Asp Thr Ala Val Tyr Tyr Cys
                85                  90                  95

Ala Ala Asp Ser Phe Glu Asp Pro Thr Cys Thr Leu Val Thr Ser Ser
            100                 105                 110

Gly Ala Phe Gln Tyr Trp Gly Gln Gly Thr Leu Val Thr Val Ser Ser
        115                 120                 125

Glu Pro Lys Ser Ser Asp Lys Thr His Thr Cys Pro Pro Cys Pro Ala
    130                 135                 140

Pro Glu Leu Leu Gly Gly Pro Ser Val Phe Leu Phe Pro Pro Lys Pro
145                 150                 155                 160

Lys Asp Thr Leu Met Ile Ser Arg Thr Pro Glu Val Thr Cys Val Val
                165                 170                 175

Val Asp Val Ser His Glu Asp Pro Glu Val Lys Phe Asn Trp Tyr Val
            180                 185                 190

Asp Gly Val Glu Val His Asn Ala Lys Thr Lys Pro Arg Glu Glu Gln
        195                 200                 205

Tyr Ala Ser Thr Tyr Arg Val Val Ser Val Leu Thr Val Leu His Gln
    210                 215                 220

Asp Trp Leu Asn Gly Lys Glu Tyr Lys Cys Lys Val Ser Asn Lys Ala
225                 230                 235                 240

Leu Pro Ala Pro Ile Glu Lys Thr Ile Ser Lys Ala Lys Gly Gln Pro
```

```
                    245                 250                 255
Arg Glu Pro Gln Val Tyr Thr Leu Pro Pro Ser Arg Asp Glu Leu Thr
                260                 265                 270

Lys Asn Gln Val Ser Leu Thr Cys Leu Val Lys Gly Phe Tyr Pro Ser
            275                 280                 285

Asp Ile Ala Val Glu Trp Glu Ser Asn Gly Gln Pro Glu Asn Asn Tyr
        290                 295                 300

Lys Thr Thr Pro Pro Val Leu Asp Ser Asp Gly Ser Phe Phe Leu Tyr
305                 310                 315                 320

Ser Lys Leu Thr Val Asp Lys Ser Arg Trp Gln Gln Gly Asn Val Phe
                325                 330                 335

Ser Cys Ser Val Met His Glu Ala Leu His Asn His Tyr Thr Gln Lys
            340                 345                 350

Ser Leu Ser Leu Ser Pro Gly Lys
        355                 360

<210> SEQ ID NO 74
<211> LENGTH: 360
<212> TYPE: PRT
<213> ORGANISM: Artificial Sequence
<220> FEATURE:
<223> OTHER INFORMATION: A synthetic Hu56V2-Fc-m2

<400> SEQUENCE: 74

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Arg
            20                  25                  30

Cys Met Ala Trp Phe Arg Gln Ala Pro Gly Lys Glu Arg Glu Arg Val
        35                  40                  45

Ala Lys Leu Leu Thr Thr Ser Gly Ser Thr Tyr Leu Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Ala Glu Asp Thr Ala Val Tyr Tyr Cys
                85                  90                  95

Ala Ala Asp Ser Phe Glu Asp Pro Thr Cys Thr Leu Val Thr Ser Ser
            100                 105                 110

Gly Ala Phe Gln Tyr Trp Gly Gln Gly Thr Leu Val Thr Val Ser Ser
        115                 120                 125

Glu Pro Lys Ser Ser Asp Lys Thr His Thr Cys Pro Pro Cys Pro Ala
    130                 135                 140

Pro Glu Leu Leu Gly Gly Pro Ser Val Phe Leu Phe Pro Pro Lys Pro
145                 150                 155                 160

Lys Asp Thr Leu Met Ile Ser Arg Thr Pro Glu Val Thr Cys Val Val
                165                 170                 175

Val Asp Val Ser His Glu Asp Pro Glu Val Lys Phe Asn Trp Tyr Val
            180                 185                 190

Asp Gly Val Glu Val His Asn Ala Lys Thr Lys Pro Arg Glu Glu Gln
        195                 200                 205

Tyr Ala Ser Thr Tyr Arg Val Val Ser Val Leu Thr Val Leu His Gln
    210                 215                 220

Asp Trp Leu Asn Gly Lys Glu Tyr Lys Cys Lys Val Ser Asn Lys Ala
225                 230                 235                 240

Leu Pro Ala Pro Ile Glu Lys Thr Ile Ser Lys Ala Lys Gly Gln Pro
```

```
                    245                 250                 255
Arg Glu Pro Gln Val Tyr Thr Leu Pro Pro Ser Arg Asp Glu Leu Thr
                260                 265                 270

Lys Asn Gln Val Ser Leu Thr Cys Leu Val Lys Gly Phe Tyr Pro Ser
            275                 280                 285

Asp Ile Ala Val Glu Trp Glu Ser Asn Gly Gln Pro Glu Asn Asn Tyr
        290                 295                 300

Lys Thr Thr Pro Pro Val Leu Asp Ser Asp Gly Ser Phe Phe Leu Tyr
305                 310                 315                 320

Ser Lys Leu Thr Val Asp Lys Ser Arg Trp Gln Gln Gly Asn Val Phe
                325                 330                 335

Ser Cys Ser Val Met His Glu Ala Leu His Asn His Tyr Thr Gln Lys
            340                 345                 350

Ser Leu Ser Leu Ser Pro Gly Lys
        355                 360

<210> SEQ ID NO 75
<211> LENGTH: 360
<212> TYPE: PRT
<213> ORGANISM: Artificial Sequence
<220> FEATURE:
<223> OTHER INFORMATION: A synthetic Hu56V3-Fc-m2

<400> SEQUENCE: 75

Gln Val Gln Leu Val Glu Ser Gly Gly Gly Leu Val Gln Pro Gly Gly
1               5                   10                  15

Ser Leu Arg Leu Ser Cys Ala Ala Ser Gly Lys Met Ser Ser Arg Arg
            20                  25                  30

Cys Met Ala Trp Phe Arg Gln Ala Pro Gly Lys Gly Leu Glu Arg Val
        35                  40                  45

Ala Lys Leu Leu Thr Thr Ser Gly Ser Thr Tyr Leu Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Ala Glu Asp Thr Ala Val Tyr Tyr Cys
                85                  90                  95

Ala Ala Asp Ser Phe Glu Asp Pro Thr Cys Thr Leu Val Thr Ser Ser
            100                 105                 110

Gly Ala Phe Gln Tyr Trp Gly Gln Gly Thr Leu Val Thr Val Ser Ser
        115                 120                 125

Glu Pro Lys Ser Ser Asp Lys Thr His Thr Cys Pro Pro Cys Pro Ala
    130                 135                 140

Pro Glu Leu Leu Gly Gly Pro Ser Val Phe Leu Phe Pro Pro Lys Pro
145                 150                 155                 160

Lys Asp Thr Leu Met Ile Ser Arg Thr Pro Glu Val Thr Cys Val Val
                165                 170                 175

Val Asp Val Ser His Glu Asp Pro Glu Val Lys Phe Asn Trp Tyr Val
            180                 185                 190

Asp Gly Val Glu Val His Asn Ala Lys Thr Lys Pro Arg Glu Glu Gln
        195                 200                 205

Tyr Ala Ser Thr Tyr Arg Val Val Ser Val Leu Thr Val Leu His Gln
    210                 215                 220

Asp Trp Leu Asn Gly Lys Glu Tyr Lys Cys Lys Val Ser Asn Lys Ala
225                 230                 235                 240

Leu Pro Ala Pro Ile Glu Lys Thr Ile Ser Lys Ala Lys Gly Gln Pro
```

```
                        245                 250                 255
Arg Glu Pro Gln Val Tyr Thr Leu Pro Pro Ser Arg Asp Glu Leu Thr
                    260                 265                 270

Lys Asn Gln Val Ser Leu Thr Cys Leu Val Lys Gly Phe Tyr Pro Ser
                275                 280                 285

Asp Ile Ala Val Glu Trp Glu Ser Asn Gly Gln Pro Glu Asn Asn Tyr
            290                 295                 300

Lys Thr Thr Pro Pro Val Leu Asp Ser Asp Gly Ser Phe Phe Leu Tyr
305                 310                 315                 320

Ser Lys Leu Thr Val Asp Lys Ser Arg Trp Gln Gln Gly Asn Val Phe
                325                 330                 335

Ser Cys Ser Val Met His Glu Ala Leu His Asn His Tyr Thr Gln Lys
            340                 345                 350

Ser Leu Ser Leu Ser Pro Gly Lys
            355                 360

<210> SEQ ID NO 76
<211> LENGTH: 360
<212> TYPE: PRT
<213> ORGANISM: Artificial Sequence
<220> FEATURE:
<223> OTHER INFORMATION: A synthetic Hu56V4-Fc-m2

<400> SEQUENCE: 76

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Arg
            20                  25                  30

Cys Met Ala Trp Phe Arg Gln Ala Pro Gly Lys Gly Leu Glu Arg Val
        35                  40                  45

Ala Lys Leu Leu Thr Thr Ser Gly Ser Thr Tyr Leu Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Ala Glu Asp Thr Ala Val Tyr Tyr Cys
                85                  90                  95

Ala Ala Asp Ser Phe Glu Asp Pro Thr Cys Thr Leu Val Thr Ser Ser
            100                 105                 110

Gly Ala Phe Gln Tyr Trp Gly Gln Gly Thr Leu Val Thr Val Ser Ser
        115                 120                 125

Glu Pro Lys Ser Ser Asp Lys Thr His Thr Cys Pro Pro Cys Pro Ala
    130                 135                 140

Pro Glu Leu Leu Gly Gly Pro Ser Val Phe Leu Phe Pro Pro Lys Pro
145                 150                 155                 160

Lys Asp Thr Leu Met Ile Ser Arg Thr Pro Glu Val Thr Cys Val Val
                165                 170                 175

Val Asp Val Ser His Glu Asp Pro Glu Val Lys Phe Asn Trp Tyr Val
            180                 185                 190

Asp Gly Val Glu Val His Asn Ala Lys Thr Lys Pro Arg Glu Glu Gln
        195                 200                 205

Tyr Ala Ser Thr Tyr Arg Val Val Ser Val Leu Thr Val Leu His Gln
    210                 215                 220

Asp Trp Leu Asn Gly Lys Glu Tyr Lys Cys Lys Val Ser Asn Lys Ala
225                 230                 235                 240

Leu Pro Ala Pro Ile Glu Lys Thr Ile Ser Lys Ala Lys Gly Gln Pro
```

```
                        245                 250                 255
Arg Glu Pro Gln Val Tyr Thr Leu Pro Pro Ser Arg Asp Glu Leu Thr
                260                 265                 270

Lys Asn Gln Val Ser Leu Thr Cys Leu Val Lys Gly Phe Tyr Pro Ser
            275                 280                 285

Asp Ile Ala Val Glu Trp Glu Ser Asn Gly Gln Pro Glu Asn Asn Tyr
        290                 295                 300

Lys Thr Thr Pro Pro Val Leu Asp Ser Asp Gly Ser Phe Phe Leu Tyr
305                 310                 315                 320

Ser Lys Leu Thr Val Asp Lys Ser Arg Trp Gln Gln Gly Asn Val Phe
                325                 330                 335

Ser Cys Ser Val Met His Glu Ala Leu His Asn His Tyr Thr Gln Lys
            340                 345                 350

Ser Leu Ser Leu Ser Pro Gly Lys
            355                 360

<210> SEQ ID NO 77
<211> LENGTH: 360
<212> TYPE: PRT
<213> ORGANISM: Artificial Sequence
<220> FEATURE:
<223> OTHER INFORMATION: A synthetic Hu56V5-Fc-m2

<400> SEQUENCE: 77

Gln Val Gln Leu Val Glu Ser Gly Gly Gly Leu Val Gln Pro Gly Gly
1               5                   10                  15

Ser Leu Arg Leu Ser Cys Ala Ala Ser Gly Lys Met Ser Ser Arg Arg
            20                  25                  30

Cys Met Ala Trp Phe Arg Gln Ala Pro Gly Lys Glu Arg Glu Arg Val
        35                  40                  45

Ala Lys Leu Leu Thr Thr Ser Gly Ser Thr Tyr Leu Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Lys Ala Glu Asp Thr Ala Val Tyr Tyr Cys
                85                  90                  95

Ala Ala Asp Ser Phe Glu Asp Pro Thr Cys Thr Leu Val Thr Ser Ser
            100                 105                 110

Gly Ala Phe Gln Tyr Trp Gly Gln Gly Thr Leu Val Thr Val Ser Ser
        115                 120                 125

Glu Pro Lys Ser Ser Asp Lys Thr His Thr Cys Pro Pro Cys Pro Ala
    130                 135                 140

Pro Glu Leu Leu Gly Gly Pro Ser Val Phe Leu Phe Pro Pro Lys Pro
145                 150                 155                 160

Lys Asp Thr Leu Met Ile Ser Arg Thr Pro Glu Val Thr Cys Val Val
                165                 170                 175

Val Asp Val Ser His Glu Asp Pro Glu Val Lys Phe Asn Trp Tyr Val
            180                 185                 190

Asp Gly Val Glu Val His Asn Ala Lys Thr Lys Pro Arg Glu Glu Gln
        195                 200                 205

Tyr Ala Ser Thr Tyr Arg Val Val Ser Val Leu Thr Val Leu His Gln
    210                 215                 220

Asp Trp Leu Asn Gly Lys Glu Tyr Lys Cys Lys Val Ser Asn Lys Ala
225                 230                 235                 240

Leu Pro Ala Pro Ile Glu Lys Thr Ile Ser Lys Ala Lys Gly Gln Pro
```

```
                    245                 250                 255
Arg Glu Pro Gln Val Tyr Thr Leu Pro Pro Ser Arg Asp Glu Leu Thr
                260                 265                 270

Lys Asn Gln Val Ser Leu Thr Cys Leu Val Lys Gly Phe Tyr Pro Ser
            275                 280                 285

Asp Ile Ala Val Glu Trp Glu Ser Asn Gly Gln Pro Glu Asn Asn Tyr
        290                 295                 300

Lys Thr Thr Pro Pro Val Leu Asp Ser Asp Gly Ser Phe Phe Leu Tyr
305                 310                 315                 320

Ser Lys Leu Thr Val Asp Lys Ser Arg Trp Gln Gln Gly Asn Val Phe
                325                 330                 335

Ser Cys Ser Val Met His Glu Ala Leu His Asn His Tyr Thr Gln Lys
            340                 345                 350

Ser Leu Ser Leu Ser Pro Gly Lys
            355                 360

<210> SEQ ID NO 78
<211> LENGTH: 360
<212> TYPE: PRT
<213> ORGANISM: Artificial Sequence
<220> FEATURE:
<223> OTHER INFORMATION: A synthetic 56-Fc-m1

<400> SEQUENCE: 78

Gln Val Gln Leu Gln Glu Ser Gly Gly Gly Leu Val Gln Pro Gly Gly
1               5                   10                  15

Ser Leu Arg Leu Ser Cys Ala Ala Ser Gly Lys Met Ser Ser Arg Arg
            20                  25                  30

Cys Met Ala Trp Phe Arg Gln Ala Pro Gly Lys Glu Arg Glu Arg Val
        35                  40                  45

Ala Lys Leu Leu Thr Thr Ser Gly Ser Thr Tyr Leu Ala Asp Ser Val
    50                  55                  60

Lys Gly Arg Phe Thr Ile Ser Gln Asn Asn Ala Lys Ser Thr Val Tyr
65                  70                  75                  80

Leu Gln Met Asn Ser Leu Lys Pro Glu Asp Thr Ala Met Tyr Tyr Cys
                85                  90                  95

Ala Ala Asp Ser Phe Glu Asp Pro Thr Cys Thr Leu Val Thr Ser Ser
            100                 105                 110

Gly Ala Phe Gln Tyr Trp Gly Gln Gly Thr Gln Val Thr Val Ser Ser
        115                 120                 125

Glu Pro Lys Ser Ser Asp Lys Thr His Thr Cys Pro Pro Cys Pro Ala
    130                 135                 140

Pro Glu Leu Leu Gly Gly Pro Ser Val Phe Leu Phe Pro Pro Lys Pro
145                 150                 155                 160

Lys Asp Thr Leu Met Ile Ser Arg Thr Pro Glu Val Thr Cys Val Val
                165                 170                 175

Val Ala Val Ser His Glu Asp Pro Glu Val Lys Phe Asn Trp Tyr Val
            180                 185                 190

Asp Gly Val Glu Val His Asn Ala Lys Thr Lys Pro Arg Glu Glu Gln
        195                 200                 205

Tyr Asn Ser Thr Tyr Arg Val Val Ser Val Leu Thr Val Leu His Gln
    210                 215                 220

Asp Trp Leu Asn Gly Lys Glu Tyr Lys Cys Lys Val Ser Asn Lys Ala
225                 230                 235                 240

Leu Pro Ala Gly Ile Glu Lys Thr Ile Ser Lys Ala Lys Gly Gln Pro
```

```
                      245                 250                 255
Arg Glu Pro Gln Val Tyr Thr Leu Pro Pro Ser Arg Asp Glu Leu Thr
                260                 265                 270

Lys Asn Gln Val Ser Leu Thr Cys Leu Val Lys Gly Phe Tyr Pro Ser
            275                 280                 285

Asp Ile Ala Val Glu Trp Glu Ser Asn Gly Gln Pro Glu Asn Asn Tyr
        290                 295                 300

Lys Thr Thr Pro Pro Val Leu Asp Ser Asp Gly Ser Phe Phe Leu Tyr
305                 310                 315                 320

Ser Lys Leu Thr Val Asp Lys Ser Arg Trp Gln Gln Gly Asn Val Phe
                325                 330                 335

Ser Cys Ser Val Met His Glu Ala Leu His Asn His Tyr Thr Gln Lys
            340                 345                 350

Ser Leu Ser Leu Ser Pro Gly Lys
        355                 360

<210> SEQ ID NO 79
<211> LENGTH: 360
<212> TYPE: PRT
<213> ORGANISM: Artificial Sequence
<220> FEATURE:
<223> OTHER INFORMATION: A synthetic Hu56V1-Fc-m1

<400> SEQUENCE: 79

Gln Val Gln Leu Val Glu Ser Gly Gly Gly Leu Val Gln Pro Gly Gly
1               5                   10                  15

Ser Leu Arg Leu Ser Cys Ala Ala Ser Gly Lys Met Ser Ser Arg Arg
            20                  25                  30

Cys Met Ala Trp Phe Arg Gln Ala Pro Gly Lys Glu Arg Glu Arg Val
        35                  40                  45

Ala Lys Leu Leu Thr Thr Ser Gly Ser Thr Tyr Leu Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Ala Glu Asp Thr Ala Val Tyr Tyr Cys
                85                  90                  95

Ala Ala Asp Ser Phe Glu Asp Pro Thr Cys Thr Leu Val Thr Ser Ser
            100                 105                 110

Gly Ala Phe Gln Tyr Trp Gly Gln Gly Thr Leu Val Thr Val Ser Ser
        115                 120                 125

Glu Pro Lys Ser Ser Asp Lys Thr His Thr Cys Pro Pro Cys Pro Ala
    130                 135                 140

Pro Glu Leu Leu Gly Gly Pro Ser Val Phe Leu Phe Pro Pro Lys Pro
145                 150                 155                 160

Lys Asp Thr Leu Met Ile Ser Arg Thr Pro Glu Val Thr Cys Val Val
                165                 170                 175

Val Ala Val Ser His Glu Asp Pro Glu Val Lys Phe Asn Trp Tyr Val
            180                 185                 190

Asp Gly Val Glu Val His Asn Ala Lys Thr Lys Pro Arg Glu Glu Gln
        195                 200                 205

Tyr Asn Ser Thr Tyr Arg Val Val Ser Val Leu Thr Val Leu His Gln
    210                 215                 220

Asp Trp Leu Asn Gly Lys Glu Tyr Lys Cys Lys Val Ser Asn Lys Ala
225                 230                 235                 240

Leu Pro Ala Gly Ile Glu Lys Thr Ile Ser Lys Ala Lys Gly Gln Pro
```

```
                    245                 250                 255
Arg Glu Pro Gln Val Tyr Thr Leu Pro Pro Ser Arg Asp Glu Leu Thr
                260                 265                 270

Lys Asn Gln Val Ser Leu Thr Cys Leu Val Lys Gly Phe Tyr Pro Ser
            275                 280                 285

Asp Ile Ala Val Glu Trp Glu Ser Asn Gly Gln Pro Glu Asn Asn Tyr
        290                 295                 300

Lys Thr Thr Pro Pro Val Leu Asp Ser Asp Gly Ser Phe Phe Leu Tyr
305                 310                 315                 320

Ser Lys Leu Thr Val Asp Lys Ser Arg Trp Gln Gln Gly Asn Val Phe
                325                 330                 335

Ser Cys Ser Val Met His Glu Ala Leu His Asn His Tyr Thr Gln Lys
            340                 345                 350

Ser Leu Ser Leu Ser Pro Gly Lys
        355                 360

<210> SEQ ID NO 80
<211> LENGTH: 360
<212> TYPE: PRT
<213> ORGANISM: Artificial Sequence
<220> FEATURE:
<223> OTHER INFORMATION: A synthetic Hu56V2-Fc-m1

<400> SEQUENCE: 80

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Arg
            20                  25                  30

Cys Met Ala Trp Phe Arg Gln Ala Pro Gly Lys Glu Arg Glu Arg Val
        35                  40                  45

Ala Lys Leu Leu Thr Thr Ser Gly Ser Thr Tyr Leu Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Ala Glu Asp Thr Ala Val Tyr Tyr Cys
                85                  90                  95

Ala Ala Asp Ser Phe Glu Asp Pro Thr Cys Thr Leu Val Thr Ser Ser
            100                 105                 110

Gly Ala Phe Gln Tyr Trp Gly Gln Gly Thr Leu Val Thr Val Ser Ser
        115                 120                 125

Glu Pro Lys Ser Ser Asp Lys Thr His Thr Cys Pro Pro Cys Pro Ala
    130                 135                 140

Pro Glu Leu Leu Gly Gly Pro Ser Val Phe Leu Phe Pro Pro Lys Pro
145                 150                 155                 160

Lys Asp Thr Leu Met Ile Ser Arg Thr Pro Glu Val Thr Cys Val Val
                165                 170                 175

Val Ala Val Ser His Glu Asp Pro Glu Val Lys Phe Asn Trp Tyr Val
            180                 185                 190

Asp Gly Val Glu Val His Asn Ala Lys Thr Lys Pro Arg Glu Glu Gln
        195                 200                 205

Tyr Asn Ser Thr Tyr Arg Val Val Ser Val Leu Thr Val Leu His Gln
    210                 215                 220

Asp Trp Leu Asn Gly Lys Glu Tyr Lys Cys Lys Val Ser Asn Lys Ala
225                 230                 235                 240

Leu Pro Ala Gly Ile Glu Lys Thr Ile Ser Lys Ala Lys Gly Gln Pro
```

```
                245                 250                 255
Arg Glu Pro Gln Val Tyr Thr Leu Pro Pro Ser Arg Asp Glu Leu Thr
            260                 265                 270

Lys Asn Gln Val Ser Leu Thr Cys Leu Val Lys Gly Phe Tyr Pro Ser
        275                 280                 285

Asp Ile Ala Val Glu Trp Glu Ser Asn Gly Gln Pro Glu Asn Asn Tyr
    290                 295                 300

Lys Thr Thr Pro Pro Val Leu Asp Ser Asp Gly Ser Phe Phe Leu Tyr
305                 310                 315                 320

Ser Lys Leu Thr Val Asp Lys Ser Arg Trp Gln Gln Gly Asn Val Phe
                325                 330                 335

Ser Cys Ser Val Met His Glu Ala Leu His Asn His Tyr Thr Gln Lys
            340                 345                 350

Ser Leu Ser Leu Ser Pro Gly Lys
        355                 360
```

<210> SEQ ID NO 81
<211> LENGTH: 360
<212> TYPE: PRT
<213> ORGANISM: Artificial Sequence
<220> FEATURE:
<223> OTHER INFORMATION: A synthetic Hu56V3-Fc-m1

<400> SEQUENCE: 81

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Lys Met Ser Ser Arg Arg
            20                  25                  30

Cys Met Ala Trp Phe Arg Gln Ala Pro Gly Lys Gly Leu Glu Arg Val
        35                  40                  45

Ala Lys Leu Leu Thr Thr Ser Gly Ser Thr Tyr Leu Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Ala Glu Asp Thr Ala Val Tyr Tyr Cys
                85                  90                  95

Ala Ala Asp Ser Phe Glu Asp Pro Thr Cys Thr Leu Val Thr Ser Ser
            100                 105                 110

Gly Ala Phe Gln Tyr Trp Gly Gln Gly Thr Leu Val Thr Val Ser Ser
        115                 120                 125

Glu Pro Lys Ser Ser Asp Lys Thr His Thr Cys Pro Pro Cys Pro Ala
    130                 135                 140

Pro Glu Leu Leu Gly Gly Pro Ser Val Phe Leu Phe Pro Pro Lys Pro
145                 150                 155                 160

Lys Asp Thr Leu Met Ile Ser Arg Thr Pro Glu Val Thr Cys Val Val
                165                 170                 175

Val Ala Val Ser His Glu Asp Pro Glu Val Lys Phe Asn Trp Tyr Val
            180                 185                 190

Asp Gly Val Glu Val His Asn Ala Lys Thr Lys Pro Arg Glu Glu Gln
        195                 200                 205

Tyr Asn Ser Thr Tyr Arg Val Val Ser Val Leu Thr Val Leu His Gln
    210                 215                 220

Asp Trp Leu Asn Gly Lys Glu Tyr Lys Cys Lys Val Ser Asn Lys Ala
225                 230                 235                 240

Leu Pro Ala Gly Ile Glu Lys Thr Ile Ser Lys Ala Lys Gly Gln Pro
```

```
                245                 250                 255
Arg Glu Pro Gln Val Tyr Thr Leu Pro Pro Ser Arg Asp Glu Leu Thr
            260                 265                 270

Lys Asn Gln Val Ser Leu Thr Cys Leu Val Lys Gly Phe Tyr Pro Ser
        275                 280                 285

Asp Ile Ala Val Glu Trp Glu Ser Asn Gly Gln Pro Glu Asn Asn Tyr
    290                 295                 300

Lys Thr Thr Pro Pro Val Leu Asp Ser Asp Gly Ser Phe Phe Leu Tyr
305                 310                 315                 320

Ser Lys Leu Thr Val Asp Lys Ser Arg Trp Gln Gln Gly Asn Val Phe
                325                 330                 335

Ser Cys Ser Val Met His Glu Ala Leu His Asn His Tyr Thr Gln Lys
            340                 345                 350

Ser Leu Ser Leu Ser Pro Gly Lys
        355                 360

<210> SEQ ID NO 82
<211> LENGTH: 360
<212> TYPE: PRT
<213> ORGANISM: Artificial Sequence
<220> FEATURE:
<223> OTHER INFORMATION: A synthetic Hu56V4-Fc-m1

<400> SEQUENCE: 82

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Arg
            20                  25                  30

Cys Met Ala Trp Phe Arg Gln Ala Pro Gly Lys Gly Leu Glu Arg Val
        35                  40                  45

Ala Lys Leu Leu Thr Thr Ser Gly Ser Thr Tyr Leu Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Ala Glu Asp Thr Ala Val Tyr Tyr Cys
                85                  90                  95

Ala Ala Asp Ser Phe Glu Asp Pro Thr Cys Thr Leu Val Thr Ser Ser
            100                 105                 110

Gly Ala Phe Gln Tyr Trp Gly Gln Gly Thr Leu Val Thr Val Ser Ser
        115                 120                 125

Glu Pro Lys Ser Ser Asp Lys Thr His Thr Cys Pro Pro Cys Pro Ala
    130                 135                 140

Pro Glu Leu Leu Gly Gly Pro Ser Val Phe Leu Phe Pro Pro Lys Pro
145                 150                 155                 160

Lys Asp Thr Leu Met Ile Ser Arg Thr Pro Glu Val Thr Cys Val Val
                165                 170                 175

Val Ala Val Ser His Glu Asp Pro Glu Val Lys Phe Asn Trp Tyr Val
            180                 185                 190

Asp Gly Val Glu Val His Asn Ala Lys Thr Lys Pro Arg Glu Glu Gln
        195                 200                 205

Tyr Asn Ser Thr Tyr Arg Val Val Ser Val Leu Thr Val Leu His Gln
    210                 215                 220

Asp Trp Leu Asn Gly Lys Glu Tyr Lys Cys Lys Val Ser Asn Lys Ala
225                 230                 235                 240

Leu Pro Ala Gly Ile Glu Lys Thr Ile Ser Lys Ala Lys Gly Gln Pro
```

```
                     245                 250                 255
Arg Glu Pro Gln Val Tyr Thr Leu Pro Pro Ser Arg Asp Glu Leu Thr
                260                 265                 270

Lys Asn Gln Val Ser Leu Thr Cys Leu Val Lys Gly Phe Tyr Pro Ser
            275                 280                 285

Asp Ile Ala Val Glu Trp Glu Ser Asn Gly Gln Pro Glu Asn Asn Tyr
        290                 295                 300

Lys Thr Thr Pro Pro Val Leu Asp Ser Asp Gly Ser Phe Phe Leu Tyr
305                 310                 315                 320

Ser Lys Leu Thr Val Asp Lys Ser Arg Trp Gln Gln Gly Asn Val Phe
                325                 330                 335

Ser Cys Ser Val Met His Glu Ala Leu His Asn His Tyr Thr Gln Lys
            340                 345                 350

Ser Leu Ser Leu Ser Pro Gly Lys
        355                 360

<210> SEQ ID NO 83
<211> LENGTH: 360
<212> TYPE: PRT
<213> ORGANISM: Artificial Sequence
<220> FEATURE:
<223> OTHER INFORMATION: A synthetic Hu56V5-Fc-m1

<400> SEQUENCE: 83

Gln Val Gln Leu Val Glu Ser Gly Gly Gly Leu Val Gln Pro Gly Gly
1               5                   10                  15

Ser Leu Arg Leu Ser Cys Ala Ala Ser Gly Lys Met Ser Ser Arg Arg
            20                  25                  30

Cys Met Ala Trp Phe Arg Gln Ala Pro Gly Lys Glu Arg Glu Arg Val
        35                  40                  45

Ala Lys Leu Leu Thr Thr Ser Gly Ser Thr Tyr Leu Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Lys Ala Glu Asp Thr Ala Val Tyr Tyr Cys
                85                  90                  95

Ala Ala Asp Ser Phe Glu Asp Pro Thr Cys Thr Leu Val Thr Ser Ser
            100                 105                 110

Gly Ala Phe Gln Tyr Trp Gly Gln Gly Thr Leu Val Thr Val Ser Ser
        115                 120                 125

Glu Pro Lys Ser Ser Asp Lys Thr His Thr Cys Pro Pro Cys Pro Ala
    130                 135                 140

Pro Glu Leu Leu Gly Gly Pro Ser Val Phe Leu Phe Pro Pro Lys Pro
145                 150                 155                 160

Lys Asp Thr Leu Met Ile Ser Arg Thr Pro Glu Val Thr Cys Val Val
                165                 170                 175

Val Ala Val Ser His Glu Asp Pro Glu Val Lys Phe Asn Trp Tyr Val
            180                 185                 190

Asp Gly Val Glu Val His Asn Ala Lys Thr Lys Pro Arg Glu Glu Gln
        195                 200                 205

Tyr Asn Ser Thr Tyr Arg Val Val Ser Val Leu Thr Val Leu His Gln
    210                 215                 220

Asp Trp Leu Asn Gly Lys Glu Tyr Lys Cys Lys Val Ser Asn Lys Ala
225                 230                 235                 240

Leu Pro Ala Gly Ile Glu Lys Thr Ile Ser Lys Ala Lys Gly Gln Pro
```

```
                    245                 250                 255
Arg Glu Pro Gln Val Tyr Thr Leu Pro Pro Ser Arg Asp Glu Leu Thr
                260                 265                 270
Lys Asn Gln Val Ser Leu Thr Cys Leu Val Lys Gly Phe Tyr Pro Ser
            275                 280                 285
Asp Ile Ala Val Glu Trp Glu Ser Asn Gly Gln Pro Glu Asn Asn Tyr
        290                 295                 300
Lys Thr Thr Pro Pro Val Leu Asp Ser Asp Gly Ser Phe Phe Leu Tyr
305                 310                 315                 320
Ser Lys Leu Thr Val Asp Lys Ser Arg Trp Gln Gln Gly Asn Val Phe
                325                 330                 335
Ser Cys Ser Val Met His Glu Ala Leu His Asn His Tyr Thr Gln Lys
            340                 345                 350
Ser Leu Ser Leu Ser Pro Gly Lys
            355                 360

<210> SEQ ID NO 84
<211> LENGTH: 456
<212> TYPE: PRT
<213> ORGANISM: Artificial Sequence
<220> FEATURE:
<223> OTHER INFORMATION: A synthetic human PDL1-muFc

<400> SEQUENCE: 84

Phe Thr Val Thr Val Pro Lys Asp Leu Tyr Val Val Glu Tyr Gly Ser
1               5                   10                  15
Asn Met Thr Ile Glu Cys Lys Phe Pro Val Glu Lys Gln Leu Asp Leu
            20                  25                  30
Ala Ala Leu Ile Val Tyr Trp Glu Met Glu Asp Lys Asn Ile Ile Gln
        35                  40                  45
Phe Val His Gly Glu Glu Asp Leu Lys Val Gln His Ser Ser Tyr Arg
    50                  55                  60
Gln Arg Ala Arg Leu Leu Lys Asp Gln Leu Ser Leu Gly Asn Ala Ala
65                  70                  75                  80
Leu Gln Ile Thr Asp Val Lys Leu Gln Asp Ala Gly Val Tyr Arg Cys
                85                  90                  95
Met Ile Ser Tyr Gly Gly Ala Asp Tyr Lys Arg Ile Thr Val Lys Val
            100                 105                 110
Asn Ala Pro Tyr Asn Lys Ile Asn Gln Arg Ile Leu Val Val Asp Pro
        115                 120                 125
Val Thr Ser Glu His Glu Leu Thr Cys Gln Ala Glu Gly Tyr Pro Lys
    130                 135                 140
Ala Glu Val Ile Trp Thr Ser Ser Asp His Gln Val Leu Ser Gly Lys
145                 150                 155                 160
Thr Thr Thr Thr Asn Ser Lys Arg Glu Glu Lys Leu Phe Asn Val Thr
                165                 170                 175
Ser Thr Leu Arg Ile Asn Thr Thr Asn Glu Ile Phe Tyr Cys Thr
            180                 185                 190
Phe Arg Arg Leu Asp Pro Glu Glu Asn His Thr Ala Glu Leu Val Ile
        195                 200                 205
Pro Glu Leu Pro Leu Ala His Pro Pro Asn Glu Arg Thr Asp Ile Glu
    210                 215                 220
Gly Arg Met Asp Pro Lys Ser Ser Asp Lys Thr His Thr Cys Pro Pro
225                 230                 235                 240
Cys Pro Ala Pro Glu Val Ser Ser Val Phe Ile Phe Pro Pro Lys Pro
```

```
                    245                 250                 255
Lys Asp Val Leu Thr Ile Thr Leu Thr Pro Lys Val Thr Cys Val Val
                260                 265                 270

Val Asp Ile Ser Lys Asp Asp Pro Glu Val Gln Phe Ser Trp Phe Val
                275                 280                 285

Asp Asp Val Glu Val His Thr Ala Gln Thr Gln Pro Arg Glu Glu Gln
            290                 295                 300

Phe Asn Ser Thr Phe Arg Ser Val Ser Glu Leu Pro Ile Met His Gln
305                 310                 315                 320

Asp Trp Leu Asn Gly Lys Glu Phe Lys Cys Arg Val Asn Ser Ala Ala
                325                 330                 335

Phe Pro Ala Pro Ile Glu Lys Thr Ile Ser Lys Thr Lys Gly Arg Pro
                340                 345                 350

Lys Ala Pro Gln Val Tyr Thr Ile Pro Pro Lys Glu Gln Met Ala
                355                 360                 365

Lys Asp Lys Val Ser Leu Thr Cys Met Ile Thr Asp Phe Phe Pro Glu
            370                 375                 380

Asp Ile Thr Val Glu Trp Gln Trp Asn Gly Gln Pro Ala Glu Asn Tyr
385                 390                 395                 400

Lys Asn Thr Gln Pro Ile Met Asn Thr Asn Gly Ser Tyr Phe Val Tyr
                405                 410                 415

Ser Lys Leu Asn Val Gln Lys Ser Asn Trp Glu Ala Gly Asn Thr Phe
                420                 425                 430

Thr Cys Ser Val Leu His Glu Gly Leu His Asn His His Thr Glu Lys
                435                 440                 445

Ser Leu Ser His Ser Pro Gly Lys
                450                 455

<210> SEQ ID NO 85
<211> LENGTH: 381
<212> TYPE: PRT
<213> ORGANISM: Artificial Sequence
<220> FEATURE:
<223> OTHER INFORMATION: A synthetic human PD1-muFc

<400> SEQUENCE: 85

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
                20                  25                  30

Thr Cys Ser Phe Ser Asn Thr Ser Glu Ser Phe Val Leu Asn Trp Tyr
            35                  40                  45

Arg Met Ser Pro Ser Asn Gln Thr Asp Lys Leu Ala Ala Phe Pro Glu
        50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Gly Ala Ile Ser Leu Ala Pro Lys Ala
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
130                 135                 140

Gln Phe Gln Ile Glu Gly Arg Met Asp Pro Lys Ser Ser Asp Lys Thr
```

```
145                 150                 155                 160
His Thr Cys Pro Pro Cys Pro Ala Pro Glu Val Ser Ser Val Phe Ile
            165                 170                 175

Phe Pro Pro Lys Pro Lys Asp Val Leu Thr Ile Thr Leu Thr Pro Lys
            180                 185                 190

Val Thr Cys Val Val Val Asp Ile Ser Lys Asp Asp Pro Glu Val Gln
        195                 200                 205

Phe Ser Trp Phe Val Asp Asp Val Glu Val His Thr Ala Gln Thr Gln
    210                 215                 220

Pro Arg Glu Glu Gln Phe Asn Ser Thr Phe Arg Ser Val Ser Glu Leu
225                 230                 235                 240

Pro Ile Met His Gln Asp Trp Leu Asn Gly Lys Glu Phe Lys Cys Arg
                245                 250                 255

Val Asn Ser Ala Ala Phe Pro Ala Pro Ile Glu Lys Thr Ile Ser Lys
                260                 265                 270

Thr Lys Gly Arg Pro Lys Ala Pro Gln Val Tyr Thr Ile Pro Pro Pro
                275                 280                 285

Lys Glu Gln Met Ala Lys Asp Lys Val Ser Leu Thr Cys Met Ile Thr
    290                 295                 300

Asp Phe Phe Pro Glu Asp Ile Thr Val Glu Trp Gln Trp Asn Gly Gln
305                 310                 315                 320

Pro Ala Glu Asn Tyr Lys Asn Thr Gln Pro Ile Met Asn Thr Asn Gly
                325                 330                 335

Ser Tyr Phe Val Tyr Ser Lys Leu Asn Val Gln Lys Ser Asn Trp Glu
                340                 345                 350

Ala Gly Asn Thr Phe Thr Cys Ser Val Leu His Glu Gly Leu His Asn
                355                 360                 365

His His Thr Glu Lys Ser Leu Ser His Ser Pro Gly Lys
    370                 375                 380
```

SINGLE DOMAIN ANTIBODY AND DERIVATIVE PROTEINS THEREOF AGAINST PROGRAMMED DEATH-LIGAND (PDL1)

PRIORITY APPLICATIONS

This application is a U.S. National Stage under 35 U.S.C. 371 from International Application No. PCT/CN2016/092679, filed on 1 Aug. 2016, and published as WO2017/020801 on 9 Feb. 2017, which claims the benefit of priority to Chinese Application No. 201510465481.8, filed on 31 Jul. 2015; which applications and publication are incorporated herein by reference in their entirety.

TECHNICAL FIELD

The present invention relates to the field of medical biology, and discloses a single domain antibody and derivative proteins thereof against programmed death ligand (PDL1). In particular, the present invention discloses a programmed death ligand 1 (PDL1) binding molecule and the use thereof, especially the use for treating and/or preventing or diagnosing PDL1 relating diseases such as tumor.

BACKGROUND

Programmed death 1 (PD-1) is a member of the CD28 family of receptors, which includes CD28, CTLA-4, ICOS, PD-1, and BTLA. The initial members of the family, CD28 and ICOS, were discovered by functional effect on augmenting T cell proliferation following the addition of monoclonal antibodies (Hutloff et al. (1999) Nature 397:263-266; Hansen et al. (1980) Immunogenics 10:247-260). Two cell surface glycoprotein ligands for PD-1 have been identified, PDL1 and PD-L2, and have been shown to downregulate T cell activation and cytokine secretion upon binding to PD-1 (Freeman et al. (2000) J Exp Med 192:1027-34; Latchman et al. (2001) Nat Immunol 2:261-8; Carter et al. (2002) Eur J Immunol 32:634-43; Ohigashi et al. (2005) Clin Cancer Res 11:2947-53). Both PDL1 (B7-H1) and PDL2 (B7-DC) are B7 homologs that bind to PD-1 but do not bind to other CD28 family members (Blank et al. (2004). Expression of PDL1 on the cell surface has also been shown to be upregulated through IFN-γ stimulation.

PDL1 expression has been found in several murine and human cancers, including human lung, ovarian and colon carcinoma and various myelomas (Iwai et al. (2002) PNAS 99:12293-7; Ohigashi et al. (2005). Clin Cancer Res 11:2947-53). Currently available results reveal that PDL1 overexpressed in tumor cells plays a key role in tumor immunity escape by increasing apoptosis of T-cells. Researchers found that P815 tumor cell line transfected with PDL1 gene can be resistant to specific lysis by CTL, and has increased oncogenicity and invasive activity. These biological activities can be reversed by blocking PDL1. Tumor cells transplanted into mice with PDL1 knocked out to block PDL1/PD-1 interaction, cannot form tumors (Dong et al. (2002) Nat Med 8:793-800). It has also been suggested that PDL1 might be involved in intestinal mucosal inflammation and inhibition of PDL1 suppresses wasting disease associated with colitis (Kanai et al. (2003) J Immunol 171:4156-63).

There is still a need in the art for anti-PDL1 antibody which can bind to PDL1 with high affinity and be capable of blocking the binding of PDL1 to PD-1 and, especially a heavy chain single domain antibody against PDL1.

BRIEF DESCRIPTION OF THE INVENTION

The present inventors have obtained anti-PDL1 heavy chain single domain antibody (VHH) with high specificity, high affinity and high stability by screening with phage display technology.

In a first aspect, the invention provides a PDL1-binding molecule comprising immunoglobulin single variable domain that specifically binds to PDL1.

In another aspect, the present invention relates to a nucleic acid molecule encoding the PDL1-binding molecule, and an expression vector and host cell containing said nucleic acid molecule.

The present invention further relates to an immunoconjugate and pharmaceutical composition comprising the PDL1-binding molecule of the invention.

The present invention further relates to a method for producing the PDL1-binding molecule of the invention.

The present invention further relates to use of the PDL1-binding molecule, immunoconjugate and pharmaceutical composition of the invention, especially the use and method for preventing and/or treating PDL1 relating diseases.

DETAILED DESCRIPTION OF THE INVENTION

Definitions

Figure 1:
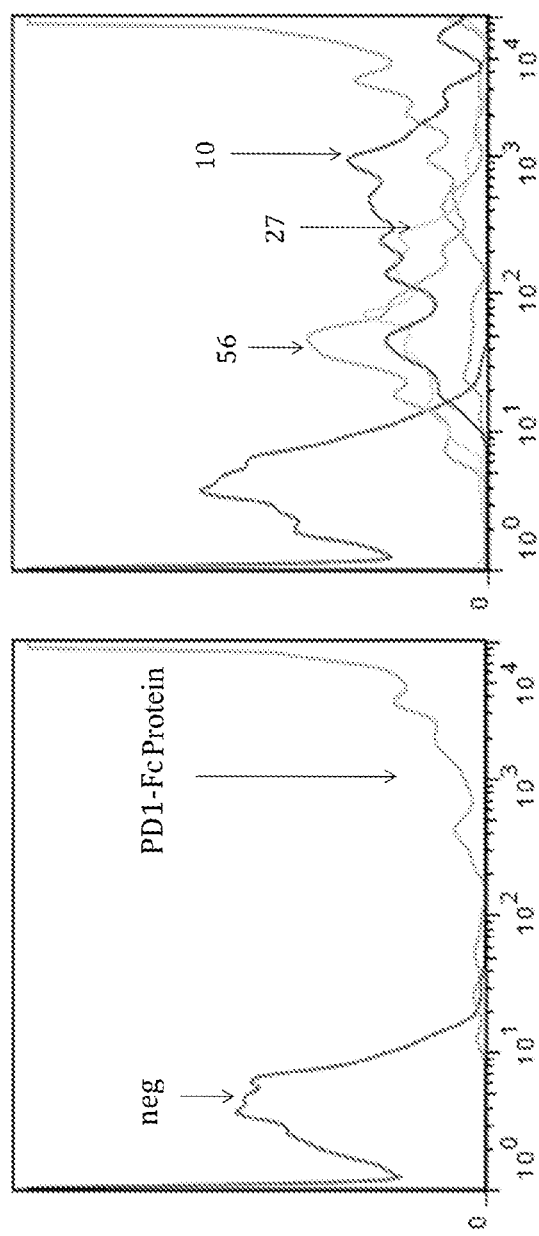
FIG. 1. shows the blocking effect of PDL1 heavy chain single domain antibodies to PD1/PDL1 interaction.

Unless indicated or defined otherwise, all terms used have their usual meaning in the art, which will be clear to the skilled person. Reference is for example made to the standard handbooks, such as Sambrook et al, "Molecular Cloning: A Laboratory Manual" (2nd Ed.), Vols. 1-3, Cold Spring Harbor Laboratory Press (1989); Lewin, "Genes IV", Oxford University Press, New York, (1990), and Roitt et al., "Immunology" (2nd Ed.), Gower Medical Publishing, London, New York (1989), as well as to the general background art cited herein. Furthermore, unless indicated otherwise, all methods, steps, techniques and manipulations that are not specifically described in detail can be performed and have been performed in a manner known per se, as will be clear to the skilled person. Reference is for example again made to the standard handbooks, to the general background art referred to above and to the further references cited therein.

Unless indicated otherwise, the interchangeable terms "antibody" and "immunoglobulin"—whether used herein to refer to a heavy chain antibody or to a conventional 4-chain antibody—are used as general terms to include both the full-size antibody, the individual chains thereof, as well as all parts, domains or fragments thereof (including but not limited to antigen-binding domains or fragments such as VHH domains or VH/VL domains, respectively). In addition, the term "sequence" as used herein (for example in terms like "immunoglobulin sequence", "antibody sequence", "(single) variable domain sequence", "VHH sequence" or "protein sequence"), should generally be understood to include both the relevant amino acid sequence as well as nucleic acid sequences or nucleotide sequences encoding the same, unless the context requires a more limited interpretation.

The term "domain" (of a polypeptide or protein) as used herein refers to a folded protein structure which has the ability to retain its tertiary structure independently of the rest of the protein. Generally, domains are responsible for discrete functional properties of proteins, and in many cases may be added, removed or transferred to other proteins without loss of function of the remainder of the protein and/or of the domain.

The term "immunoglobulin domain" as used herein refers to a globular region of an antibody chain (such as e.g. a chain of a conventional 4-chain antibody or of a heavy chain antibody), or to a polypeptide that essentially consists of such a globular region. Immunoglobulin domains are characterized in that they retain the immunoglobulin fold characteristic of antibody molecules, which consists of a 2-layer sandwich of about 7 antiparallel beta-strands arranged in two beta-sheets, optionally stabilized by a conserved disulphide bond.

The term "immunoglobulin variable domain" as used herein means an immunoglobulin domain essentially consisting of four "framework regions" which are referred to in the art and hereinbelow as "framework region 1" or "FR1"; as "framework region 2" or "FR2"; as "framework region 3" or "FR3"; and as "framework region 4" or "FR4", respectively; which framework regions are interrupted by three "complementarity determining regions" or "CDRs", which are referred to in the art and hereinbelow as "complementarity determining region" or "CDR1"; as "complementarity determining region 2" or "CDR2"; and as "complementarity determining region 3" or "CDR3", respectively. Thus, the general structure or sequence of an immunoglobulin variable domain can be indicated as follows: FR1-CDR1-FR2-CDR2-FR3-CDR3-FR4. It is the immunoglobulin variable domain(s) that confer specificity to an antibody for the antigen by carrying the antigen-binding site.

The term "immunoglobulin single variable domain" as used herein means an immunoglobulin variable domain which is capable of specifically binding to an epitope of the antigen without pairing with an additional variable immunoglobulin domain. One example of immunoglobulin single variable domains in the meaning of the present invention is "domain antibody", such as the immunoglobulin single variable domains VH and VL (VH domains and VL domains). Another example of immunoglobulin single variable domains is "VHH domain" (or simply "VHH") from camelids, as defined hereinafter.

"VHH domains", also known as heavy chain single domain antibodies, VHHs, $V_HH$ domains, VHH antibody fragments, and VHH antibodies, are the antigen binding immunoglobulin variable domain of "heavy chain antibodies" (i.e., "antibodies devoid of light chains") (Hamers-Casterman C, Atarhouch T, Muyldermans S, Robinson G, Hamers C, Songa E B, Bendahman N, Hamers R.: "Naturally occurring antibodies devoid of light chains"; Nature 363, 446-448 (1993)). The term "VHH domain" has been chosen in order to distinguish these variable domains from the heavy chain variable domains that are present in conventional 4-chain antibodies (which are referred to herein as "VH domains") and from the light chain variable domains that are present in conventional 4-chain antibodies (which are referred to herein as "VL domains"). VHH domains can specifically bind to an epitope without an additional antigen binding domain (as opposed to VH or VL domains in a conventional 4-chain antibody, in which case the epitope is recognized by a VL domain together with a VH domain). VHH domains are small, robust and efficient antigen recognition units formed by a single immunoglobulin domain.

In the context of the present invention, the terms heavy chain single domain antibody, VHH domain, VHH, $V_HH$ domain, VHH antibody fragment, VHH antibody, as well as "Nanobody®" and "Nanobody® domain" ("Nanobody" being a trademark of the company Ablynx N.V.; Ghent; Belgium) are used interchangeably.

The amino acid residues of VHH domains from Camelids are numbered according to the general numbering for VH domains given by Kabat et al. ("Sequence of proteins of immunological interest". US Public Health Services, NIH Bethesda, Md., Publication No. 91). as shown e.g. in FIG. 2 of Riechmann and Muyldermans, J. Immunol. Methods 231, 25-38 (1999). According to this numbering, FR1 comprises the amino acid residues at positions 1-30,
CDR1 comprises the amino acid residues at positions 31-35,
FR2 comprises the amino acids at positions 36-49,
CDR2 comprises the amino acid residues at positions 50-65,
FR3 comprises the amino acid residues at positions 66-94,
CDR3 comprises the amino acid residues at positions 95-102, and
FR4 comprises the amino acid residues at positions 103-113.

However, it should be noted that—as is well known in the art for VH domains and for VHH domains—the total number of amino acid residues in each of the CDRs may vary and may not correspond to the total number of amino acid residues indicated by the Kabat numbering (that is, one or more positions according to the Kabat numbering may not be occupied in the actual sequence, or the actual sequence may contain more amino acid residues than the number allowed for by the Kabat numbering). This means that, generally, the numbering according to Kabat may or may not correspond to the actual numbering of the amino acid residues in the actual sequence.

Alternative methods for numbering the amino acid residues of VH domains, which methods can also be applied in an analogous manner to VHH domains, are known in the art. However, in the present description, claims and figures, the numbering according to Kabat and applied to VHH domains as described above will be followed, unless indicated otherwise.

The total number of amino acid residues in a VHH domain will usually be in the range of from 110 to 120, often between 112 and 115. It should however be noted that smaller and longer sequences may also be suitable for the purposes described herein.

Further structural characteristics and functional properties of VHH domains and polypeptides containing the same can be summarized as follows:

VHH domains (which have been "designed" by nature to functionally bind to an antigen without the presence of, and without any interaction with, a light chain variable domain) can function as a single, relatively small, functional antigen-binding structural unit, domain or polypeptide. This distinguishes the VHH domains from the VH and VL domains of conventional 4-chain antibodies, which by themselves are generally not suitable for practical application as single antigen-binding proteins or immunoglobulin single variable domains, but need to be combined in some form or another to provide a functional antigen-binding unit (as in for example conventional antibody fragments such as Fab fragments; in scFvs, which consist of a VH domain covalently linked to a VL domain).

Because of these unique properties, the use of VHH domains—either alone or as part of a larger polypeptide—offers a number of significant advantages over the use of conventional VH and VL domains, scFvs or conventional antibody fragments (such as Fab- or F(ab')$_2$-fragments):

only a single domain is required to bind an antigen with high affinity and with high selectivity, so that there is no need to have two separate domains present, nor to assure that these two domains are present in the right spacial conformation and configuration (i.e. through the use of especially designed linkers, as with scFvs);

VHH domains can be expressed from a single gene and require no post-translational folding or modifications;

VHH domains can easily be engineered into multivalent and multispecific formats (formatted);

VHH domains are highly soluble and do not have a tendency to aggregate;

VHH domains are highly stable to heat, pH, proteases and other denaturing agents or conditions and, thus, may be prepared, stored or transported without the use of refrigeration equipments, conveying a cost, time and environmental savings;

VHH domains are easy and relatively cheap to prepare, even on a scale required for production;

VHH domains are relatively small (approximately 15 kDa, or 10 times smaller than a conventional IgG) compared to conventional 4-chain antibodies and antigen-binding fragments thereof, and therefore show high(er) penetration into tissues and can be administered in higher doses than such conventional 4-chain antibodies and antigen-binding fragments thereof;

VHH domains can show so-called cavity-binding properties (especially due to their extended CDR3 loop, compared to conventional VH domains) and can therefore also access targets and epitopes not accessible to conventional 4-chain antibodies and antigen-binding fragments thereof.

Methods of obtaining VHH domains binding to a specific antigen or epitope have been described earlier, e.g. in WO2006/040153 and WO2006/122786; R. van der Linden et al., Journal of Immunological Methods, 240 (2000) 185-195; Li et al., J Biol Chem., 287 (2012) 13713-13721; Deffar et al., African Journal of Biotechnology Vol. 8 (12), pp. 2645-2652, 17 June, 2009 and WO94/04678.

VHH domains derived from camelids can be "humanized" by replacing one or more amino acid residues in the amino acid sequence of the original VHH sequence by one or more of the amino acid residues that occur at the corresponding position(s) in a VH domain from a conventional 4-chain antibody from a human being (also referred to as "sequence optimization", and in addition to humanization, sequence optimization also encompasses other modification to the sequence by one or more mutations for providing improved VHH features, such as removing potential sites for post-translation modification). A humanized VHH domain can contain one or more fully human framework region sequences, and in a specific embodiment, containing IGHV3 human framework region sequence.

As used herein, "domain antibodies" especially refer to the VH or VL domains of non-camelid mammalians, in particular human 4-chain antibodies. In order to bind an epitope as a single antigen binding domain, i.e. without being paired with a VL or VH domain, respectively, specific selection for such antigen binding properties is required, e.g. by using libraries of human single VH or VL domain sequences.

Domain antibodies have, like VHHs, a molecular weight of approximately 13 to approximately 16 kDa and, if derived from fully human sequences, do not require humanization for e.g. therapeutical use in humans. As in the case of VHH domains, the) are well expressed also in prokaryotic expression systems, providing a significant reduction in overall manufacturing cost.

"Domain antibodies" have been described in e.g. Ward, E. S., et al.: "Binding activities of a repertoire of single immunoglobulin variable domains secreted from *Escherichia coli*"; Nature 341:544-546(1989); Holt, L. J. et al.: "Domain antibodies: proteins for therapy"; TRENDS in Biotechnology 21(11):484-490 (2003).

Furthermore, it will also be clear to the skilled person that it is possible to "graft" one or more of the CDRs mentioned above onto other "scaffolds", including but not limited to human scaffolds or non-immunoglobulin scaffolds. Suitable scaffolds and techniques for such CDR grafting are known in the art.

As used herein, the term "epitope" refers to any antigenic determinant on an antigen to which the paratope of an antibody binds. Antigenic determinants typically contain chemically active surface groupings of molecules such as amino acids or sugar side chains and typically have specific three dimensional structural characteristics, as well as specific charge characteristics. For example, an epitope typically includes at least 3, 4, 5, 6, 7, 8, 9, 10, 11, 12, 13, 14 or 15 consecutive or non-consecutive amino acids in a unique spatial conformation, which can be "linear" or "conformational". See, e.g., Epitope Mapping Protocols in Methods in Molecular Biology, Vol. 66, G E. Morris, Ed. (1996). In a linear epitope, all of the points of interaction between the protein and the interacting molecule (such as an antibody) occur linearly along the primary amino acid sequence of the protein. In a conformational epitope, the points of interaction occur across amino acid residues on the protein that are separated from one another.

Epitopes of a given antigen can be identified using a number of epitope mapping techniques, well known in the art. See, e.g., Epitope Mapping Protocols in Methods in Molecular Biology, Vol. 66 (Glenn E. Morris, Ed., 1996). For example, linear epitopes may be determined by e.g., concurrently synthesizing large numbers of peptides on solid supports, the peptides corresponding to portions of the protein molecule, and reacting the peptides with antibodies while the peptides are still attached to the supports. Such techniques are known in the art and described in, e.g., U.S. Pat. No. 4,708,871; Geysen et al. (1984) Proc. Natl. Acad. Sci. USA 81:3998-4002; Geysen et al. (1986) Molec. Immunol. 23:709-715. Similarly, conformational epitopes may be identified by determining spatial conformation of amino acids such as by, e.g., x-ray crystallography and 2-dimensional nuclear magnetic resonance. See, e.g., Epitope Mapping Protocols, supra.

Antibodies can be screened for competitive binding to a same epitope by conventional techniques known in the art. For example, antibodies compete or cross-compete for binding to antigen can be obtained by competitive or cross-competitive assays. A high throughput process for obtaining antibodies binding to a same epitope based upon their cross-competition is described in International Patent Publication No. WO 03/48731. Correspondingly, antibodies and antigen binding fragments thereof that compete with the antibody molecules of the invention for binding to same epitope on PDL1 can be obtained by conventional techniques known in the art.

Generally, the term "specificity" refers to the number of different types of antigens or epitopes to which a particular antigen-binding molecule or antigen-binding protein (such as an immunoglobulin single variable domain of the invention) molecule can bind. The specificity of an antigen-binding molecule can be determined based on its affinity and/or avidity. The affinity, represented by the equilibrium constant for the dissociation of an antigen with an antigen-binding protein (KD), is a measure for the binding strength between an epitope and an antigen-binding site on the antigen-binding protein: the lesser the value of the KD, the stronger the binding strength between an epitope and the antigen-binding molecule (alternatively, the affinity can also be expressed as the affinity constant (KA), which is 1/KD). As will be clear to the skilled person, affinity can be determined in a manner known per se, depending on the specific antigen of interest. Avidity is the measure of the strength of binding between an antigen-binding molecule (such as an immunoglobulin, an antibody, an immunoglobulin single variable domain or a polypeptide containing it) and the pertinent antigen. Avidity is related to both the affinity between an epitope and its antigen binding site on the antigen-binding molecule and the number of pertinent binding sites present on the antigen-binding molecule.

Unless indicated otherwise, the term "PDL1-binding molecule" refers to any molecule that can specifically bind to PDL1. PDL1-binding molecule can encompass the antibodies or immunoconjugates against PDL1 as defined herein. The term "PDL1-binding molecule" encompasses so-called "SMIPs" ("Small Modular Immunopharmaceuticals"), immunoglobulin super family antibodies (IgSF), or CDR-grafted molecules.

"PDL1-binding molecule" refers to both monovalent PDL1-binding molecules (i.e. molecules that bind to one epitope of PDL1) as well as to bi- or multivalent binding molecules (i.e. binding molecules that bind to more than one epitope). PDL1-binding molecule of the invention may contain at least one PDL1-binding immunoglobulin single variable domain, such as VHH. In some embodiments, PDL1-binding molecule of the invention may contain two PDL1-binding immunoglobulin single variable domains such as VHHs. PDL1-binding molecules containing more than one PDL1-binding immunoglobulin single variable domain are also termed "formatted" PDL1-binding molecules. Formatted PDL1-binding molecules may, in addition to the PDL1-binding immunoglobulin single variable domains, comprise linkers and/or moieties with effector functions, e.g. half-life-extending moieties like albumin-binding immunoglobulin single variable domains, and/or a fusion partner like serum albumin and/or an attached polymer like PEG and/or an Fc region. In some embodiments, PDL1-binding molecule of the invention also encompasses bi-specific antibody, which contains immunoglobulin single variable domains that bind to different antigens.

Typically, the PDL1-binding molecules of the invention will bind to the antigen (i.e., PDL1) with a dissociation constant (KD) of $10^{-7}$ to $10^{-11}$ moles/liter (M), and preferably $10^{-8}$ to $10^{-11}$ moles/liter, more preferably $10^{-9}$ to $10^{-11}$ moles/liter, and even more preferably $10^{-10}$ to $10^{-11}$ moles/liter or less (as measured in a Biacore or in a KinExA assay), and/or with an association constant (KA) of at least $10^7$ $M^{-1}$, preferably at least $10^8$ $M^{-1}$, more preferably at least $10^9$ $M^{-1}$, more preferably at least $10^{10}$ $M^{-1}$, such as at least $10^{10}$ $M^{-1}$. Any KD value greater than $10^{-4}$ M is generally considered to indicate non-specific binding. Specific binding of an antigen-binding protein to an antigen or epitope can be determined in any suitable manner known per se. including, for example, the assays described herein, Scatchard analysis and/or competitive binding assays, such as radioimmunoassays (RIA), enzyme immunoassays (EIA) and sandwich competition assays.

Amino acid residues will be indicated according to the standard three-letter or one-letter amino acid code, as generally known and agreed upon in the art. When comparing two amino acid sequences, the term "amino acid difference" refers to insertions, deletions or substitutions of the indicated number of amino acid residues at a position of the reference sequence, compared to a second sequence. In case of substitution(s), such substitution(s) will preferably be conservative amino acid substitution(s), which means that an amino acid residue is replaced with another amino acid residue of similar chemical structure and which has little or essentially no influence on the function, activity or other biological properties of the polypeptide. Such conservative amino acid substitutions are well known in the art, wherein conservative amino acid substitutions preferably are substitutions in which one amino acid within the following groups (i)-(v) is substituted by another amino acid residue within the same group: (i) small aliphatic, nonpolar or slightly polar residues: Ala, Ser, Thr, Pro and Gly; (ii) polar, negatively charged residues and their (uncharged) amides: Asp, Asn, Glu and Gln; (iii) polar, positively charged residues: His, Arg and Lys; (iv) large aliphatic, nonpolar residues: Met, Leu, He, Val and Cys; and (v) aromatic residues: Phe, Tyr and Trp. Particularly preferred conservative amino acid substitutions are as follows: Ala into Gly or into Ser; Arg into Lys; Asn into Gln or into His; Asp into Glu; Cys into Ser; Gln into Asn; Glu into Asp; Gly into Ala or into Pro; His into Asn or into Gln; Ile into Leu or into Val; Leu into Ile or into Val; Lys into Arg, into Gln or into Glu; Met into Leu, into Tyr or into Ile; Phe into Met, into Leu or into Tyr; Ser into Thr; Thr into Ser; Trp into Tyr; Tyr into Trp or into Phe; Val into Ile or into Leu.

"Sequence identity" between two polypeptide sequences indicates the percentage of amino acids that are identical between the sequences. "Sequence similarity" indicates the percentage of amino acids that either are identical or that represent conservative amino acid substitutions. Methods for evaluating the level of sequence identity between amino acid or nucleotide sequences are known in the art. For example, sequence analysis softwares are often used to determine the identity of amino acid sequences. For example, identity can be determined by using the BLAST program at NCBI database. For determination of sequence identity, see e.g., *Computational Molecular Biology*, Lesk, A. M., ed., Oxford University Press, New York, 1988; *Biocomputing: Informatics and Genome Projects*, Smith. D. W., ed., Academic Press, New York, 1993; *Computer Analysis of Sequence Data*, Part I. Griffin, A. M., and Griffin, H. G, eds., Humana Press, New Jersey, 1994; *Sequence Analysis in Molecular Biology*, von Heinje, G. Academic Press, 1987 and *Sequence Analysis Primer*, Gribskov, M. and Devereux, J., eds., M Stockton Press, New York. 1991.

A polypeptide or nucleic acid molecule is considered to be "essentially isolated"—for example, when compared to its native biological source and/or the reaction medium or cultivation medium from which it has been obtained—when it has been separated from at least one other component with which it is usually associated in said source or medium, such as another protein/polypeptide, another nucleic acid, another biological component or macromolecule or at least one contaminant, impurity or minor component. In particular, a polypeptide or nucleic acid molecule is considered "essentially isolated" when it has been purified at least 2-fold, in particular at least 10-fold, more in particular at least 100-fold, and up to 1000-fold or more. A polypeptide or nucleic acid molecule that is "in essentially isolated form" is preferably essentially homogeneous, as determined using a suitable technique, such as a suitable chromatographical technique, such as polyacrylamide gel electrophoresis.

An "affinity-matured" anti-PDL1 antibody, in particular a VHH or a domain antibody, has one or more alterations in one or more CDRs which result in an improved affinity for PDL1, as compared to the respective parent PDL1-binding molecule. Affinity-matured PDL1-binding molecules of the invention may be prepared by methods known in the art, for example, as described by Marks et al., 1992, Biotechnology 10:779-783, or Barbas, et al., 1994, Proc. Nat. Acad. Sci. USA 91: 3809-3813., Shier et al., 1995, Gene 169:147-155; Yelton et al., 1995, Immunol. 155: 1994-2004; Jackson et al., 1995, J. Immunol. 154(7):3310-9; and Hawkins et al., 1992, J. Mol. Biol. 226(3): 889 896; K S Johnson and R E Hawkins, "Affinity maturation of antibodies using phage display", Oxford University Press 1996.

As used herein, the term "subject" refers to mammalian, especially primate, in particular human.

PDL1 Binding Molecule of the Invention

In a first aspect, the invention provides a PDL1-binding molecule, which comprises at least one immunoglobulin single variable domain that can specifically bind to PDL1. In some embodiments, said PDL1-binding molecule comprises one immunoglobulin single variable domain that specifically binds to PDL1. In some embodiments, said PDL1-binding molecule comprises two or more immunoglobulin single variable domains that specifically bind to PDL1.

In some embodiments, said at least one immunoglobulin single variable domain comprises the CDR1, CDR2 and CDR3 selected from:

(1) CDR1 set forth in SEQ ID NO:1, CDR2 set forth in SEQ ID NO:2, CDR3 set forth in SEQ ID NO:3 (corresponding to CDRs of antibody No. 10);

(2) CDR1 set forth in SEQ ID NO:4, CDR2 set forth in SEQ ID NO:5, CDR3 set forth in SEQ ID NO:6 (corresponding to CDRs of antibody No. 27);

(3) CDR1 set forth in SEQ ID NO:7, CDR2 set forth in SEQ ID NO:8, CDR3 set forth in SEQ ID NO:9 (corresponding to CDRs of antibody No. 38);

(4) CDR1 set forth in SEQ ID NO:10, CDR2 set forth in SEQ ID NO:11, CDR3 set forth in SEQ ID NO:12 (corresponding to CDRs of antibody No. 56);

(5) CDR I set forth in SEQ ID NO:13, CDR2 set forth in SEQ ID NO:14, CDR3 set forth in SEQ ID NO:15 (corresponding to CDRs of antibody No. 69);

(6) CDR1 set forth in SEQ ID NO:16, CDR2 set forth in SEQ ID NO:17, CDR3 set forth in SEQ ID NO:18 (corresponding to CDRs of antibody No. 81);

(7) CDR1 set forth in SEQ ID NO:19, CDR2 set forth in SEQ ID NO:20, CDR3 set forth in SEQ ID NO:21 (corresponding to CDRs of antibody No. 87); and (8) CDR1 set forth in SEQ ID NO:22, CDR2 set forth in SEQ ID NO:23, CDR3 set forth in SEQ ID NO:24 (corresponding to CDRs of antibody No. 94).

In some embodiments, said at least one immunoglobulin single variable domain of the PDL1-binding molecule of the invention is VHH. In some specific embodiments, said VHH comprises an amino acid sequence of any one of SEQ ID NOs:25-32. In some other embodiments, said humanized VHH comprises an amino acid sequence having at least 80%, preferably at least 90%, more preferably at least 95%, even more preferably at least 99% sequence identity to any one of SEQ ID NOs:25-32. Alternatively, the amino acid sequence of said VHH contains one or more amino acid substitutions, preferably conservative amino acid substitutions, compared with any one of SEQ ID NOs:25-32. For example, said VHH contains 1, 2, 3, 4, 5, 6, 7, 8, 9 or 10 conservative amino acid substitutions.

In some embodiments, said VHH is a humanized VHH. In some specific embodiments, said humanized VHH comprises an amino acid sequence of any one of SEQ ID NOs:33-37.

In some embodiments, the PDL1-binding molecule of the invention is obtained by affinity maturation. The PDL1-binding molecule obtained by affinity maturation may have one or more alterations in one or more CDRs, such alterations result in an increased affinity to PDL1 when compared with parent PDL1-binding molecule.

In some embodiments, the PDL1-binding molecule of the invention, in addition to the at least one immunoglobulin single variable domain that can specifically bind to PDL1, further comprises an immunoglobulin Fc region. Inclusion of an immunoglobulin Fc region in the PDL1-binding molecule of the invention allows the binding molecule to form dimmers, and also allows extension of the in vivo half-life of said molecule. Fc region that can be used in the invention may be derived from immunoglobulins of different subtypes, such as IgG (e.g, IgG1, IgG2, IgG3 or IgG4 subtype), IgA1, IgA2, IgD, IgE or IgM.

In some embodiments, mutations can be introduced into wildtype Fc sequence for altering relevant activities mediated by Fc. Said mutations include, but not limited to, a) mutations altering CDC activity mediated by Fc; b) mutations altering ADCC activity mediated by Fc; or c) mutations altering in vivo half-life mediated by FcRn. Such mutation are described in Leonard G Presta, Current Opinion in Immunology 2008, 20:460-470; Esohe E. Idusogie et al., J Immunol 2000, 164: 4178-4184; RAPHAEL A. CLYNES et al., Nature Medicine, 2000, Volume 6, Number 4: 443-446; Paul R. Hinton et al., J Immunol, 2006, 176:346-356.

In some embodiments, mutations may be introduced into Fc sequence such that the mutated Fc more tends to form homo-dimmers or hetero-dimmers. For example, Ridgway, Presta et al. 1996 and Carter 2001 mentioned using the knob-hole model of the spatial interaction of amino acid side chain groups on Fc contacting interface to allow different Fc mutants to form hetero-dimmers more readily; in addition, CN 102558355A or CN 103388013A discloses to allow different Fc mutants to form hetero-dimmers more readily, or Fcs with same mutations to form homo-dimmers more readily, by changing the charges of the amino acids on Fc contacting interface which in turn changes the ionic interaction at the Fc contacting interface.

Preferably, said immunoglobulin Fc region is an Fc region of human immunoglobulin, more preferably an Fc region of human IgG1. In some specific embodiments, the amino acid sequence of the immunoglobulin Fc region is set forth in SEQ ID NO:38. In some specific embodiments, the amino acid sequence of the immunoglobulin Fc region is set forth in SEQ ID NO:70 or 71.

In some specific embodiments, the PDL1-binding molecule of the invention comprising an immunoglobulin Fc region comprises an amino acid sequence selected from SEQ ID NO:39-51 and 72-83.

In another aspect, the PDL1-binding molecule of the invention also encompasses an anti-PDL1 antibody molecule that binds to the same epitope as a VHH consisting of the amino acid sequence of any one of SEQ ID NOs:25-32.

The PDL1-binding molecule of the invention has at least one of the following features:
(a) binding to human PDL1 with a KD of less than $1\times10^{-7}$ M;
(b) blocking the interaction between PDL1 and PD-1;
(c) enhancing activation of PBMCs and/or T cells:
(d) inhibiting tumor growth.

The PDL1-binding molecule of the invention may bind to PDL1 with a KD of less than $1\times10^{-7}$ M, preferably less than $1\times10^{-8}$ M, more preferably less than $1\times10^{-9}$ M, more preferably less than $1\times10^{-10}$ M, and even more preferably less than $1\times10^{-11}$ M.

In some embodiments, the PDL1-binding molecule of the invention can specifically bind to human PDL1 and block the interaction between PDL1 and PD-1. In some embodiments, the PDL1-binding molecule of the invention can specifically bind to human PDL1 and block the interaction between PDL1 and CD80.

The PDL1-binding molecule of the invention can inhibit tumor growth by at least about 10%, preferably at least about 20%, more preferably at least about 30%, more preferably at least about 40%, more preferably at least about 50%, more preferably at least about 60%, more preferably at least about 70%, and more preferably at least about 80%.

Furthermore, the PDL1-binding molecule of the invention is resistant to alkali treatment and oxidation treatment. For example, the PDL1-binding molecule of the invention maintains its activity after treatment with strong base (such as 500 mM ammonium bicarbonate) for about 8 hours, preferably about 16 hours, more preferably about 24 hours or more preferably about 32 hours. Alternatively, the PDL1-binding molecule of the invention maintains its activity after treatment with oxidant (1% hydrogen peroxide) for about 2 hours, preferably about 4 hours, or more preferably about 8 hours.

In addition, the PDL1-binding molecule of the invention is stable at high concentration. For example, the PDL1-binding molecule of the invention keeps stable at a concentration of about 100 mg/ml, more preferably about 150 mg/ml, more preferably about 200 mg/ml or more preferably about 250 mg/ml without forming aggregates.

Nucleic Acid, Vector and Host Cell

In another aspect, the invention relates to nucleic acid molecule that encodes the PDL1-binding molecules of the invention. A nucleic acid of the invention may be RNA, DNA or cDNA. According to one embodiment of the invention, the nucleic acid of the invention is in essentially isolated form. In some specific embodiments, nucleic acid molecule encoding the PDL1-binding molecules of the invention comprises a nucleotide sequence of any one of SEQ ID NOs:58-65.

The nucleic acid of the invention may also be in the form of, may be present in and/or may be part of a vector, such as for example a plasmid, cosmid or YAC. The vector may especially be an expression vector, i.e. a vector that can provide for expression of the PDL1-binding molecule in vitro and/or in vivo (i.e. in a suitable host cell, host organism and/or expression system). Such expression vector generally comprises at least one nucleic acid of the invention that is operably linked to one or more suitable regulatory elements, such as promoter(s), enhancer(s), terminator(s), and the like. Such elements and their selection in view of expression of a specific sequence in a specific host are common knowledge of the skilled person. Specific examples of regulatory elements and other elements useful or necessary for expressing PDL1-binding molecules of the invention include such as promoters, enhancers, terminators, integration factors, selection markers, leader sequences, reporter genes, and the like.

The nucleic acids of the invention may be prepared or obtained in a manner known per se (e.g. by automated DNA synthesis and/or recombinant DNA technology), based on the information on the amino acid sequences for the polypeptides of the invention given herein, and/or can be isolated from a suitable natural source.

In another aspect, the invention relates to host cells that express or are capable of expressing one or more PDL1-binding molecule of the invention; and/or that contain a nucleic acid of the invention. According to a particularly preferred embodiment, said host cells are bacterial cells; other useful cells are yeast cells, fungal cells or mammalian cells.

Suitable bacterial cells include cells from gram-negative bacterial strains such as strains of *Escherichia coli, Proteus*, and *Pseudomonas*, and gram-positive bacterial strains such as strains of *Bacillus, Streptomyces, Staphylococcus*, and *Lactococcus*. Suitable fungal cell include cells from species of *Trichoderma, Neurospora*, and *Aspergillus*.

Suitable fungal cell include cells from species of *Trichoderma, Neurospora*, and *Aspergillus*. Suitable yeast cells include cells from species of *Saccharomyces* (for example, *Saccharomyces cerevisiae*), *Schizosaccharomyces* (for example, *Schizosaccharomyces pombe*), *Pichia* (for example, *Pichia pastoris* and *Pichia methanolica*), and *Hansenula*.

Suitable mammalian cells include for example HEK293 cells, CHO cells, BHK cells, HeLa cells, COS cells, and the like.

However, amphibian cells, insect cells, plant cells, and any other cells used in the art for the expression of heterologous proteins can be used as well.

The invention further provides methods of manufacturing a PDL1-binding molecule of the invention, such methods generally comprise the steps of:
  culturing host cells of the invention under conditions that allow expression of the PDL1-binding molecule of the invention; and
  recovering the PDL1-binding molecule expressed by the host cells from the culture; and
  optionally further purifying and/or modifying the PDL1-binding molecule of the invention.

In a preferred embodiment, the PDL1-binding molecule of the invention is produced by using mammalian cells. The PDL1-binding molecule of the invention can achieve high expression in mammalian cells. For example, the expression level can be up to about 5 g/L, preferably about 6 g/L, preferably about 7 g/L, preferably about 8 g/L, preferably about 9 g/L, preferably about 10 g/L or higher.

PDL1-binding molecules of the invention may be produced in a cell as set out above either intracellullarly (e.g. in the cytosol, in the periplasma or in inclusion bodies) and then isolated from the host cells and optionally further purified; or they can be produced extracellularly (e.g. in the medium in which the host cells are cultured) and then isolated from the culture medium and optionally further purified.

Methods and reagents used for the recombinant production of polypeptides, such as specific suitable expression vectors, transformation or transfection methods, selection markers, methods of induction of protein expression, culture conditions, and the like, are known in the art. Similarly, protein isolation and purification techniques useful in a method of manufacture of a PDL1-binding molecule of the invention are well known to the skilled person.

However, the PDL1-binding molecules of the invention can also be obtained by other methods for production of proteins known in the art, such as, chemical synthesis, including solid phase or liquid phase synthesis.

Immunoconjugate

In another aspect, the present invention features relates to a PDL1-binding molecule conjugated to a therapeutic moiety, such as a cytotoxin, a biologically active protein or a radioisotoperadiotoxin. Such conjugates are referred to herein as "immunococonjugates". Immunoconjugates that include one or more cytotoxins are referred to as "immunotoxins." A cytotoxin or cytotoxic agent includes any agent that is detrimental to (e.g., kills) cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof.

Therapeutic agents that can be conjugated also include, for example, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

Other preferred examples of therapeutic cytotoxins that can be conjugated to PDL1-binding molecule of the invention include duocarmycins, calicheamicins, maytansines and auristatins, and derivatives thereof.

Cytotoxins can be conjugated to PDL1-binding molecule of the invention using linker technology available in the art. Examples of linker types that have been used to conjugate a cytotoxin to PDL1-binding molecule include, but are not limited to, hydrazones, thioethers, esters, disulfides and peptide-containing linkers. A linker can be chosen that is, for example, susceptible to cleavage by low pH within the lysosomal compartment or susceptible to cleavage by proteases, such as proteases preferentially expressed in tumor tissue such as cathepsins (e.g., cathepsins B, C, D).

For further discussion of types of cytotoxins, linkers and methods for conjugating therapeutic agents to antibodies, see also Saito, G. etal. (2003) Adv. DrugDeliv. Rev. 55:199-215; Trail, P. A. et al. (2003) Cancer Immunol. Immunother. 52:328-337; Payne, G. (2003) Cancer Cell 3:207-212; Allen, T. M. (2002) Not. Rev. Cancer 2:750-763; Pastan, I. and Kreitman, R. J. (2002) Curr. Opin. Imestig. Drugs 3:1089-1091; Senter, P. D. and Springer, C J. (200Y) Adv. Drug Deliv. Rev. 53:247-264.

PDL1-binding molecule of the present invention also can be conjugated to a radioactive isotope to generate cytotoxic radiopharmaceuticals, also referred to as radioimmunoconjugates. Examples of radioactive isotopes that can be conjugated to antibodies for use diagnostically or therapeutically include, but are not limited to, iodine$^{131}$, indium$^{111}$, yttrium$^{90}$ and lutetium$^{177}$. Methods for preparing radioimmunoconjugates are established in the art. Examples of radioimmunoconjugates are commercially available, including Zevalin™ (IDEC Pharmaceuticals) and Bexxar™ (Corixa Pharmaceuticals), and similar methods can be used to prepare radioimmunoconjugates using the PDL1-binding molecule of the invention.

The PDL1-binding molecule of the invention can also be conjugated to a protein with desired biological activity to modify a given biological response. Such proteins may include, for example, an enzymatically active toxin, or active fragment thereof, such as abrin, ricin A, *pseudomonas* exotoxin, or diphtheria toxin; a protein such as tumor necrosis factor or interferon-γ; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other immune factors such as IFN.

Techniques for conjugating such therapeutic moiety to antibodies are well known, see, e.g., Arnon et al., "Monoclonal Antibodies For Immunotargeting Of Drugs In Cancer Therapy", Monoclonal Antibodies And Cancer Therapy, Reisfeld et al. (ed.), pp. 243-56 (Alan R. Liss, Inc. 1985); Hellstrom et al., "Antibodies For Drug Delivery", Controlled Drug Delivery (2nd Ed.), Robinson et al. (ed.), pp. 623-53 (Marcel Dekker, Inc.1987); Thorpe, "Antibody Carriers Of Cytotoxic Agents In Cancer Therapy: A Review", Monoclonal Antibodies'84: Biological And Clinical Applications, Pinchera et al. (ed.), pp. 475-506 (1985); "Analysis, Results, And Future Prospective Of The Therapeutic Use Of Radiolabeled Antibody In Cancer Therapy", Monoclonal Antibodies For Cancer Detection And Therapy, Baldwin et al. (ed.), pp. 303-16 (Academic Press 1985), and Thorpe et al., "The Preparation And Cytotoxic Properties Of Antibody-Toxin Conjugates" Immunol. Rev., 62: 119-58 (1982).

Pharmaceutical Compositions

In another aspect, the present invention provides a composition, e.g., a pharmaceutical composition, containing one or a combination of PDL1-binding molecule of the present invention, formulated together with a pharmaceutically acceptable carrier. Such compositions may include one or a combination of (e.g., two or more different) PDL1-binding molecules of the invention, or immunoconjugates of the invention. For example, a pharmaceutical composition of the invention can comprise a combination of antibody molecules that bind to different epitopes on the target antigen.

Pharmaceutical compositions of the invention also can be administered in combination therapy, i.e., combined with other agents. For example, the combination therapy can include a PDL1-binding molecule of the present invention combined with at least one other anti-tumor agent. For example, PDL1-binding molecule of the invention may be administered in combination with antibodies targeting other tumor-specific antigens. Said antibodies targeting other tumor-specific antigens include, but are not limited to anti-EGFR antibody, anti-EGFR variant antibody, anti-VEGFa antibody, anti-HER2 antibody, or anti-CMET antibody. Preferably, said antibodies are monoclonal.

As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g., by injection or infusion). Depending on the route of administration, the active compound, i.e., antibody, or immunoconjugate, may be coated in a material to protect the compound from the action of acids and other natural conditions that may inactivate the compound.

The pharmaceutical compounds of the invention may include one or more pharmaceutically acceptable salts. A "pharmaceutically acceptable salt" refers to a salt that retains the desired biological activity of the parent compound and does not impart any undesired toxicological effects (see e.g., Berge, S. M., et al. (1977) J. Pharm. Sci. 66:1-19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

A pharmaceutical composition of the invention also may include a pharmaceutically acceptable anti-oxidant. Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

These compositions may also contain adjuvants such as preservatives, wetting agents, emulsifying agents and dispersing agents.

Prevention of presence of microorganisms may be ensured both by sterilization procedures, supra, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the invention is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

The amount of active ingredient which can be combined with a carrier material to produce a single dosage form will vary depending upon the subject being treated, and the particular mode of administration. The amount of active ingredient which can be combined with a carrier material to produce a single dosage form will generally be that amount of the composition which produces a therapeutic effect.

Generally, out of one hundred percent, this amount will range from about 0.01 percent to about ninety-nine percent of active ingredient, preferably from about 0.1 percent to about 70 percent, most preferably from about 1 percent to about 30 percent of active ingredient in combination with a pharmaceutically acceptable carrier.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

For administration of the antibody molecule, the dosage ranges from about 0.0001 to 100 mg/kg, and more usually 0.01 to 5 mg/kg, of the subject body weight. For example dosages can be 0.3 mg/kg body weight, 1 mg/kg body weight, 3 mg/kg body weight, 5 mg/kg body weight, 10 mg/kg body weight or 20 mg/kg body weight or within the range of 1-20 mg/kg. An exemplary treatment regime entails administration once per week, once every two weeks, once every three weeks, once every four weeks, once a month, once every 3 months or once every three to 6 months, or with a short administration interval at the beginning (such as once per week to once every three weeks), and then an extended interval later (such as once a month to once every three to 6 months).

Alternatively, antibody can be administered as a sustained release formulation, in which case less frequent administration is required. Dosage and frequency vary depending on the half-life of the antibody in the patient. In general, human antibodies show the longest half life, followed by humanized antibodies, chimeric antibodies, and nonhuman antibodies. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patient can be administered a prophylactic regime.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

A "therapeutically effective amount" of a PDL1-binding molecule of the invention preferably results in a decrease in severity of disease symptoms, an increase in frequency and duration of disease symptom-free periods, or a prevention of impairment or disability due to the disease affliction. For example, for the treatment of PDL1 relating tumors, a "therapeutically effective amount" preferably inhibits cell growth or tumor growth by at least about 10%, at least about 20%, more preferably by at least about 40%, even more preferably by at least about 60%, and still more preferably by at least about 80% relative to untreated subjects. The ability to inhibit tumor growth can be evaluated in an animal model system predictive of efficacy in human tumors. Alternatively, this property of a composition can be evaluated by examining the ability of the compound to inhibit cell growth; such inhibition can be determined in vitro by assays known to the skilled practitioner. A therapeutically effective amount of a therapeutic compound can decrease tumor size, or otherwise ameliorate symptoms in a subject. One of ordinary skill in the art would be able to determine such amounts based on such factors as the subject's size, the severity of the subject's symptoms, and the particular composition or route of administration selected.

A composition of the present invention can be administered via one or more routes of administration using one or more of a variety of methods known in the art. As will be appreciated by the skilled artisan, the route and/or mode of administration will vary depending upon the desired results. Preferred routes of administration for PDL1-binding molecules of the invention include intravenous, intramuscular, intradermal, intraperitoneal, subcutaneous, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Alternatively, a PDL1-binding molecule of the invention can be administered via a non-parenteral route, such as a topical, epidermal or mucosal route of administration, for example, intranasally, orally, vaginally, rectally, sublingually or topically.

The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., Sustained and Controlled Release Drug Delivery Systems, J. R. Robinson, ed., Marcel Dekker, Inc., New York, 1978.

Therapeutic compositions can be administered with medical devices known in the art. For example, in a preferred embodiment, a therapeutic composition of the invention can be administered with a needleless hypodermic injection device, such as the devices disclosed in U.S. Pat. No. 5,399,163; 5,383,851; 5,312,335; 5,064,413; 4,941,880; 4,790,824; or 4,596,556. Examples of well-known implants and modules useful in the present invention include: U.S. Pat. No. 4,487,603, which discloses an implantable microinfusion pump for dispensing medication at a controlled rate; U.S. Pat. No. 4,486,194, which discloses a therapeutic device for administering medicaments through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. These patents are incorporated herein by reference. Many other such implants, delivery systems, and modules are known to those skilled in the art.

In certain embodiments, the PDL1-binding molecules of the invention can be formulated to ensure proper distribution in vivo. For example, the blood-brain barrier (BBB) excludes many highly hydrophilic compounds. To ensure that the therapeutic compounds of the invention cross the BBB (if desired), they can be formulated, for example, in liposomes. For methods of manufacturing liposomes, see, e.g., U.S. Pat. Nos. 4,522,811; 5,374,548; and 5,399,331. The liposomes may comprise one or more moieties which are selectively transported into specific cells or organs, thus enhance targeted drug delivery (see, e.g., V. V. Ranade (1989) J. Clin. Pharmacol. 29:685). Exemplary targeting moieties include folate or biotin (see, e.g., U.S. Pat. No. 5,416,016 to Low et al); mannosides (Umezawa et al., (1988) Biochem. Biophys. Res. Commun. 153:1038): antibodies (P. G. Bloeman et al. (1995) FEBS Lett. 357:140; M. Owais et al. (1995) Antimicrob. Agents Chemother. 39:180); surfactant protein A receptor (Briscoe et al. (1995) Am. J. Physiol. 1233: 134); p120 (Schreier et al. (1994) J Biol. Chem. 269:9090): see also K. Keinanen; M. L. Laukkanen (1994) FEBS Lett. 346:123; J J. Killion; L J. Fidler (1994) Immunomethods 4:273.

Preventing and Treating of Diseases

In another aspect, the present invention provides the use of the PDL1 binding molecule, nucleic acid, host cell, immunoconjugate and pharmaceutical composition of the invention for preventing and/or treating PDL1 relating diseases, as well as the corresponding methods. PDL1 relating diseases that can be prevented and/or treated with the PDL1 binding molecule of the invention are described in detailed as follows.

Cancer

Blocking PDL1 by PDL1-binding molecule of the invention can enhance the immune response to cancerous cells in the patient. PDL1 is not expressed in normal human cells, but is abundant in a variety of human cancers (Dong et al. (2002) Nat Med 8:787-9). The interaction between PD-1 and PDL1 results in a decrease in tumor infiltrating lymphocytes, a decrease in T-cell receptor mediated proliferation, and immune evasion by the cancerous cells (Dong et al. (2003) J Mol Med 81:281-7; Blank et al. (2004) Cancer Immunol. Immunother. [epub]; Konishi et al. (2004) Clin. Cancer Res. 10:5094-100). Immune suppression can be reversed by inhibiting the local interaction of PDL1 to PD-1 and the effect is additive when the interaction of PD-L2 to PD-1 is blocked as well (Iwai et al. (2002) PNAS 99:12293-7; Brown et al. (2003) J. Immunol. JTO: 1257-66). A PDL1-binding molecule of the invention may be used alone to inhibit the growth of cancerous tumors. Alternatively, a PDL1-binding molecule of the invention may be used in conjunction with other immunogenic agents, standard cancer treatments, or other antibodies, as described below.

Accordingly, in one embodiment, the invention provides a method of preventing or treating cancer in a subject, comprising administering to the subject a therapeutically effective amount of PDL1-binding molecule of the invention so as to inhibit growth of tumor cells in the subject.

Preferred cancers whose growth may be inhibited using the antibodies of the invention include cancers typically responsive to immunotherapy. Non-limiting examples of preferred cancers for treatment include lung cancer, ovarian cancer, colon cancer, rectal cancer, melanoma (e.g., metastatic malignant melanoma), renal cancer, bladder cancer, breast cancer, liver cancer, lymphoma, hematological malignancy, head and neck cancer, glioma, gastric cancer, nasopharyngeal cancer, laryngeal cancer, cervical cancer, corpus carcinoma, osteosarcoma. Examples of other cancers that may be treated using the methods of the invention include bone cancer, pancreatic cancer, prostatic cancer, skin cancer, cancer of the head or neck, cutaneous or intraocular malignant melanoma, uterine cancer, cancer of the anal region, testicular cancer, carcinoma of the fallopian tubes, carcinoma of the endometrium, carcinoma of the cervix, carcinoma of the vagina, carcinoma of the vulva, Hodgkin's Disease, non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemia including acute myeloid leukemia, chronic myeloid leukemia, acute lymphoblastic leukemia, chronic lymphocytic leukemia, solid tumors of childhood, lymphocytic lymphoma, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers including those induced by asbestos, and combinations of said cancers. The present invention is also useful for treatment of metastatic cancers, especially metastatic cancers that express PDL1 (Iwai et al. (2005) Int. Immunol. 17:133-144).

Optionally. PDL1-binding molecule of the invention can be combined with an immunogenic agent, such as cancerous cells, purified tumor antigens (including recombinant proteins, peptides, and carbohydrate molecules), cells, and cells transfected with genes encoding immune stimulating cytokines (He et al. (2004) J. Immunol. 173:4919-28). Non-limiting examples of tumor vaccines that can be used include peptides of melanoma antigens, such as peptides of gp100, MAGE antigens, Trp-2, MARTI and/or tyrosinase, or tumor cells transfected to express the cytokine GM-CSF.

In humans, some tumors have been shown to be immunogenic such as melanomas. It is anticipated that by raising the threshold of T cell activation by PDL1 blockade with PDL1-binding molecule of the invention, it is possible to activate tumor responses in the host. PDL1 blockade (such as PDL1 antibody, e.g., the PDL1-binding molecule of the invention) is likely to be most effective when combined with a vaccination protocol. Many experimental strategies for vaccination against tumors have been devised (see Rosenberg, S., 2000, Development of Cancer Vaccines, ASCO Educational Book Spring: 60-62; Logothetis, C, 2000, ASCO Educational Book Spring: 300-302; Khayat, D. 2000, ASCO Educational Book Spring: 414-428; Foon, K. 2000, ASCO Educational Book Spring: 730-738; see also Restifo, N. and Sznol, M., Cancer Vaccines, Ch. 61, pp. 3023-3043 in DeVita, V. et al. (eds.), 1997, Cancer: Principles and Practice of Oncology. Fifth Edition). In one of these strategies, a vaccine is prepared using autologous or allogeneic tumor cells. These cellular vaccines have been shown to be most effective when the tumor cells are transduced to express GM-CSF. GM-CSF has been shown to be a potent activator of antigen presentation for tumor vaccination (Dranoff et al. (1993) Proc. Natl. Acad. Sd U.S.A. 90: 3539-43).

The study of gene expression and large scale gene expression patterns in various tumors has led to the definition of so-called tumor specific antigens (Rosenberg, S A (1999) Immunity 10: 281-7). In many cases, these tumor specific antigens are differentiation antigens expressed in the tumors and in the cell from which the tumor arose, for example melanocyte antigens gp100, MAGE antigens, and Trp-2. More importantly, many of these antigens can be shown to be the targets of tumor specific T cells found in the host. PDL1-binding molecule of the invention may be used in conjunction with a collection of recombinant proteins and/or peptides expressed in a tumor in order to generate an immune response to these proteins. These proteins are normally viewed by the immune system as self antigens and are therefore tolerant to them. The tumor antigen may also include the protein telomerase, which is required for the synthesis of telomeres of chromosomes and which is expressed in more than 85% of human cancers and in only a limited number of somatic tissues (Kim, N et al. (1994) Science 266: 2011-2013). Tumor antigen may also be "neoantigens" expressed in cancer cells because of somatic mutations that alter protein sequence or create fusion proteins between two unrelated sequences (i.e. bcr-abl in the Philadelphia chromosome).

Other tumor vaccines may include the proteins from viruses implicated in human cancers such a Human Papilloma Viruses (HPV), Hepatitis Viruses (HBV and HCV) and Kaposi's Herpes Sarcoma Virus (KHSV). Another form of tumor specific antigen which may be used in conjunction with PDL1 blockade (such as PDL1 antibody, e.g., PDL1-binding molecule of the invention) is purified heat shock proteins (HSP) isolated from the tumor tissue itself. These heat shock proteins contain fragments of proteins from the tumor cells and these HSPs are highly efficient at delivery to antigen presenting cells for eliciting tumor immunity (Suot, R & Srivastava, P (1995) Science 269: 1585-1588; Tamura, Y. et al. (1997) Science 278:117-120).

Dendritic cells (DCs) are potent antigen presenting cells that can be used to prime antigen-specific responses. DCs can be produced ex vivo and loaded with various protein and peptide antigens as well as tumor cell extracts (Nestle, F. et al. (1998) Nature Medicine 4: 328-332). DCs may also be transduced by genetic means to express these tumor antigens as well. DCs have also been fused directly to tumor cells for the purposes of immunization (Kugler, A. et al. (2000) Nature Medicine 6:332-336). As a method of vaccination, DC immunization may be effectively combined with PDL1 blockade (such as PDL1 antibody, e.g., PDL1-binding molecule of the invention) to activate more potent anti-tumor responses.

CAR-T (Chimeric Antigen Receptor T-Cell Immunotherapy) is another cell therapy for treating tumors. Chimeric Antigen Receptor T-Cell (CAR-T cells) are T cells from a patient that have been genetically infected with a chimeric protein of an antigen-binding moiety of an antibody against certain tumor antigen coupled with CD3-ζchain or intracellular portion of FcεRIγ for expressing a chimeric antigen receptor (CAR). Also, co-stimulate signaling sequence may be introduced for increasing cytotoxic activity, proliferation and survival of T cells, and promoting the release of cytokines. After reprogramming, T cells from the patient expanded in vitro to produce a large number tumor-specific CAR-T cells which are then transfused back into the patient for treating tumor. PDL1 blocking agents (such as PDL1 antibodies, e.g., the PDL1 binding molecule of the invention) may be used in combination with CAR-T cell therapy for activate stronger anti-tumor response.

PDL1-binding molecule of the invention may also be combined with standard cancer treatments. PDL1-binding molecule of the invention may be effectively combined with chemotherapeutic regimes. In these instances, it may be possible to reduce the dose of chemotherapeutic reagent administered (Mokyr, M. et al. (1998) Cancer Research 58: 5301-5304). An example of such a combination is an anti-PDL1 antibody in combination with decarbazine for the treatment of melanoma. Another example of such a combination is an anti-PDL1 antibody in combination with interleukin-2 (IL-2) for the treatment of melanoma. The scientific rationale behind the combined use of PDL1-binding molecule of the invention and chemotherapy is that cell death, that is a consequence of the cytotoxic action of most chemotherapeutic compounds, should result in increased levels of tumor antigen in the antigen presentation pathway. Other combination therapies that may result in synergy with PDL1 blockade through cell death are radiation, surgery, and hormone deprivation. Each of these protocols creates a source of tumor antigen in the host. Angiogenesis inhibitors may also be combined with PDL1-binding molecule of the invention. Inhibition of angiogenesis leads to tumor cell death which may feed tumor antigen into host antigen presentation pathways.

The PDL1 binding molecule of the invention can also be used in combination with antibody against other tumor-specific antigen. Said antibody against other tumor-specific antigen includes but not limited to anti-EGFR antibody, anti-EGFR variant antibody, anti-VEGFa antibody, anti-HER2 antibody, or anti-CMET antibody. Preferably, said antibody is an monoclonal antibody.

PDL1-binding molecule of the invention can also be used in combination with bispecific antibodies that target Fc alpha or Fc gamma receptor-expressing effectors cells to tumor cells (see, e.g., U.S. Pat. Nos. 5,922,845 and 5,837, 243). Bispecific antibodies can be used to target two separate antigens. For example anti-Fc receptor/anti tumor antigen (e.g., Her-2/neu) bispecific antibodies have been used to target macrophages to sites of tumor. This targeting may more effectively activate tumor specific responses. The T cell arm of these responses would by augmented by the use of PDL1 blockade. Alternatively, antigen may be delivered directly to DCs by the use of bispecific antibodies which bind to tumor antigen and a dendritic cell specific cell surface marker.

Tumors evade host immune surveillance by a large variety of mechanisms. Many of these mechanisms may be overcome by the inactivation of proteins which are expressed by the tumors and which are immunosuppressive. These include among others TGF-beta (Kehrl, J. et al. (1986) J. Exp. Med. 163: 1037-1050), IL-10 (Howard, M. & O'Garra, A. (1992) Immunology Today 13: 198-200), and Fas ligand (Hahne, M. et al. (1996) Science 274: 1363-1365). Antibodies to each of these entities may be used in combination with PDL1-binding molecule of the invention to counteract the effects of the immunosuppressive agent and favor tumor immune responses by the host.

Other antibodies which may be used to activate host immune responsiveness can be used in combination with anti-PDL1. These include molecules on the surface of dendritic cells which activate DC function and antigen presentation. Anti-CD40 antibodies are able to substitute effectively for T cell helper activity (Ridge, J. et al. (1998) Nature 393: 474-478) and can be used in conjunction with PDL1-binding molecule of the invention (Ito, N. et al. (2000) Immunobiology 201 (5) 527-40). Activating antibodies to T cell costimulatory molecules such as OX-40 (Weinberg, A. et al. (2000) Immunol 164: 2160-2169), 4-1BB (Melero, I. et al. (1997) Nature Medicine 3: 682-685 (1997), and ICOS (Hutloff. A. et al. (1999) Nature 397: 262-266) as well as antibodies which block the activity of negative costimulatory molecules such as CTLA-4 (e.g., U.S. Pat. No. 5,811, 097) or BTLA (Watanabe, N. et al. (2003) Nat Immunol 4:670-9). B7-H4 (Sica, G L et al. (2003) Immunity 18:849-61) may also provide for increased levels of T cell activation.

Bone marrow transplantation is currently being used to treat a variety of tumors of hematopoietic origin. While graft versus host disease is a consequence of this treatment, therapeutic benefit may be obtained from graft vs. tumor responses. PDL1 blockade can be used to increase the effectiveness of the donor engrafted tumor specific T cells. There are also several experimental treatment protocols that involve ex vivo activation and expansion of antigen specific T cells and adoptive transfer of these cells into recipients in order to antigen-specific T cells against tumor (Greenberg, R. & Riddell, S. (1999) Science 285: 546-51). These methods may also be used to activate T cell responses to infectious agents such as CMV. Ex vivo activation in the presence of PDL1-binding molecule of the invention may be expected to increase the frequency and activity of the adoptively transferred T cells.

Infectious Diseases

Other methods of the invention are used to treat patients that have been exposed to particular toxins or pathogens. Accordingly, another aspect of the invention provides a method of preventing or treating an infectious disease in a subject comprising administering to the subject a PDL1-binding molecule of the invention, such that the subject is treated for the infectious disease.

Similar to its application to tumors as discussed above, PDL1 blockade can be used alone, or as an adjuvant, in combination with vaccines, to stimulate the immune response to pathogens, toxins, and self-antigens. Examples of pathogens for which this therapeutic approach may be particularly useful, include pathogens for which there is currently no effective vaccine, or pathogens for which conventional vaccines are less than completely effective. These include, but are not limited to HTV, Hepatitis (A, B, & C). Influenza, Herpes, Giardia, Malaria, Leishmania, *Staphylococcus aureus, Pseudomonas Aeruginosa*. PDL1 blockade is particularly useful against established infections by agents such as HIV that present altered antigens over the course of the infections. These novel epitopes are recognized as foreign at the time of anti-human PDL1 administration, thus provoking a strong T cell response that is not dampened by negative signals through PDL1.

Some examples of pathogenic viruses causing infections treatable by methods of the invention include HIV, hepatitis (A, B, or C), herpes virus (e.g., VZV, HSV-1, HAV-6, HSV-II, and CMV, Epstein Barr virus), adenovirus, influenza virus, flaviviruses, echovirus, rhinovirus, coxsackie virus, cornovirus, respiratory syncytial virus, mumps virus, rotavirus, measles virus, rubella virus, parvovirus, vaccinia virus, HTLV virus, dengue virus, papillomavirus, molluscum virus, poliovirus, rabies virus, JC virus and arboviral encephalitis virus.

Some examples of pathogenic bacteria causing infections treatable by methods of the invention include chlamydia, rickettsial bacteria, mycobacteria, staphylococci, streptococci, pneumonococci, meningococci and conococci, *klebsiella, proteus, serratia, pseudomonas, legionella*, diphtheria, *salmonella*, bacilli, cholera, tetanus, botulism, anthrax, plague, leptospirosis, and Lyme's disease bacteria.

Some examples of pathogenic fungi causing infections treatable by methods of the invention include *Candida* (albicans, krusei, glabrata, tropicalis, etc.), *Cryptococcus neoformans, Aspergillus* (fumigatus, niger, etc.), Genus *Mucorales* (mucor, absidia, rhizophus), *Sporothrix schenkii, Blastomyces dermatitidis. Paracoccidioides brasiliensis, Coccidioides immitis* and *Histoplasma capsulatum*.

Some examples of pathogenic parasites causing infections treatable by methods of the invention include *Entamoeba histolytica, Balantidium coli, Naegleria fowleri, Acanthamoeba* sp., *Giardia lambia, Cryptosporidium* sp., *Pneumocystis carinii, Plasmodium vivax, Babesia microti, Trypanosoma brucei, Trypanosoma cruzi, Leishmania donovani, Toxoplasma gondi, Nippostrongylus brasiliensis.*

In all of the above methods. PDL1 blockade can be combined with other forms of immunotherapy such as cytokine treatment (e.g., interferons, GM-CSF, G-CSF, IL-2), or bispecific antibody therapy, which provides for enhanced presentation of tumor antigens (see, e.g., Holliger (1993) Proc. Natl. Acad. Sci USA 90:6444-6448; Poljak (1994) Structure 2:1121-1123).

Autoimmune Reactions

Anti-PDL1 antibodies may provoke and amplify autoimmune responses. Therefore, it is possible to consider using anti-PDL1 blockade in conjunction with various self proteins in order to devise vaccination protocols to efficiently generate immune responses against these self proteins for disease treatment.

For example, Alzheimer's disease involves inappropriate accumulation of Aβ peptide in amyloid deposits in the brain; antibody responses against amyloid are able to clear these amyloid deposits (Schenk et al., (1999) Nature 400: 173-177). Other self proteins may also be used as targets such as IgE for the treatment of allergy and asthma, and TNFa for rheumatoid arthritis. Finally, antibody responses to various hormones may be induced by the use of anti-PDL1 antibody. Neutralizing antibody responses to reproductive hormones may be used for contraception. Neutralizing antibody response to hormones and other soluble factors that are required for the growth of particular tumors may also be considered as possible vaccination targets.

Analogous methods as described above for the use of anti-PDL1 antibody can be used for induction of therapeutic autoimmune responses to treat patients having an inappropriate accumulation of other self-antigens, such as amyloid deposits, including Aβ in Alzheimer's disease, cytokines such as TNFa, and IgE.

Chronic Inflammatory Diseases

Anti-PDL1 antibodies may also be used to treat diseases such as chronic inflammatory diseases, such as lichen planus, a T-cell mediated chronic inflammatory mucocutaneous disease (Youngnak-Piboonratanakit et al. (2004) Immunol Letters 94:215-22). Accordingly, in another aspect the invention provides a method of abrogating chronic inflammatory disease by T cells, comprising administering to the subject a PDL1-binding molecule of the invention.

Vaccine Adjuvant

In one aspect, the invention provides use of PDL1-binding molecule of the invention as vaccine adjuvant. Anti-PDL1 antibodies may be used to stimulate antigen-specific immune responses by coadministration of an anti-PDL1 antibody with an antigen of interest (e.g., a vaccine).

Accordingly, in another aspect the invention provides a method of enhancing an immune response to an antigen in a subject, comprising administering to the subject: (i) the antigen; and (ii) a PDL1-binding molecule of the invention, such that an immune response to the antigen in the subject is enhanced. The antigen can be, for example, a tumor antigen, a viral antigen, a bacterial antigen or an antigen from a pathogen. Non-limiting examples of such antigens include those discussed in the sections above, such as the tumor antigens (or tumor vaccines) discussed above, or antigens from the viruses, bacteria or other pathogens described above.

Detection

In another aspect, the present invention also provides a method for detecting the presence of PDL1 and/or the expression level of PDL1 in a biological sample, comprising: contacting the PDL1-binding molecule of the invention with the biological sample and a control sample under conditions allowing formation of a complex between the PDL1-binding molecule of the invention and PDL1. Then, the formation of the complex is detected, wherein the difference of the complex formation between the biological sample and the control sample indicates the presence of PDL1 and/or the expression level of PDL1 in the sample.

It has been found that PDL1 is over-expressed in various tumors, or tumor or pathogen will lead to high expression of PDL1 in immunological cells near said tumor or the infection sites of the pathogen. Therefore, PDL1 binding molecule of the invention can be used to diagnose PDL1 relating diseases, such PDL1-overexpressing tumors or infectious diseases such virus infection.

In some embodiments, PDL1 binding molecules of the invention are also conjugated with fluorescent dyes, chemicals, polypeptides, enzymes, isotopes, tags and the like which are used for detection or can be detected by other reagents.

Kit

Also within the scope of the present invention are kits comprising the PDL1-binding molecule, immunoconjugate or pharmaceutical composition of the invention and instructions for use. The kit can further contain a least one additional reagent, or one or more additional PDL1-binding molecules of the invention (e.g., binding molecules which bind to different epitopes in PDL1). Kits typically include a label indicating the intended use of the contents of the kit. The term label includes any writing, or recorded material supplied on or with the kit, or which otherwise accompanies the kit.

EXAMPLES

The present invention is further illustrated by the following examples, but the scope of the invention should not be limited to the specific examples in any way.

Example 1: Screen of Heavy Chain Single Domain Antibody Against PDL1

1.1 Library Construction

PDL1-Fc fusion protein (SEQ ID NO:52) for immunization was expressed by CHO cells (pCDNA4, Invitrogen, Cat V86220), purified by Protein A affinity chromatography. One Camelus bactrianus was chosen for immunization. After 4 immunizations, lymphocytes were isolated from 100 ml camel peripheral blood, and total RNA was extracted by RNA Extraction kit (QIAGEN). Extracted RNA was reverse transcribed into cDNA using SUPER-SCRIPT® III FIRST-STRAND SYNTHESIS SUPERMIX kit according to instructions.

Nucleic acid fragments encoding heavy chain antibodies were amplified by nested PCR:

```
First round PCR:
Upstream primer:
                                        (SEQ ID NO: 66)
GTCCTGGCTGCTCTTCTACAAGGC;

Downstream primer:
                                        (SEQ ID NO: 67)
GGTACGTGCTGTTGAACTGTTCC, Second round PCR:
PCR products from first round PCR as template,
Upstream primer:
                                        (SEQ ID NO: 68)
GATGTGCAGCTGCAGGAGTCTGGRGGAGG;

Downstream primer:
                                        (SEQ ID NO: 69)
GGACTAGTGCGGCCGCTGGAGACGGTGACCTGGGT.
```

Target heavy chain single domain antibody nucleic fragments were recovered and cloned into phage display vector pCDisplay-3 (Creative Biolabs, Cat: VPT4023) using endonuclease PstI and NotI (from NEB). The products were then electroporated into E. coli competent cell TG1, and phage display library for heavy chain single domain antibodies against PDL1 was constructed and verified. By plating serial dilutions, library capacity was determined as $1.33 \times 10^8$. To determine the insertion ratio of the library, 24 clones were randomly selected for colony PCR The results revealed an insertion ratio of 100%.

1.2 Panning for Heavy Chain Single Domain Antibody Against PDL1

Multi-well plates were coated with PDL1-Fc fusion protein at 10 μg/well, 4° C. overnight. On next day, after blocking with 1% skim milk at room temperature for 2 hours, 100 μl phages ($8 \times 10^{11}$ tfu, from the phage display library for camel heavy chain single domain antibodies constructed in 1.1) were added, room temperature for 1 hour. Then unbound phages were removed by washing with PBST (0.05% tween 20 in PBS) for 5 times. Phages that specifically bind to PDL1 were dissociated with triethylammonium (100 mM), and used to infect E. coli TG1 of log phase, producing phages which were then purified for next round screen. The same screen was repeated for 3-4 rounds. Thereby, positive clones were enriched, achieving the purpose of selecting PDL1 specific antibodies from the antibody library by phage display technology.

1.3 Specific Selection of Individual Positive Clones by Phage Enzyme-Linked Immunoassay (ELISA)

PDL1 binding positive phages obtained after 3-4 rounds of panning were used to infect blank E. coli and plated. 96 single colonies were randomly selected for culturing, and phages were produced and purified respectively. Plates were coated with PDL1-Fc fusion protein at 4° C. overnight; sample phages as obtained were added (blank phages as control) and incubated at room temperature for 1 hour. Primary antibody, mouse anti-HA tag antibody (Beijing Kangwei Shiji Biotech. Ltd.), was added after washes and incubated at room temperature, 1 hour for reaction. Secondary antibody, goat anti-mouse alkaline phosphatase labeled antibody (Amyject Scientific Ltd.) was added after washes and incubated at room temperature, 1 hour for reaction. Alkaline phosphatase chromogenic solution was added after washes, and absorption value was read at 405 nm wave length. When the OD of the sample well is 3 times higher than the OD of control well, the sample is determined as positive. Bacteria in the positive wells were transferred to and cultured in LB liquid medium supplemented with 100 μg/ml Ampicillin for plasmid extraction and subsequent sequencing.

The protein sequences of each clone were analyzed according to the sequence alignment software Vector NTI. Clones with the same CDR1, CDR2, and CDR3 sequences are considered as the same antibody, while clones with different CDR sequences are considered as different antibody. A total of 21 different antibodies were finally obtained.

Example 2 Preliminary Evaluation of Heavy Chain Single Domain Antibodies Against PDL1

2.1 Expression of Heavy Chain Single Domain Antibodies in E. coli and Purification Thereof The coding sequences of the 21 heavy chain single domain antibodies obtained by sequencing analysis were subcloned into the expression vector PET32b (Novagen, product number: 69016-3) and the correct recombinant plasmid was transformed into expression host strain BL1 (DE3) (Tiangen Biotech, CB105-02), plated on LB solid medium containing 100 micrograms per milliliter ampicillin overnight at 37° C. Single colonies were inoculated and cultured overnight, transferred in the next day for expansion at 37° C. by shaking. When the culture reached OD value of 0.6-1, 0.5 mM IPTG was added for induction, 28° C. overnight with shaking. The next day, the bacteria were harvested by centrifugation, and lysed to obtain antibody crude extracts. Nickel ion affinity chromatography was then used to purify the antibody proteins, resulting in antibody proteins of more than 90% purity.

2.2 Specific Binding of the Candidate PDL1 Heavy Chain Single Domain Antibody to Human PDL1 Protein Plates were coated with PDL1-Fc fusion protein overnight at 4° C. and 100 ng of the heavy chain single-domain antibody obtained in Example 2.1 (the control was a single domain antibody not binding to the PDL1-Fc protein) was added to each well and allowed to react for 1 hour at room temperature. After washing, primary antibody anti-His tag antibody (purchased from Beijing Kangwei Century Bio-technology Co., Ltd.) was added and reacted for 1 hour at room temperature. After washing, a secondary goat anti-mouse horseradish peroxidase-labeled antibody (Yiqiao Shenzhou, Cat: SSA007200) was added and reacted for 1 hour at room temperature. After washing, chromogenic agent was added and the absorbance was read at 405 nm.

The plates were coated with Fc protein overnight at 4° C. and 100 ng of the heavy chain single domain antibody obtained in Example 2.1 was added to each well (control was a single domain antibody against other unrelated targets) and allowed to react for 1 hour at room temperature. After washing, an anti-rabbit anti-human Fc antibody (purchased from Shanghai Pu Xin Biotechnology Co., Ltd.) was added and reacted for 1 hour at room temperature. After washing, goat anti-rabbit anti-rabbit horseradish peroxidase labeled antibody (purchased from Shanghai Pu Xin Biotechnology Co., Ltd.) was added and reacted at room temperature for 1 hour. After washing, chromogenic agent was added and the absorbance was read at 405 nm.

The candidate antibody is considered as binding to the PDL1-Fc protein when the ratio of the OD value for the PDL1-Fc protein divided by the OD value for the blank control is greater than or equal to 4; and simultaneously, the above antibody capable of binding to PDL1-Fc antigen protein, when the ratio of the OD value for binding to PDL1-Fc divided by the OD value for binding Fc protein is >=5, is considered as specifically binding to the PDL1 moiety rather than the Fc moiety.

The results showed that out of the 21 antibodies, 8 (bold in bold) could specifically bind to PDL1 without binding to Fc. The specific results are shown in the following Table 1:

TABLE 1

|  | OD (against PDL1) | OD (against Fc) | OD (PDL1/Fc) | OD (PDL1/blank) | SEQ ID NO |
|---|---|---|---|---|---|
| PDL1-4 dAb | 2.578 | 2.179 | 1.183111519 | 47.74074074 |  |
| PDL1-8 dAb | 2.38 | 1.398 | 1.702432046 | 44.07407407 |  |
| PDL1-10 dAb | 0.854 | 0.099 | 8.626262626 | 15.81481481 | 25 |
| PDL1-21 dAb | 1.29 | 1.081 | 1.1933395 | 23.88888889 |  |
| PDL1-22 dAb | 0.158 | 0.097 | 1.628865979 | 2.925925926 |  |
| PDL1-27 dAb | 2.62 | 0.08 | 32.75 | 48.51851852 | 26 |
| PDL1-29 dAb | 2.078 | 2.031 | 1.02314131 | 38.48148148 |  |
| PDL1-38 dAb | 1.983 | 0.065 | 30.50769231 | 36.72222222 | 27 |
| PDL1-47 dAb | 0.946 | 2.314 | 0.408815903 | 17.51851852 |  |
| PDL1-56 dAb | 2.931 | 0.068 | 43.10294118 | 54.27777778 | 28 |
| PDL1-64 dAb | 1.321 | 1.247 | 1.059342422 | 24.46296296 |  |
| PDL1-69 dAb | 1.172 | 0.165 | 7.103030303 | 21.7037037 | 29 |
| PDL1-72 dAb | 0.074 | 0.068 | 1.088235294 | 1.37037037 |  |
| PDL1-75 dAb | 1.067 | 0.987 | 1.081053698 | 19.75925926 |  |
| PDL1-76 dAb | 1.931 | 2.805 | 0.688413547 | 35.75925926 |  |
| PDL1-81 dAb | 2.68 | 0.085 | 31.52941176 | 49.62962963 | 30 |
| PDL1-87 dAb | 2.238 | 0.124 | 18.0483871 | 41.44444444 | 31 |
| PDL1-90 dAb | 0.067 | 0.071 | 0.943661972 | 1.240740741 |  |
| PDL1-91 dAb | 1.384 | 1.541 | 0.898118105 | 25.62962963 |  |
| PDL1-94 dAb | 0.875 | 0.085 | 10.29411765 | 16.2037037 | 32 |
| PDL1-96 dAb | 1.293 | 1.982 | 0.652371342 | 23.94444444 |  |
| blank | 0.054 | 0.072 | 0.75 | 1 |  |

2.3 Binding of PDL1 Heavy Chain Single Domain Antibody to Mouse PDL1 Protein

Mouse PDL1-Fc protein (SEQ ID NO: 53) was obtained by expression in HEK293 cells (pCDNA4. Invitrogen, Cat V86220).

The plates were coated overnight at 4° C. with mouse PDL1-Fc fusion protein at 0.5 μg/well and 100 ng of the heavy chain single domain antibody obtained in Example 2.1 (control group is a single domain antibody against other unrelated target) was added and allowed to react under room temperature for 1 hour. After washing, primary antibody anti-His tag antibody was added and reacted at room temperature for 1 hour. After washing, goat anti-mouse horseradish peroxidase labeled antibody was added and reacted for 1 hour at room temperature. After washing, chromogenic agent was added and the absorbance was read at 405 nm. The results are shown in Table 2.

TABLE 2

|  | OD (against mouse PDL1) |
| --- | --- |
| PDL1-4 dAb | 0.115 |
| PDL1-8 dAb | 0.098 |
| PDL1-10 dAb | 0.067 |
| PDL1-21 dAb | 0.087 |
| PDL1-22 dAb | 0.158 |
| PDL1-56 dAb | 0.075 |
| blank | 0.096 |

It can be seen that the heavy chain single domain antibody of human PDL1 of the present invention does not bind to the mouse PDL1-Fc protein.

2.4 Examination of the Blocking Effect of PDL1 Heavy Chain Single-Domain Antibody to the Interaction of PD-1 and PDL1 by Competitive ELISA PDL1-Fc protein and PD1-Fc protein (SEQ ID NO: 54) were obtained by expression in HEK293 cells (pCDNA4, Invitrogen, Cat V86220). Biotinylated protein PD1-Fc-Biotin was obtained using the Thermo Biotinlytion kit.

The plates were coated overnight at 4° C. with PDL1-Fc fusion protein at 0.5 μg/well followed by addition of 100 ng of the heavy chain single domain antibody obtained in Example 2.1 (controls are single domain antibodies against other unrelated targets or simply buffer) and 10 μg of PD1-Fc-Biotin (no antibody or protein was added to the blank group, only an equal volume of buffer was added), and allowed to react for 1 hour at room temperature. SA-HRP (purchased from Sigma) was added and allowed to react for 1 hour at room temperature. After adding chromogenic solution, absorbance was read at 405 nm wavelength. When the sample OD value relative to the control OD value is <0.8, the antibody is considered as possessing blocking effect.

As shown in Table 3, the antibody No. 10, 27, 56, 87 and 81 showed a blocking effect on the PD-1/PDL1 interaction.

TABLE 3

|  | OD |
| --- | --- |
| Control 1 | 2.335 |
| Control 2 | 2.413 |
| blank | 0.079 |
| PDL1-10 | 0.126 |
| PDL1-27 | 0.161 |
| PDL1-56 | 0.129 |
| PDL1-87 | 0.897 |
| PDL1-81 | 0.429 |

2.5 the Blocking Effect of PDL1 Heavy Chain Single-Domain Antibody on PDL1 and PD-1 Interaction on Cell Surface was Investigated by FACS HEK293 cells transiently expressing human PDL1 protein on the membrane (293-PDL1 cells) were obtained by transient transfection of a plasmid carrying human PDL1 full length gene (pCDNA4. Invitrogen, Cat V86220) into human HEK293 cells.

293-PDL1 cells were harvested, resuspended in 0.5% PBS-BSA buffer in a 96-well plate, and the above-mentioned antibodies to be detected were added. Negative controls were also set at the same time, and negative controls were 2 μg of a single domain antibody against other target. 0.3 μg hPD-1-Fc-biotin and eBioscience SA-PE were added to all the samples, and the flow cytometry was performed after staining. The antibody is considered to block the cell-surface interaction of PDL1 and PD-1 if the fluorescence value is shifted to the blank direction as compared to the antibody-free group. In this way, antibodies that block the binding of PDL1 antigen to PD-1 on the cell surface were identified.

The results are shown in FIG. 1, antibody No. 10, 27 and 56 exhibit a blocking effect on the PD-1/PDL1 interaction.

Figure 2:
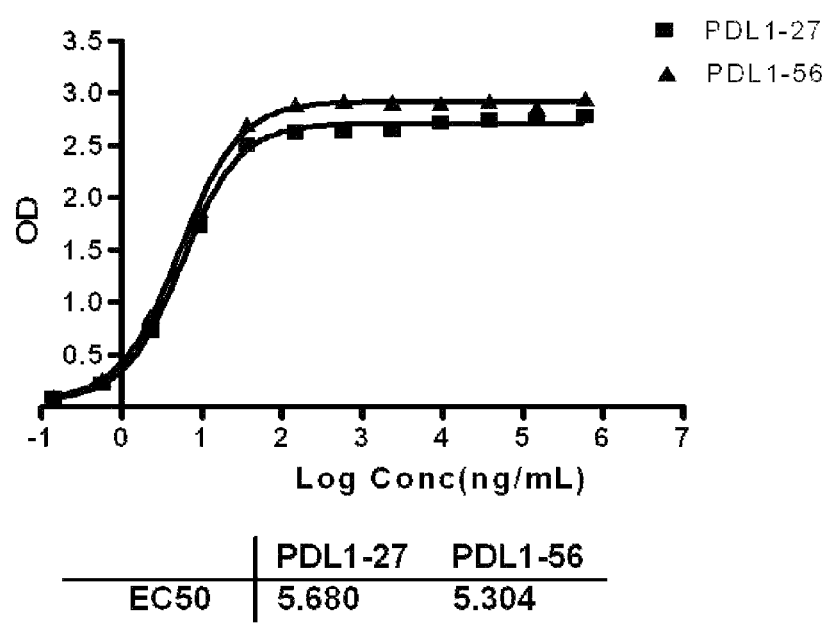
FIG. 2. shows the binding curves of PDL1 heavy chain single domain antibodies to PDL1 antigen protein.

2.6 Binding Curves of PDL1 Heavy Chain Single Domain Antibodies to PDL1 Antigen Protein The plates were coated with the obtained PDL1 heavy chain single-domain antibody at 0.5 μg/well overnight at 4° C. followed by addition of a gradient dilution series of PDL1-Fc fusion protein and allowed to react for 1 hour at room temperature. After washing, goat anti-human IgG-Fc horseradish peroxidase labeled antibody was added and allowed to react for 1 hour at room temperature. After washing, horseradish peroxidase color developing solution was added and the absorbance was read at a wavelength of 405 nm. SotfMax Pro v5.4 was used for data processing and mapping analysis to get binding curve of the antibody to PDL1 and EC50 value (for antibody No. 56 and 27, about 5 ng/ml) through four-parameter fitting. The results are shown in FIG. 2.

2.7 Blocking Curves of PDL1 Heavy Chain Single-Domain Antibodies on the Interaction of PD-1 and PDL1

Plates were coated with PDL1-Fc fusion protein 0.5 μg/well overnight at 4° C. followed by the addition of 100 uL of a gradient dilution series (containing 100 μg/mL PD1-Fc-Biotin) of 100 uL PDL1 blocking single domain antibody Fc fusion protein per well, allowed to react for 1 hour at room temperature. SA-HRP (purchased from Sigma) was added and allowed to react for 1 hour at room temperature. After adding chromogenic solution, absorbance was read at 405 nm wavelength.

Figure 3:
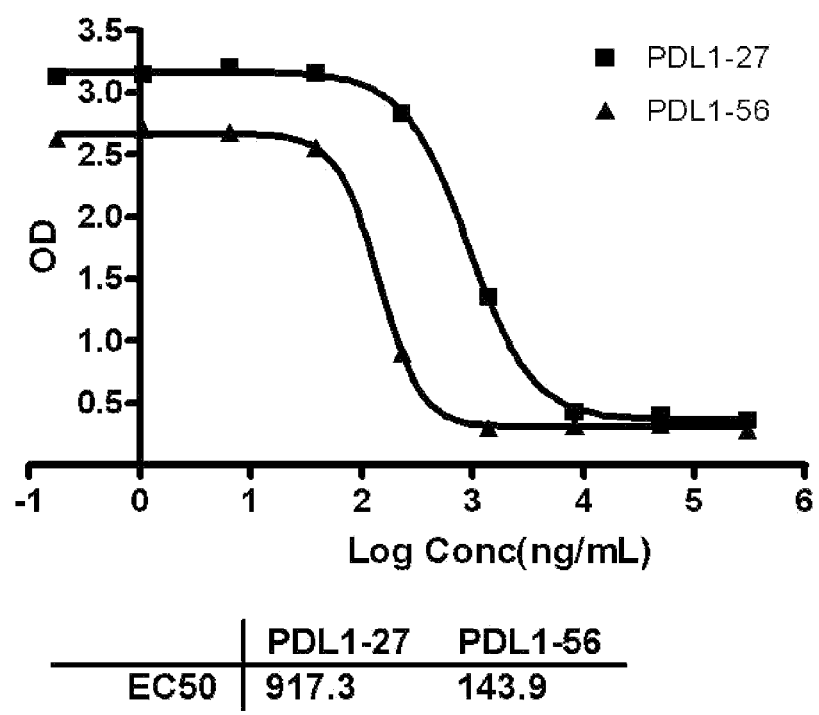
FIG. 3. shows the blocking curves of PDL1 heavy chain single domain antibodies to PD1/PDL1 interaction.

SotfMax Pro v5.4 was used for data processing and mapping analysis to obtain blocking curve and IC50 value of antibody No. 27, 56 to PDL1/PD-1 through four-parameter fitting (IC50 for antibody No. 56 is 143 ng/mL, for antibody No. 27 is approximately 917 ng/ml). The results are shown in FIG. 3.

Example 3 Humanization of PDL1 Single Domain Antibodies

The humanization is performed by the method of protein surface amino acid humanization (resurfacing) and universal framework grafting method for VHH humanization (CDR grafting to a universal framework).

The steps of humanization are as follows: The homologous modeling of antibody No. 56 was performed with the modeling software Modeller9. The reference homologous sequence is NbBcII10 antibody (PDB code: 3DWT), and the relative solvent accessibility of the amino acids is calculated according to the three-dimensional structure of the protein. If one of the amino acids of antibody No. 56 is exposed to a solvent, it was replaced with the amino acid at the same position of the reference human antibody DP-47 sequence, until all substitutions were completed.

Specific steps of universal framework grafting method for VHH humanization are as follows: First, universal humanized VHH framework h-NbBcII10FGLA (PDB code: 3EAK) designed by Cécile Vincke et al. based on sequence homology, the framework was designed based on Nanobody NbBcII10 (PDB code: 3DWT); protein surface amino acid humanization was performed with reference to the human antibody DP-47, and partial amino acids FGLA of VHH sequence framework 2 were modified. We directly used h-NbBcII10FGLA as a framework and replaced the CDRs with the CDR regions of antibody No. 56 to achieve humanization of the antibody.

Figure 4:
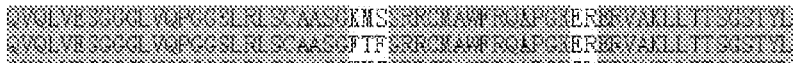
FIG. 4. shows the sequence aligment of five humanized variants of antibody No.5.

The antibody No. 56 was humanized, and five humanized variants of the antibody No. 56 were obtained. Table 4 lists the SEQ ID No of these humanized variants as well as the amino acid changes therein, with amino acid residue numbers following Kabat numbering. FIG. 4 shows the alignment of humanized sequences.

4.2 Preparation of PDL1 Antibodies from MedImmune LLC and Roche

The gene of anti-PDL1 antibody from MedImmune LLC, Inc. was cloned by the method of 2.14H9 in US20130034559 and cloned into the vector pCDNA4. TM004 is Roche's anti-PDL1 antibody. The antibody gene was cloned according to YW243.55.S70.hIgG in US20130045201 A1, and cloned into vector pCDNA4.

The recombinant plasmid was transiently transfected into HEK293 cells by the same method as in Example 4.1, and the resulting anti-PDL1 antibody of MedImmune LLC was renamed as 2.41H90P; Roche's anti-PDL1 antibody was renamed as 243.55.

4.3 Comparison of the Expression of PDL1 Single-Domain Antibody Fc Fusion Protein and the Two Known PDL1 Antibodies Using the same expression system and transient transfection conditions, the expression level of the Fc fusion protein

TABLE 4

| | K27F | M28T | S29F | E44G | R45L | Q71R | N72D | A74S | S76N | K83R | P84A | M89V |
|---|---|---|---|---|---|---|---|---|---|---|---|---|
| Hu56V1 (SEQ ID NO: 33) | ✓ | | | | | ✓ | ✓ | ✓ | ✓ | ✓ | ✓ | ✓ |
| Hu56V2 (SEQ ID NO: 34) | ✓ | ✓ | ✓ | ✓ | | ✓ | ✓ | ✓ | ✓ | ✓ | ✓ | ✓ |
| Hu56V3 (SEQ ID NO: 35) | ✓ | | | | ✓ | ✓ | ✓ | ✓ | ✓ | ✓ | ✓ | ✓ |
| Hu56V4 (SEQ ID NO: 36) | ✓ | ✓ | ✓ | ✓ | ✓ | ✓ | ✓ | ✓ | ✓ | ✓ | ✓ | ✓ |
| Hu56V5 (SEQ ID NO: 37) | ✓ | | | | | ✓ | ✓ | ✓ | ✓ | | ✓ | ✓ |

Example 4 Preparation of PDL1 Blocking Antibody Protein Using Mammalian Cells 4.1 Preparation of Fc Fusion Protein of PDL1 Single Domain Antibody The amino acid sequence of human IgG1-Fc region (SEQ ID NO: 38) was obtained based on the constant region amino acid sequence of human immunoglobulin gamma1 (IgG1) from the protein database Uniprot (P01857). The nucleic acid fragment encoding human IgG1-Fc was obtained from human PBMC total RNA by reverse transcription PCR, and the nucleic acid fragment encoding the fusion protein of PDL1 single domain antibody obtained in the above Example and Fc was obtained by overlapping PCR, then subcloned into vector pCDNA4 (Invitrogen, Cat V86220). Fc region sequences, such as SEQ ID NO: 70 or 71, in which ADCC activity or CDC activity was removed by Site-directed mutagenesis, may also be used.

Recombinant single domain antibody-Fc fusion protein plasmid was transfected into HEK293 cells for antibody expression. The recombinant expression plasmids were diluted with Freestyle 293 medium and added into PEI (polyethylenimine) solution for transformation. Each plasmid/PEI mixture was added to HEK293 cell suspension and incubated at 37° C. and 10% CO$_2$ at 90 rpm. At the same time, 50 μg/L IGF-1 was added. Four hours later EX293 medium, 2 mM glutamine and 50 μg/L IGF-1 were supplemented, cultured at 135 rpm. After 24 hours, 3.8 mM VPA was added. After cultured for 5 to 6 days, the transient expression supernatant was collected and purified by Protein A affinity chromatography to obtain the target PDL1 single domain antibody-Fc fusion protein.

The sequences of the PDL1 single domain antibody-Fc fusion proteins as obtained are shown in SEQ ID NO: 39-SEQ ID NO: 51 and SEQ ID NOs: 72-83, respectively.

of the PDL1 single domain antibody of the present invention was higher than 200 mg/L, while the expression level of the antibody 2.41H90P was about 80 mg/L and the expression level of the antibody 243.55 was about 40 mg/L. This result indicates that the PDL1 single-domain antibody Fc fusion protein of the present invention is more stable in structure and can result in higher expression level than the other two known PDL1 antibodies.

Example 5 Characterization of PDL1 Single Domain Antibody Fc Fusion Protein 5.1 Binding Ability of PDL1 Single Domain Antibody Fc Fusion Protein to PDL1 (by ELISA)

The PDL1-Chis protein (SEQ ID NO: 55) was obtained by transient expression in HEK293 and purification with nickel column affinity chromatography. Plates were coated with the resulting PDL1-Chis protein at 0.5 μg/well overnight at 4° C. Then gradient dilution series of PDL1 single-domain antibody Fc fusion proteins obtained in the above Example were added and allowed to react for 1 hour at room temperature. After washing, goat anti-human IgG-Fc horseradish peroxidase labeled antibody was added and allowed to react for 1 hour at room temperature. After washing, chromogenic agent was added and the absorbance was read at 405 nm. SotfMax Pro v5.4 was used for data processing and mapping analysis, through the four-parameter fitting, to obtain binding curve and EC50 value of the antibody to PDL1 (all test antibody EC50 value of about 150 ng/mL) to reflect the affinity to PDL1.

Figure 5:
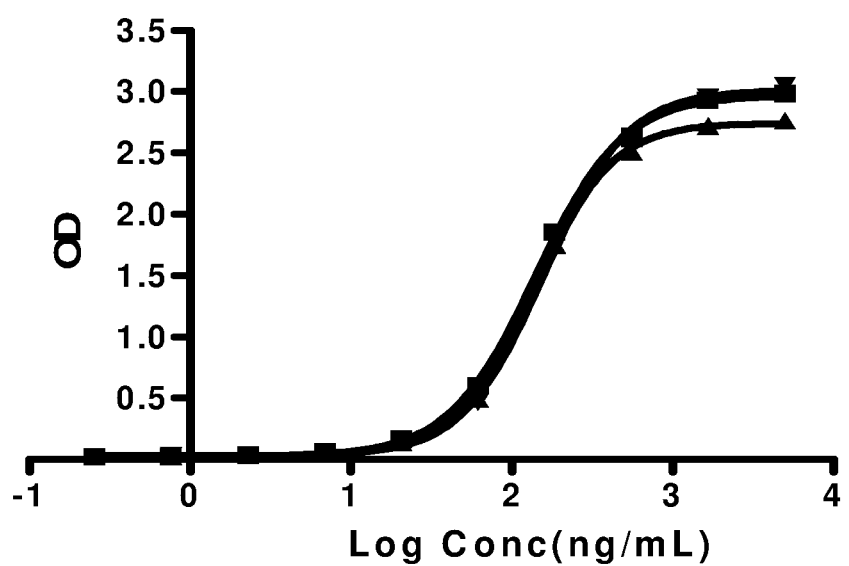
FIG. 5. shows the binding curves of PDL1 single domain antibody-Fc fusion proteins to PDL1 (by ELISA).

The results are shown in FIG. 5, where the longitudinal coordinate is OD405 and the to horizontal ordinate is the concentration of PDL1 single domain antibody Fc-fusion protein (in ng/mL); inverted triangles, triangles, and squares represent the three different humanized forms of Fc fusion proteins: hu56v1-Fc, hu56v2-Fc, hu56v5-Fc. The three proteins have comparable affinity for PDL1.

5.2 Identification of the Binding Ability of PDL1 Single-Domain Antibody Fc Fusion Protein to PDL1 (SPR Method) and Compared with Known Antibodies The binding kinetics of the PDL1 single domain antibody Fc fusion protein to recombinant human PDL1 obtained in the above examples was measured by the surface plasmon resonance (SRP) method using a BIAcore X100 instrument. Recombinant human PDL1-Fc was coated directly onto a CM5 biosensor chip to obtain approximately 1000 response units (RU). For kinetic measurements, the antibodies were serially diluted (1.37 to 1000 nm) in HBS-EP+1× buffer (GE, cat # BR-1006-69) and injected for 120 s at 25° C. with a dissociation time of 30 min, regenerated with 10 mM Glycine-HCl (pH 2.0) for 120 s. Binding rates (kon) and dissociation rates (koff) were calculated using a simple one-to-one Languir binding model (BIAcore Evaluation Software version 3.2). The equilibrium dissociation constant (kD) is calculated as the ratio koff/kon.

The measured binding affinities of anti-PDL1 antibodies are shown in Table 5. The results show that the affinity of PDL1-56-Fc protein to the PDL1 target protein is significantly higher than that of two PDL1 antibodies known in the art, and its higher Ka and lower Kd values indicate that the antibody fusion protein can bind PDL1 antigen more rapidly and thus is difficult to dissociate, which further shows that PDL1-56-Fc as a blocking antibody, with properties better than the two known PDL1 antibody.

TABLE 5

|  | Ka | Kd | KD |
| --- | --- | --- | --- |
| PDL1-56-Fc | 1.796E+6 | 1.432E−5 | 7.975E−12 |
| PDL1-hu56V2-Fc | 2.123E+6 | 1.820E−5 | 8.573E−12 |
| PDL1-56 | 3.323E+6 | 8.213E−4 | 2.472E−10 |
| PDL1-81 | 1.546E+6 | 8.469E−4 | 5.478E−10 |
| PDL1-27 | 1.248E+6 | 9.622E−4 | 7.710E−10 |
| 2.41H90P | 7.949E+5 | 6.160E−5 | 7.750E−11 |
| 243.55 | 4.481E+5 | 6.055E−5 | 1.351E−10 |

5.3 Blocking Effect of PDL1 Single Domain Fc Fusion Protein on PDL1-PD1 Interaction (by Competitive ELISA)

Plates were coated with PDL1-Fc fusion protein 0.5 µg/well overnight at 4° C., followed by addition of gradient dilution series (containing 100 µg/mL PD1-Fc-Biotin) of the PDL1 single-domain antibody Fc fusion protein obtained in the above Example at 100 µL per well, allowed to react for 1 hour at room temperature. After washing, SA-HRP (purchased from Sigma) was added and allowed to react at room temperature for 1 hour. After washing, chromogenic agent was added and the absorbance was read at 405 nm.

Figure 6:
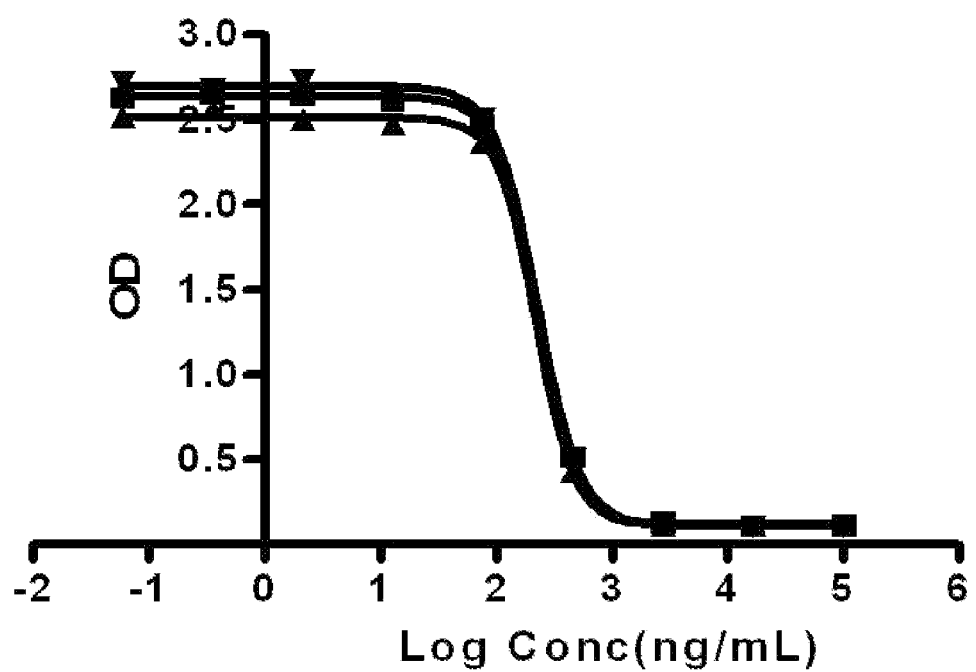
FIG. 6. shows the blocking curves of PDL1 single domain antibody-Fc fusion proteins to PD1/PDL1 interaction (by competitive ELISA).

SotfMax Pro v5.4 was used for data processing and mapping analysis, through the four-parameter fitting, to obtain blocking curve and IC50 value of the antibody to PDL1-PD1. The results are shown in FIG. 6, where longitudinal coordinate is OD405 and the abscissa is the concentration of the PDL1 single domain antibody Fc fusion protein (in ng/mL); the inverted triangle, the trigonometric triangle and the square represent the three different humanized forms of Fc fusion proteins: hu56v1-Fc, hu56v2-Fc, hu56v5-Fc. The three proteins have similar ability to block the PDL1-PD1 interaction.

5.4 Blocking Effect of PDL1 Single Domain Fc Fusion Protein on PDL1-CD80 Interaction (by Competitive ELISA)

The CD80-Fc protein (SEQ ID NO: 56) was obtained from HEK293 cells. Biotinylated protein CD80-Fc-Biotin was obtained using the Thermo Biotinlytion kit.

Plates were coated with PDL1-Fc fusion protein 0.5 µg/well overnight at 4° C., followed by addition of gradient dilution series (containing 300 µg/mL CD80– Fc-Biotin) of the PDL1 single-domain antibody Fc fusion protein obtained in the above Example at 100 µL per well, allowed to react for 1 hour at room temperature. After washing, SA-HRP (purchased from Sigma) was added and allowed to react at room temperature for 1 hour. After washing, chromogenic agent was added and the absorbance was read at 405 nm.

Figure 7:
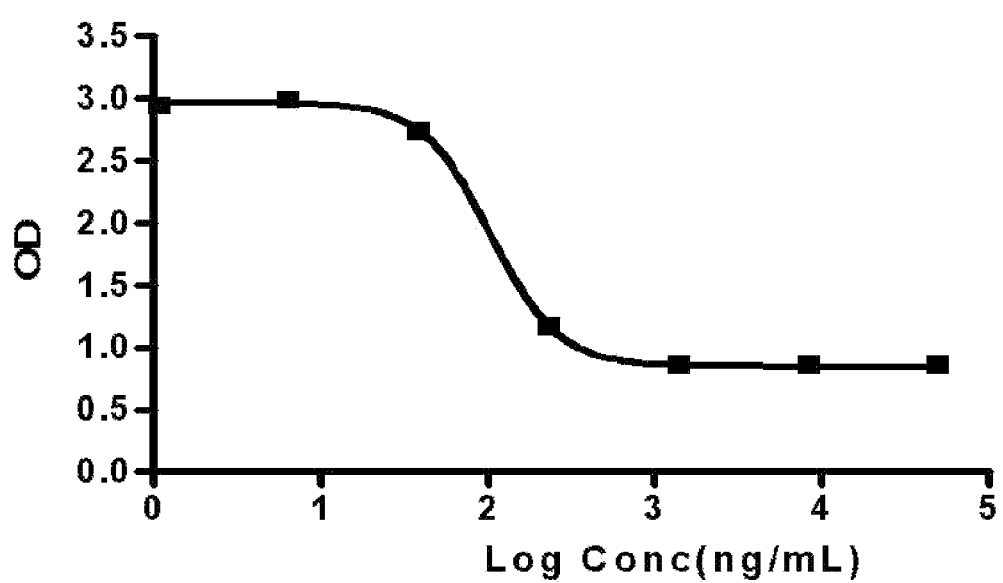
FIG. 7. shows the blocking curves of PDL1 single domain antibody-Fc fusion proteins to CD80/PDL1 interaction (by competitive ELISA).

SotfMax Pro v5.4 was used for data processing and mapping analysis, through the four-parameter fitting, to obtain blocking curve and IC50 value of the antibody to 30 PDL1-CD80. The results are shown in FIG. 7, where the longitudinal coordinate is OD405 and the abscissa is the concentration (in ng/mL) of PDL1 single domain antibody Fc fusion protein hu56V2-Fc. The results show that PDL1 blocking single-domain antibody Fc fusion protein hu56V2-Fc can effectively block the interaction between PDL1 and CD80.

5.5 Blocking Effect of PDL1 Single Domain Fc Fusion Protein on PDL1-PD1 Interaction (by FACS)

Human HEK293 cells transiently express monkey PDL1 protein on membranes by transient transfection of plasmids containing the full length human PDL1 gene.

PD1-muFc (SEQ ID NO: 85) at a working concentration of 2 µg/ml was added to each group according to a 5×10$^5$ cells/tube grouping, and then different concentrations of KN035 were added to each group. After incubating on ice for 30 min and washing for three times, PE-labeled goat-anti-mouse secondary antibody was added as the detection antibody, and the fluorescence intensity was detected by flow cytometry after incubation on ice for 30 minutes.

Figure 8:
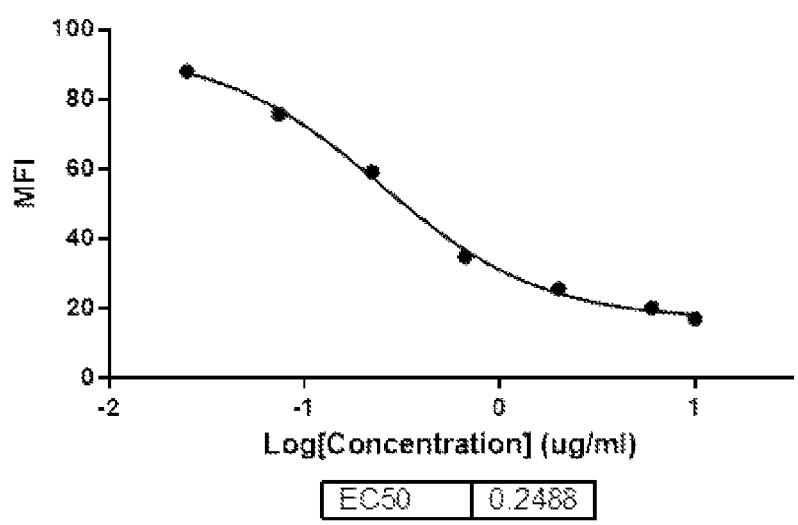
FIG. 8. shows the blocking curves of PDL1 single domain antibody-Fc fusion proteins to PD1/293-PDL1 interaction (by FACS).

GraphPad Prism software was used for data processing and mapping analysis. By four-parameter fitting, the blocking curve and IC50 value of the antibody on the direct interaction between PDL1 expressed on 293 cell membrane and soluble PD1 were obtained. The results are shown in FIG. 8, wherein the longitudinal ordinate is MFI and the abscissa is the concentration (in µg/mL) of the PDL1 single domain antibody fusion protein hu56V1-Fcm1. The results show that PDL1 single-domain antibody Fc fusion protein could effectively block the interaction between PDL1 expressed on 293 cell membrane and PD1.

Plasmid containing human PD1 full-length gene was transformed and integrated into Jurket cell line to obtain Jurket cell line stably expressing human PD1 protein which was named Jurket-PD 1.

After incubation of Jurkat-PD1 cells with biotinylated PDL1-muFc (SEQ ID NO: 84) protein (30 µg/ml) for 30 min on ice, a gradient dilution of PDL1 single domain antibody Fc fusion protein hu56V1-Fcm1 (SEQ ID NO: 79) were added, incubated for 1 h on ice, washed for three times with PBS, and then 1:250 diluted Streptavidin PE was added, incubated on ice for 30 min and washed three times with PBS. Fluorescence intensity was detected by flow cytometry.

Figure 9:
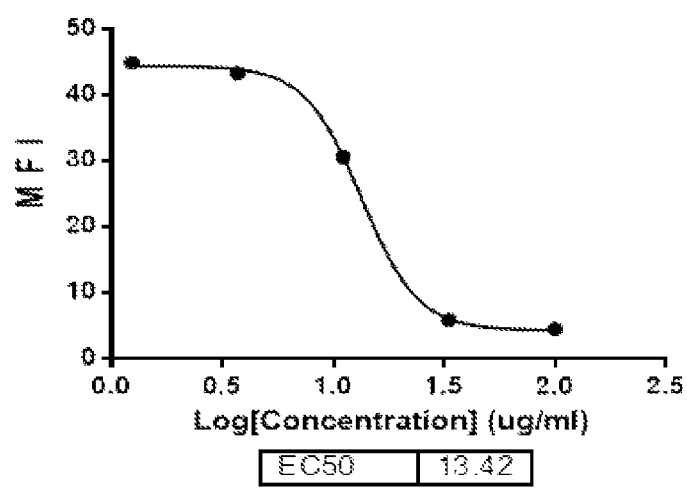
FIG. 9. shows the blocking curves of PDL1 single domain antibody-Fc fusion proteins to Jurket-PD1/PDL1 interaction (by FACS).

Data processing and mapping analysis were performed using GraphPad Prism software. The blocking curves and IC50 values of the antibodies on the direct interaction between Jurkat-PD1 and soluble PDL1-muFc protein were obtained by four-parameter fitting. The results are shown in FIG. 9, where the longitudinal ordinate is MFI and the abscissa is the concentration (in µg/mL) of the PDL1 single domain antibody fusion protein hu56V1-Fcm1. The results show that PDL1 blocking single-domain antibody Fc fusion protein could effectively block the interaction between Jurkat-PD1 and PDL1.

5.6 Binding Specificity of the PDL1 Single Domain Antibody Fc Fusion Protein for PDL1 Protein Human HEK293 cells transiently express human PDL1 protein on membranes by transient transfection of a plasmid carrying the full-length human B7 family protein genes (pCDNA4, Invitrogen, Cat V86220). The plasmid also allows the C-terminus of the target protein to be fused to the EGFP protein so that the level of B7 family protein expressed on the membrane can be examined by green fluorescence intensity. The constructed transient transfected cell lines include 293-PDL1-EGFP, 293-PDL2-EGFP, 293-B7H3-EGFP and 293-B7H3-EGFP.

The constructed cells were resuspended in 0.5% PBS-BSA buffer and hu56V2-Fc antibody was added. At the same time, a negative control of 2 μg of a single domain antibody against other unrelated target was set up and incubated on ice for 20 minutes. After washing, eBioscience secondary antibody anti-hIg-PE was added, on ice for 20 min. After washing, the cells were resuspended in 500 μl of 0.5% PBS-BSA buffer and detected by flow cytometry.

The results are shown in FIG. 8. The upper row shows the control group, the lower row shows the sample groups. It is clear that hu56V2-Fc antibody specifically binds to human PDL1 protein only, not to other B7 family proteins.

5.7 Binding of PDL1 Single Domain Antibody Fc Fusion Protein to Monkey PDL1 Protein Human HEK293 cells transiently express monkey PDL1 protein (SEQ ID NO: 57) by transient transfection of plasmids containing the full length of the monkey PDL1 gene. The plasmid also allows the target protein C-terminal fused to EGFP protein, which allows monkey PDL1 protein membrane expression levels can be investigated by green fluorescence intensity.

The constructed cells were resuspended in 0.5% PBS-BSA buffer, hu56V2-Fc antibody was added and incubated on ice for 20 min. After washing, eBioscience secondary antibody anti-hIg-PE was added, on ice for 20 min. After washing, the cells were resuspended in 500 μl of 0.5% PBS-BSA buffer and detected by flow cytometry.

The results are shown in FIG. 9. It is clear that the hu56V2-Fc antibody binds effectively to the monkey PDL1 protein.

5.8 PDL1 Single-Domain Antibody Fc Fusion Protein can Effectively Identify PDL1 Positive Cell Population on the Patient's Tissue Sections Tumor tissue sections of PDL1-positive lung cancer patients were stained with 5 μg/mL hu56V2-Fc antibody as primary antibody overnight and incubated with goat-anti-human HRP-labeled antibody (Perkin-Elmer, Cat: NEF802001EA), then visualized.

Figure 10:
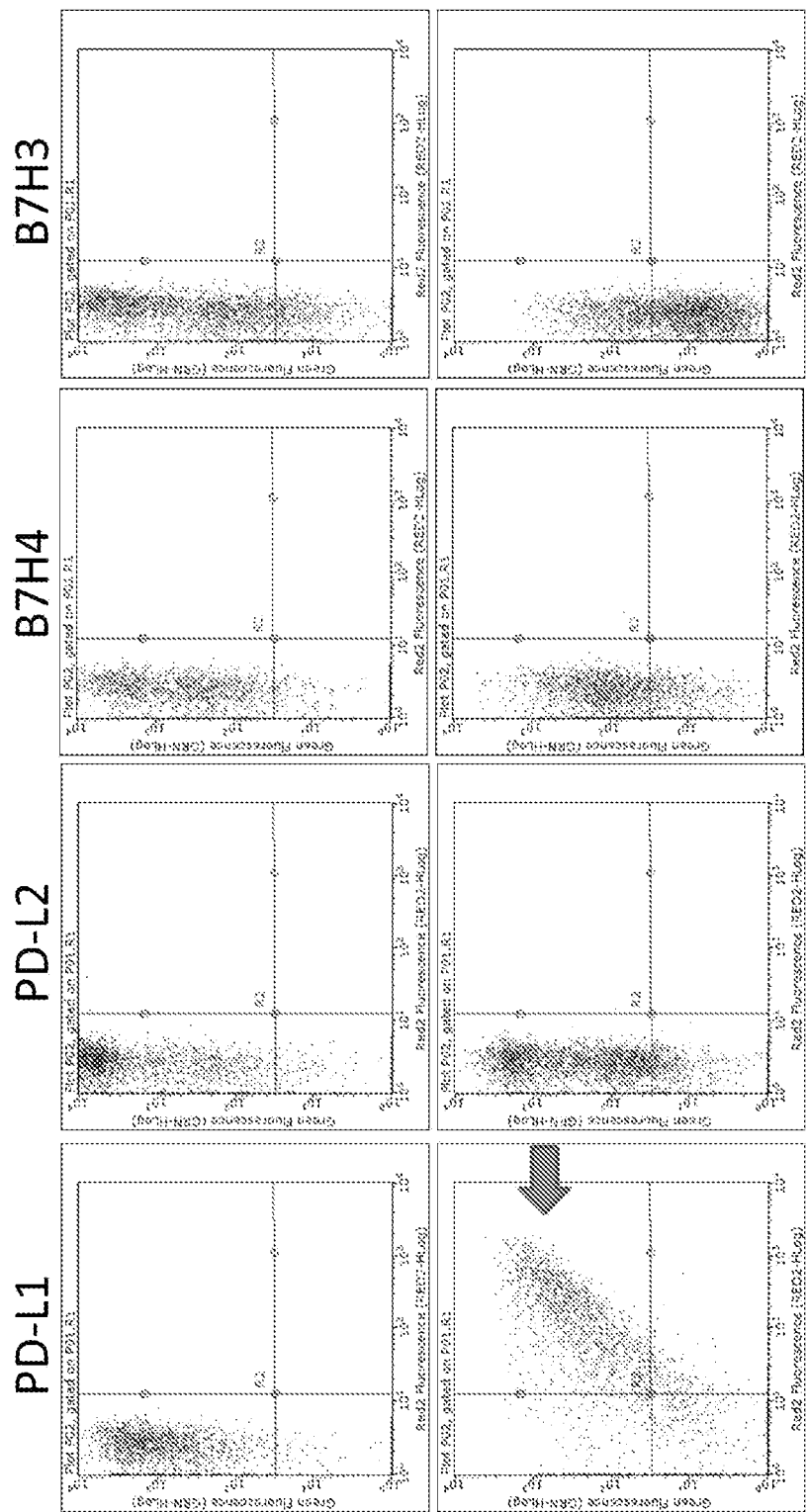
FIG. 10. shows the binding specificity of PDL1 single domain antibody-Fc fusion proteins to PDL1 protein detected by flow cytometry.

The results are shown in FIG. 10. hu56V2-Fc antibody can effectively identify PDL1-positive cell population on lung cancer patient's tissue sections, and can simultaneously identify PDL1-positive tumor cells and PDL1-positive immune cells.

5.9 Activation of PBMC by PDL1 Single Domain Antibody Fc Fusion Protein

Peripheral blood mononuclear cells (PBMCs) were isolated from peripheral blood of healthy donors by density gradient centrifugation using isolation solution for human lymphocytes (Tianjin Hao Yang).

2.5 μg/mL anti-CD3 antibody and gradient dilution series of PDL1 single domain antibody Fc fusion protein hu56V2-Fc (also designated as KN035 in experiment) were coated on cell culture plates overnight at 4° C. The next day, 1×10$^5$ PBMCs were added to each well. After cultured for 5 days, the supernatant was taken and the level of IFN-γ in the supernatant was detected by IFN-γ ELISA kit (ebioscience).

Figure 11:
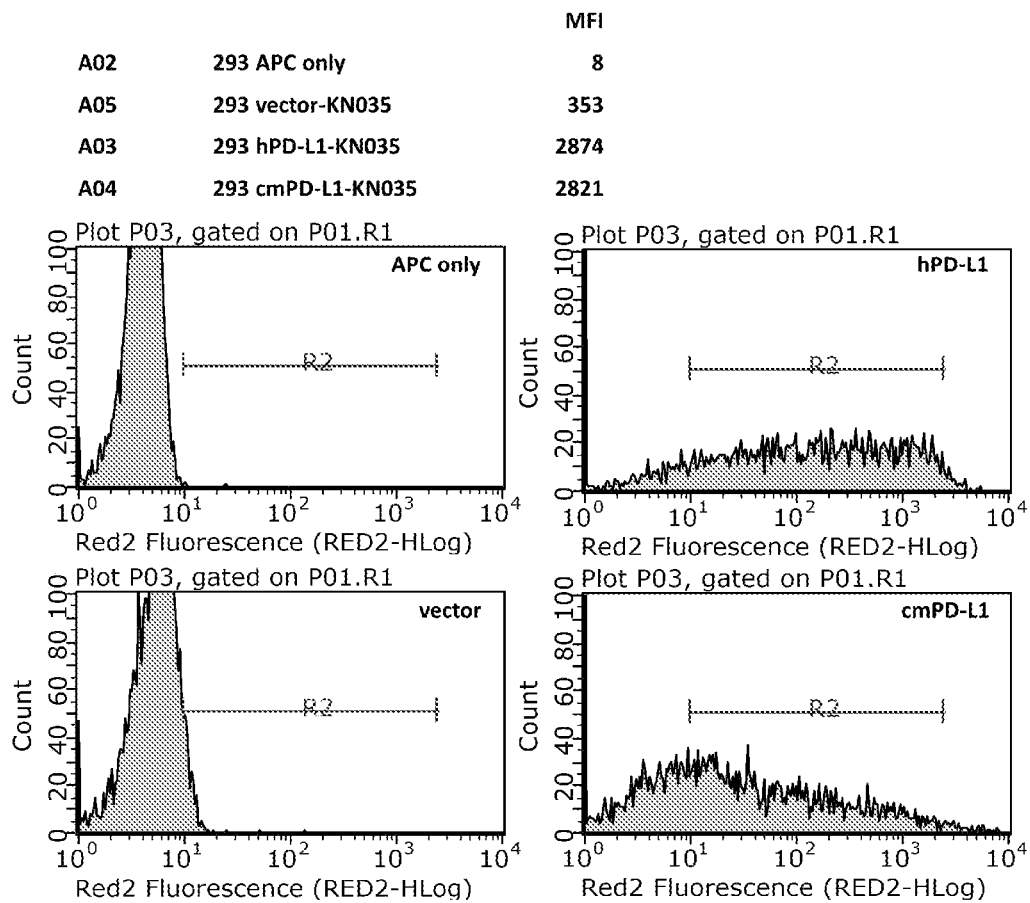
FIG. 11. shows the binding of PDL1 single domain antibody-Fc fusion proteins to monkey PDL1 protein detected by flow cytometry.

The results are shown in FIG. 11. It can be seen that the PDL1 single-domain antibody Fc fusion protein combined with anti-CD3 antibody can enhance the secretion of γ-interferon from PBMC cells, ie, PDL1 single domain Fc fusion protein enhances the activation of PBMC cells. At the same time, the activation effect is concentration-dependent.

5.10 Activation of CD4+T Cells by PDL1 Single-Domain Antibody Fc Fusion Protein in Dendritic Cell-T Cell Mixed Lymphoid Reaction and Comparison with MedImmune LLC Anti-PDL1 Antibody Peripheral blood mononuclear cells (PBMCs) were isolated from white blood cells of peripheral blood from healthy donors by density gradient centrifugation using isolation solution for human lymphocytes (Tianjin Hao Yang). They were then incubated with serum-free RPMI 1640 medium for 1-2 hours to remove non-adherent cells and cells were cultured in RPMI containing 10% FBS, 10 ng/ml GM-CSF and 20 ng/mL IL-4. After culturing for 5-6 days, 10 ng/ml of TNF-α was added and incubated for 24 hours to obtain mature dendritic cells.

Dendritic cells obtained by this method were resuspended in RPMI complete medium, 2×10$^5$/ml. Then 50 ul per well was added to a 96-well U-bottom plate (Costar: 3799) and cultured in an incubator.

CD4+ T cells were isolated from PBMC of another donor using a magnetic bead isolation kit (Miltenyi Biotec: 130-096-533) following the instructions of the manufacturer.

1×10$^4$ dendritic cells and 1×10$^5$ CD4+ T cells obtained by the above methods were mixed, resuspended in RPMI complete medium and added to a 96-well culture plate, and 50 μl of the cell mixture was added to each well. 100 μl per well of hu56V2-Fc diluted in RPMI complete medium was added to a final antibody concentration of 0.1 μg/ml or 0 μg/ml. Supernatants were collected 5-7 days after culture, and IFN-γ level in the supernatant was detected by IFN-γ ELISA kit (ebioscience).

Figure 12:
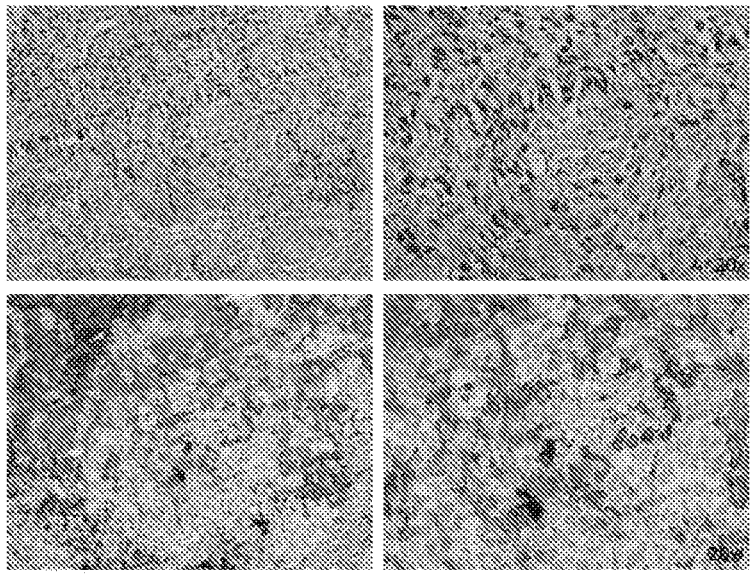
FIG. 12. shows that PDL1 single domain antibody-Fc fusion proteins indentify PDL1 positive cell population on the tissue sections from patients.
Figure 12:
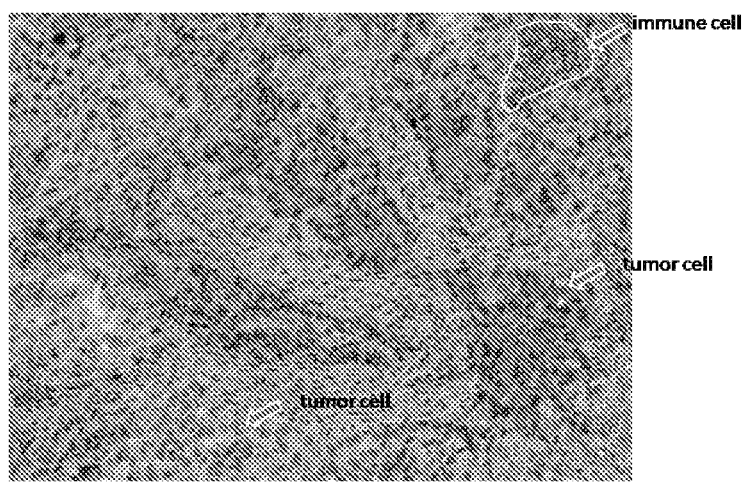

The results are shown in FIG. 12. It can be seen that PDL1 single-domain antibody Fc fusion protein can enhance the IFN-γ secretion of CD4+ T cells in mixed lymphocyte reaction. That is, the PDL1 blocking single-domain antibody Fc fusion protein enhances T cell activation.

PBMCs from Subjects 1 were cultured with 50 ng/ml GM-CSF+25 ng/ml IL-4, and DCs were harvested 6 days after maturation with TNF-α (50 ng/ml); CD4+ T cells were sorted by magnetic bead isolation kit (Miltenyi Biotec: 130-096-533); DC cells were added to 96-well U-bottom plates at 10$^4$/well and 10$^5$/well of CD4+ T cells were added after 2-4 h; different concentrations of PDL1 single domain antibody Fc fusion protein hu56V1-Fcm1 or MedImmune LLC anti-PDL1 antibody 2.41H90P were added to respective wells; after culturing for 5 days, IFN-γ level in the supernatant was detected by IFN-γ ELISA detection kit (ebioscience).

Figure 14:
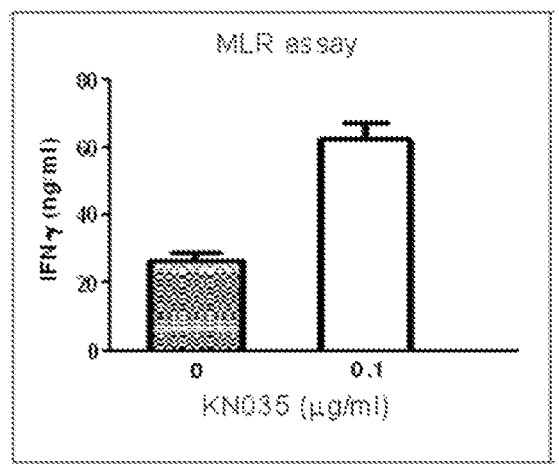
FIG. 14A-B. shows the activation of CD4+T cells by PDL1 single domain antibody-Fc fusion proteins.
Figure 14:
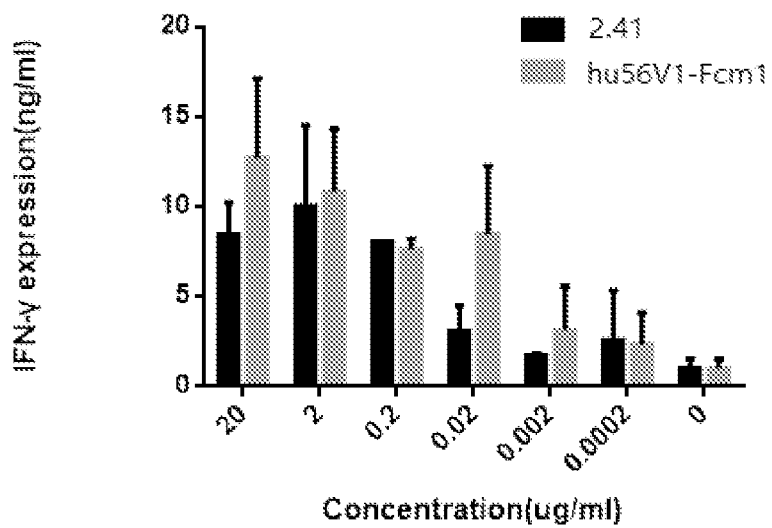

The results are shown in FIG. 14B, in which the gray histogram indicates that the stimulation of IFN-γ secretion by PDL1 single domain antibody Fc fusion protein and the black bar indicates MedImmune LLC anti-PDL1 antibody 2.41H90P. PDL1 single-domain antibody Fc fusion protein with increasing concentrations can enhance the ability of CD4+ T cells to secrete IFN-γ in mixed lymphocyte reaction, and the ability of PDL1 single domain antibody Fc fusion protein to activate T cells is slightly stronger than MedImmune LLC anti-PDL1 antibody 2.41H90P under the same concentration.

5.11 Stimulation of IL-2 Secretion of T Cells in Jurkat/Raji-PDL1 Mixed Culture System by PDL1 Single-Domain Antibody Fc Fusion Protein and Comparison with MedImmune LLC Anti-PDL1 Antibody We constructed a T cell activation system, the Jurkat/Raji-PDL1 co-culture system, to test the effect of PDL1 single domain antibody Fc fusion protein on T cell activation, which was compared with MedImmune LLC anti-PDL1 antibody.

The system uses Jurkat cells (T cells) as effector cells and anti-human CD3 antibody as the first signal for activation of Jurkat cells. B7 family CD80 on the surface of Raji-PDL1 cells which are genetically engineered and stably expressing human PDL1, provides a second co-stimulatory signal to activate Jurket cells, while PDL1 highly expressed on the same cell surface, acts as a negative regulator by binding PD1 to inhibit Jurket cell activation.

Gradient dilutions of hu56V1-Fcm1 and 2.41H90P antibody proteins were prepared using 10% FBS+1640+150 ng/ml anti-CD3; Jurkat and Raji-PDL1 cells were adjusted to $3\times10^6$ cells/ml and $1.5\times10^6$ cells/ml, 50 ul was added to each well, stored at 37° C. for 24 hours. 100 ul of culture supernatant was removed and measured for the expression of IL-2 with kit.

Figure 15:
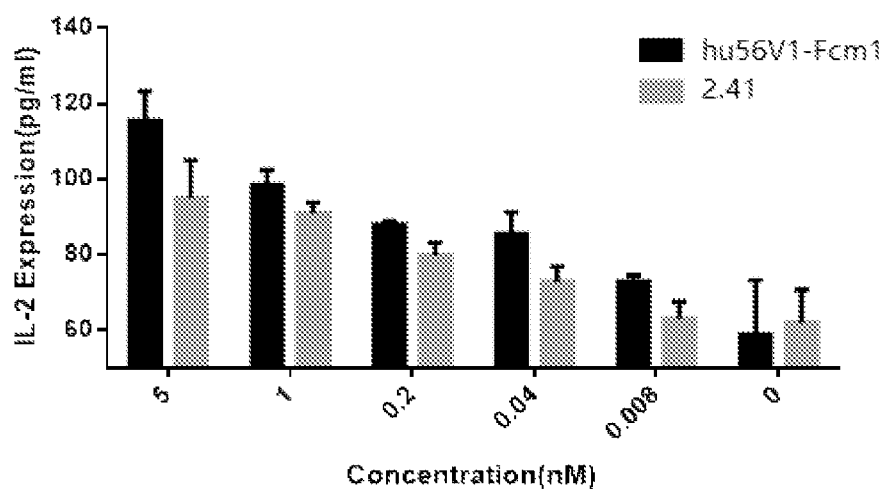
FIG. 15. shows that PDL1 single domain antibody-Fc fusion proteins promote the secretion of IL-2.

FIG. 15 shows the case where the black histogram indicates stimulation of IL-2 secretion by PDL1 single domain antibody Fc fusion protein and the gray histogram indicates MedImmune LLC anti-PDL1 antibody 2.41H90P. PDL1 single-domain antibody Fc fusion protein can enhance the ability of Jurkat cells to secrete IL-2 with increasing concentration, and its ability to activate Jurkat cells is slightly stronger than that of MedImmune LLC PDL1 antibody 2.41H90P at the same concentration.

5.12 Affinity of PDL1 Single-Domain Antibody Fc Fusion Protein to FcRn

Biotinylated PDL1 single domain antibody Fc fusion proteins hu56V1-Fc, hu56V2-Fc, hu56V1-Fcm1 and hu56V2-Fcm1 were diluted to 10 µg/ml and immobilized onto SA biosensors. Human FcRn protein (RnD Systems Cat. No. 8639-FC) was diluted 200 nM, 100 nM, 50 nM, 25 nM, 12.5 nM. Interaction was detected using Octet K2 from Fortebio Corporation, with solidifying for 100 s curing binding for 60 s, dissociation for 30 s.

Table 6 shows that the average KD of PDL1 single-domain antibody Fc fusion proteins to FcRn is about 5.1E-07M. There was no significant difference in affinity between mutant Fc (Fcm1) and wild-type Fc.

TABLE 6

| | KD (M) | kon(1/Ms) | kdis(1/s) |
|---|---|---|---|
| hu56V1-Fc | 5.13E-07 | 1.95E+05 | 1.00E-01 |
| hu56V2-Fc | 5.05E-07 | 2.10E+05 | 1.06E-01 |
| hu56V1-Fcm1 | 5.10E-07 | 1.89E+05 | 9.63E-02 |
| hu56V2-Fcm1 | 5.10E-07 | 2.34E+05 | 1.19E-01 |

5.13 CDC and ADCC Activity of PDL1 Single Domain Antibody Fc Fusion Protein with Mutant Fc PBMCs were activated with 300 IU/ml IL-2 for 24 hours as effector cells, with cell number of $8\times10^5$ cells/well; Raji-PDL1 stably expressing human PDL1 protein was used as target cells with a cell number of $2\times10^5$ cells/well; various concentration of hu56V1-Fcm1 or Rituxan protein as positive control were added, and ADCC activity (%) under each concentration was measured using a CYTOTOX 96® non-radioactive cytotoxicity detection kit after incubation at 37° C. for 6 hours.

Figure 16:
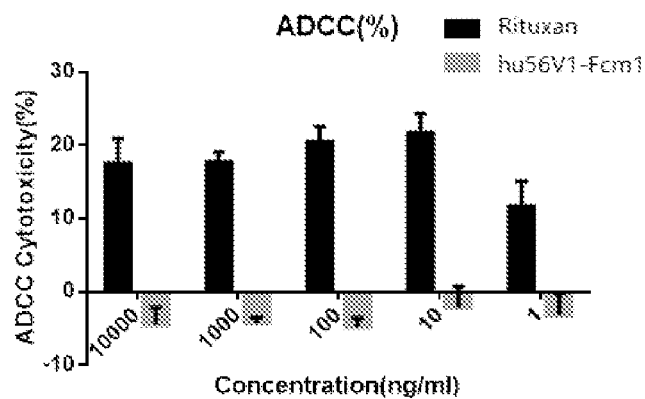
FIG. 16A-B. shows the CDC and ADCC activities of the PDL1 single domain antibody-Fc fusion proteins carrying mutated Fc.
Figure 16:
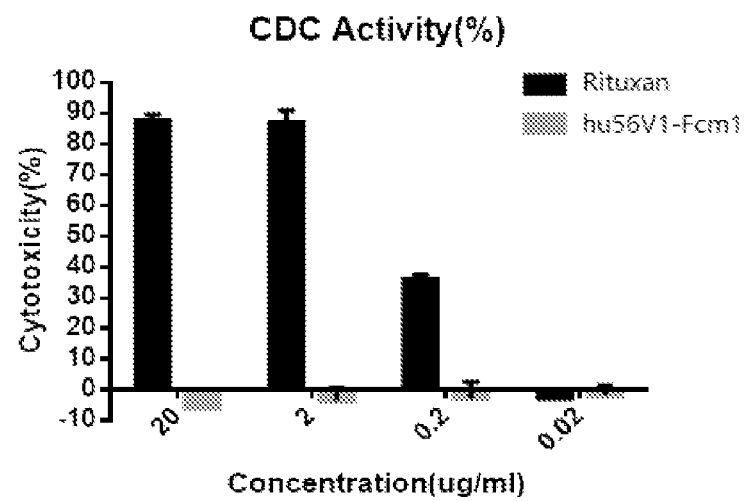

FIG. 16A shows that hu56V1-Fcm1 showed no significant ADCC activity as compared to the positive control Rituxan.

Raji-PDL1 cells are used as target cells with a cell number of $2\times10^4$ cells/well and 5% of cynomolgus serum for providing complements, different concentrations of hu56V1-Fcm1 and positive control Rituxan were added, cultured at 37° C. for 2 h. CDC activity of the sample was detected using CCK-8.

FIG. 16B shows that hu56V1-Fcm1 has no CDC activity at concentrations ranging from 0.02 µg/ml to 20 µg/ml compared to the positive control.

Figure 13:
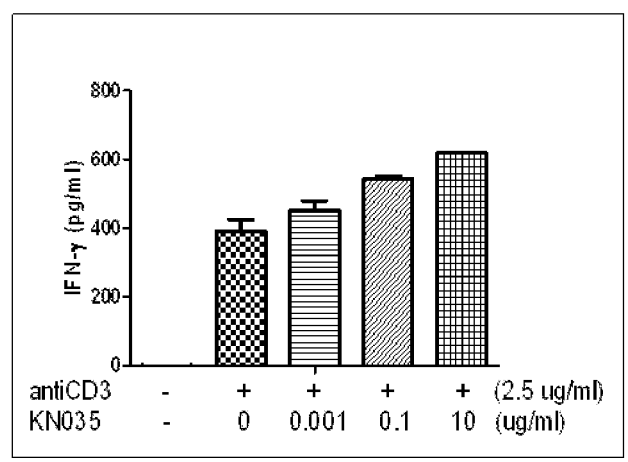
FIG. 13. shows the activation of PBMC by PDL1 single domain antibody-Fc fusion proteins.

5.14 Inhibitory Activity of PDL1 Single Domain Antibody Fc Fusion Protein on Tumor Growth Immunodeficient NOD/SCID (non-obese diabetic/severe combined immunodeficiency) mice were used for studying in vivo activity of the PDL1 single domain antibody Fc fusion protein, hu56V2-Fc that cannot recognize mouse PDL1. The purpose of this study was achieved by experiments in which NOD/SCID mice were subcutaneously transplanted with human PDL1-expressing melanoma cell line A375 (ATCC, CRL-1619™) and human peripheral blood mononuclear cells (PBMCs). A375 and PBMC were mixed in a 5:1 ratio prior to injection and subcutaneously injected in a total volume of 100 µl (containing 5 million A375 and 1 million PBMCs). Antibodies were administered intraperitoneally 24 hours after tumor inoculation and then once a week at a dose of 0.3 mg/kg; PBS served as a negative control. 4-6 mice per experimental group. Tumor formation was observed twice weekly and the long and short diameters of the tumors were measured with a vernier caliper. The tumor volume was calculated and the tumor growth curve was plotted (see FIG. 13). It can be seen that antibody hu56V2-Fc at 0.3 mg/kg dose significantly inhibited tumor growth.

Figure 17:
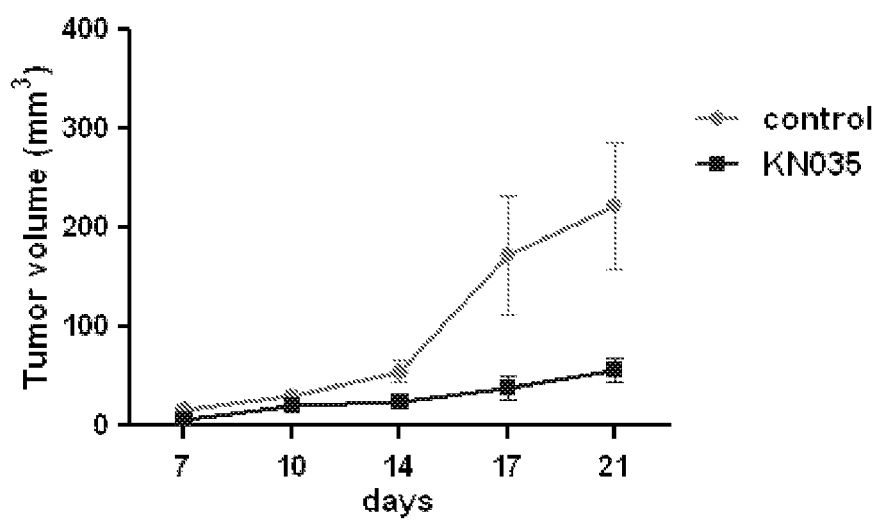
FIG. 17A-B. shows the tumor growth curves after treatment with PDL1 single domain antibody-Fc fusion proteins.
Figure 17:
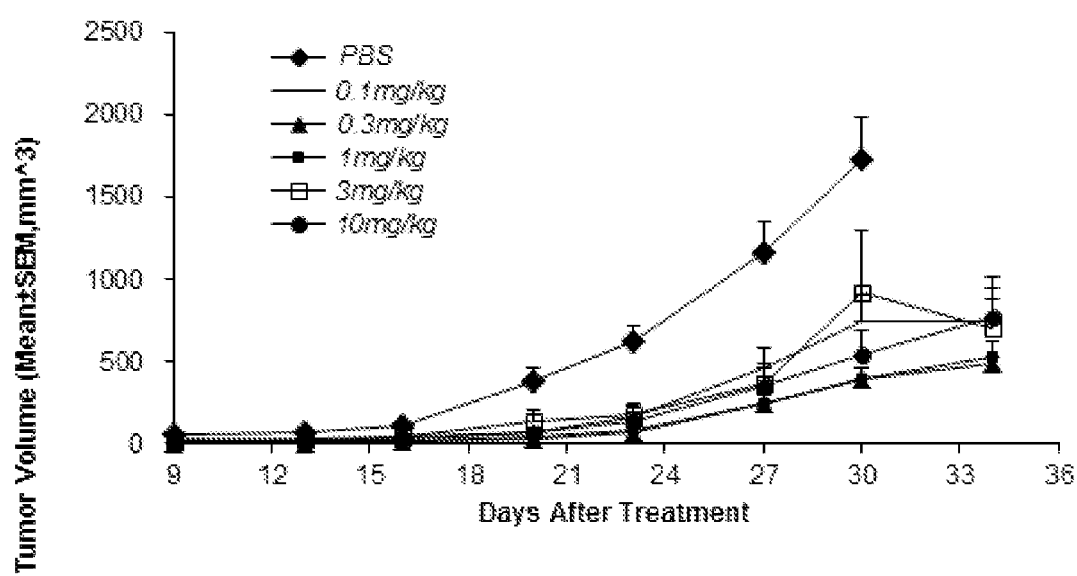

The same in vivo model was used to examine the PDL1 single domain antibody Fc fusion protein, hu56V1-Fcm1, that did not recognize mouse PDL1 either. A375 and human PBMCs were inoculated into NOD-SCID mice subcutaneously at a ratio of 4:1. Four hours later, different doses of hu56V1-Fcm1 (0.1, 0.3, 1, 3 and 10 mg/kg) were administered intraperitoneally. Anti-tumor effect to A375/human PBMCs xenografts in NOD-SCID mice was studied after weekly administration for 4 weeks. PBS was used as a negative control. 4-6 mice per experimental group. Tumor formation was observed twice weekly and the major and minor diameters of the tumors were measured using a vernier caliper. The tumor volume was calculated and the tumor growth curve was plotted (see FIG. 17B). The results show that all doses of hu56V1-Fcm1 (0.1-10 mg/kg) had significant anti-tumor effect on A375/human PBMCs allogeneic xenografts of NOD-SCID mice, but without significant dose-relevance. Antibody hu56V1-Fcm1 significantly inhibited tumor growth even at a dose of 0.1 mg/kg.

Figure 18:
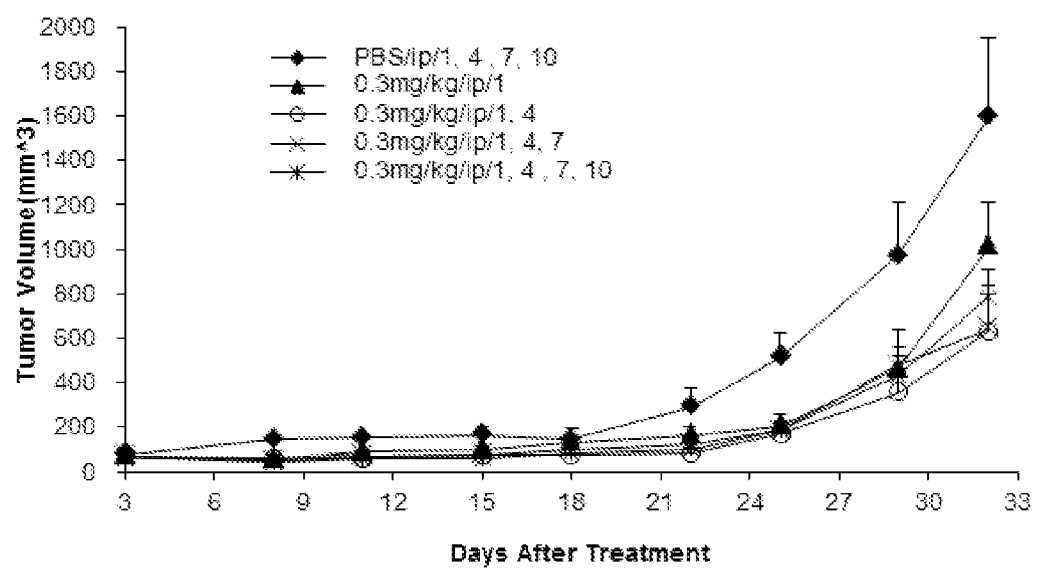
FIG. 18. shows the inhibition of tumor growth by administering PDL1 single domain antibody-Fc fusion proteins for various times.
Figure 19A:
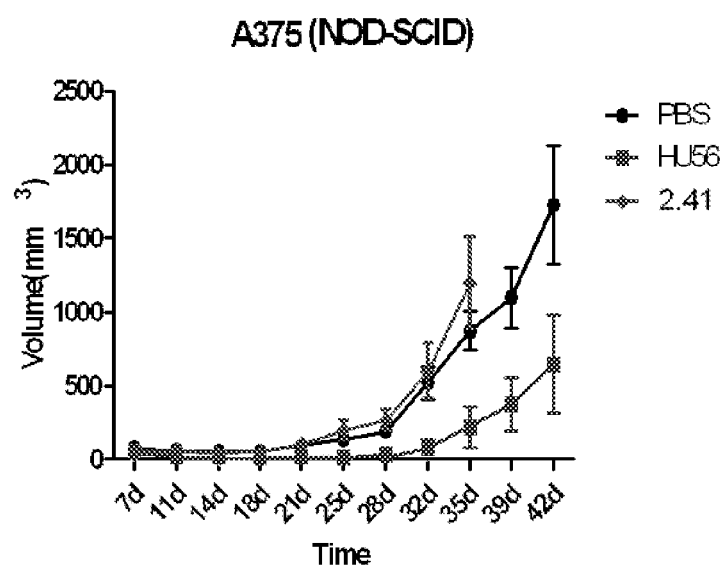
FIG. 19A-B. shows the comparison between the tumor growth inhibitory activities of hu56V2-Fc and 2.41. A, A375:PBMC=5:1; B, A375:PBMC=1:1.
Figure 19B:
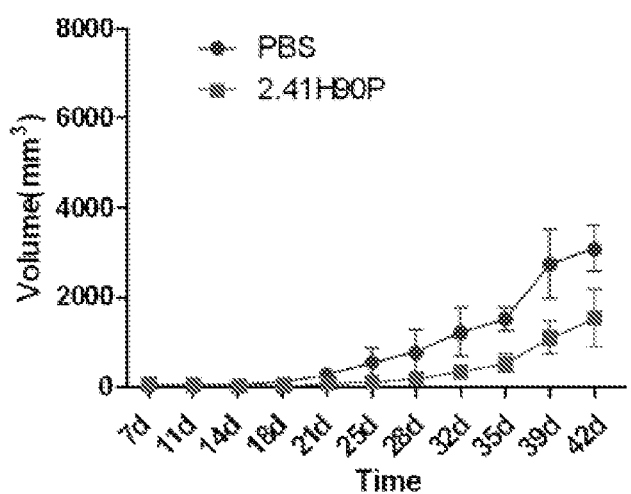
Figure 20:
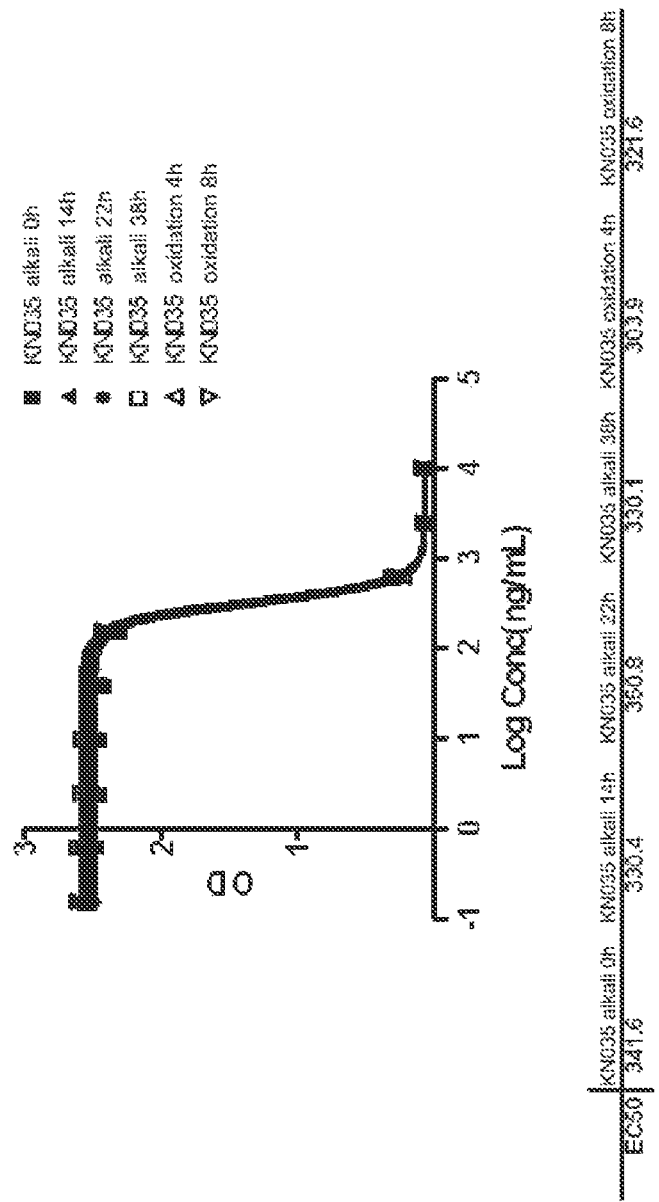
FIG. 20. shows the influence of alkali and oxidation treatments to the activity of PDL1 single domain antibody-Fc fusion proteins.

5.15 Inhibitory Activity on Tumor Growth of PDL1 Single-Domain Antibody Fc Fusion Protein Administered for Different Times NOD-SCID mouse A375/human PBMCs xenograft tumor model was used. A375 with human PBMCs at a ratio of 4:1 was subcutaneously inoculated to NOD-SCID mice and hu56V1-Fcm1 (0.3 mg/kg) was injected intraperitoneally 4 hours later followed by intraperitoneal administration once every three days. The final numbers of administration were 1, 2, 3, 4 times. Tumor formation was observed every three days and the major and minor diameters of the tumors were measured with a vernier caliper to calculate the tumor volume until the 33rd day from the first administration. The tumor growth curve was plotted (FIG. 18). The results showed that different number of administration in the study period all had significant antitumor effects on A375/human PBMCs allogeneic xenografts of NOD-SCID mice.

5.16 Inhibition of Tumor Growth by PDL1 Single Domain Antibody Fc Fusion Protein and Comparison with MedImmune LLC Anti-PDL1 Antibody The purpose of this study was achieved by experiments in which NOD/SCID mice were subcutaneously transplanted with human PDL1-expressing melanoma cell line A375 (ATCC, CRL-1619™) and human peripheral blood mononuclear cells (PBMCs). A375 and PBMC were mixed in a 5:1 ratio prior to injection in a total volume of 100 µl (containing 5 million A375 and 1 million PBMCs). The antibodies were administered intraperitoneally for 24 hours after tumor inoculation and then weekly once, at a dose of 1 mg/kg. The treatment group included hu56V2-Fc (denoted hu56) and MedImmune LLC's anti-PDL1 antibody group (indicated as 2.41) with PBS as a negative control. 4-6 mice per experimental group. Tumor formation was observed twice a week, and the major and minor diameters of the tumors were measured with a vernier caliper. The tumor volume was calculated and the tumor growth curve was plotted (see FIG. 14 A). MedImmune LLC's anti-PDL1 antibody was essentially ineffective in this model and the tumor volume exceeded the negative control group on day 35, thus the administration and tumor volume measurement were stopped. It can be seen that the effect of hu56V2-Fc in inhibiting A375 tumor growth at 1 mg/kg dose is significantly superior to MedImmune LLC's anti-PDL1 antibody 2.41H90P under this model.

Since anti-PDL1 antibodies from MedImmune LLC did not show tumor suppression under the above system, it is possible that the activation of PBMC in the system is insufficient to inhibit tumor cell growth. Thus the content of PBMC in mixed cells was increased for examining again the anti-tumor effect of MedImmune LLC anti-PDL1 antibody.

The A375 and PBMC were mixed 1:1 prior to injection in a total volume of 100 µl (containing 5 million A375 and 5 million PBMCs) subcutaneously and MedImmune LLC anti-PDL1 antibody (2.41H90P) was administered intraperitoneally followed by weekly administration at a dose of 1 mg/kg; PBS was used as a negative control. 4-6 mice per experimental group. Tumor formation was observed twice weekly and the major and minor diameters of the tumors were measured using a vernier caliper. The tumor volume was calculated and the tumor growth curve was plotted (see FIG. 14B). It can be seen that anti-PDL1 antibody from MedImmune LLC shows anti-tumor effect in in vivo model after increasing the proportion of PMBC.

The mean tumor inhibition (TGI=(1−tumor volume of treatment group/tumor volume of control group)×100%) on day 42 of the antibody is calculated and presented in Table 6 below:

TABLE 6

| | TGI | |
|---|---|---|
| | hu56V2-Fc | 2.41H90P |
| 5:1 | 65.7% | N.A. |
| 5:5 | — | 41.7% |

The above in vivo antitumor experiment results show that the PDL1 blocking single-domain antibody Fc fusion proteins of the present invention have significantly superiority to the known PDL1 blocking antibodies (Anti-PDL1 antibody from MedImmune LLC) in an in vivo melanoma A375 nude mouse model.

Example 6 Stability of PDL1 Single Domain Antibody Fc Fusion Protein 6.1 Resistance of PDL1 Single Domain Antibody Fc Fusion Protein to Alkali and Oxidative Stress 500 mM ammonium bicarbonate was used as alkali disrupting agent and fusion proteins were treated at 37° C. for 38 hours. 1% hydrogen peroxide was used as the oxidant, 8 hours treatment at room temperature The changes in the biological activity of the PDL1 single-domain antibody Fc fusion protein obtained by the above Examples before and after treatment were measured using competitive ELISA. As can be seen in FIG. 15, alkali and oxidative treatments did not affect the activity of the candidate PDL1 single domain antibody Fc fusion protein, and the competitive ELISA activity after 38 hours of alkali treatment was 103% relative to 0 hour.

The competitive ELISA activity at 8 hours of oxidation treatment was 106% relative to 0 hour.

6.2 Stability of PDL1 Single Domain Antibody Fc Fusion Protein at High Concentration The PDL1 single domain antibody Fc fusion protein was concentrated by UF/DF and exchanged into PBS buffer. And the aggregate formation tendency thereof was examined by SE-HPLC.

When concentrated to 200 mg/mL, the purity of the PDL1 single domain Fc fusion protein was 96.8% by SE-HPLC detection. Aggregates was increased by about 2.4% over that at low concentrations (~2 mg/mL). Throughout the concentration process, no turbid phenomenon or aggregation occurred in the protein solution.

```
Sequence Listing

>SEQ ID NO: 1 antibody No. 10 CDR1
SYCMG

>SEQ ID NO: 2 antibody No. 10 CDR2
AIDSDGTTKYADSMKG

>SEQ ID NO: 3 antibody No. 10 CDR3
RLNCPGPVDWVPMFPY

>SEQ ID NO: 4 antibody No. 27 CDR1
RRCMA
```

Sequence Listing

>SEQ ID NO: 5 antibody No. 27 CDR2
NILTTTGNTYLADSVKG

>SEQ ID NO: 6 antibody No. 27 CDR3
DSFHDPTCTVVASSGAFQY

>SEQ ID NO: 7 antibody No. 38 CDR1
RRCMG

>SEQ ID NO: 8 antibody No. 38 CDR2
NITGTGNTYLADSVKG

>SEQ ID NO: 9 antibody No. 38 CDR3
DSFPTCTVVASSGAFQY

>SEQ ID NO: 10 antibody No. 56 CDR1
RRCMA

>SEQ ID NO: 11 antibody No. 56 CDR2
KLLTTSGSTYLADSVKG

>SEQ ID NO: 12 antibody No. 56 CDR3
DSFEDPTCTLVTSSGAFQY

>SEQ ID NO: 13 antibody No. 69 CDR1
SYCMA

>SEQ ID NO: 14 antibody No. 69 CDR2
KILTTPGNTYLADSVKG

>SEQ ID NO: 15 antibody No. 69 CDR3
DSFQKPTCTVVASWPAFQY

>SEQ ID NO: 16 antibody No. 81 CDR1
VRCMA

>SEQ ID NO: 17 antibody No. 81 CDR2
NILTTTISTYLADSVKG

>SEQ ID NO: 18 antibody No. 81 CDR3
DSFGYPTCPGPASSGAFQY

>SEQ ID NO: 19 antibody No. 87 CDR1
SCGMG

>SEQ ID NO: 20 antibody No. 87 CDR2
TISSDGITSYADSVKG

>SEQ ID NO: 21 antibody No. 87 CDR3
DCPPIPEFTSCSGGYCLSGDY

>SEQ ID NO: 22 antibody No. 94 CDR1
SYCMG

>SEQ ID NO: 23 antibody No. 94 CDR2
TIDSDGTTRYVDSVKG

>SEQ ID NO: 24 antibody No. 94 CDR3
RLNCPGPVDWVPMFPY

>SEQ ID NO: 25 antibody No. 10
QVQLQESGGGSVQAGGSLRLSCAASGNIVSSYCMGWFRQAPGKERVGVAAID
SDGTTKYADSMKGRFTISKDNAKNTLDLQMNSLKPEDTAMYYCVARLNCPGP
VDWVPMFPYRGQGTWTVSS >SEQ ID NO: 26 antibody No. 27
QVQLQESGGGSVQAGGSLRLSCAASGNISSRRCMAWFRQAPGKERERVANIL
TTTGNTYLADSVKGRFTISQNNAKSTVYLQMNSLKPEDTAMYYCAADSFHDP
TCTVVASSGAFQYWGQGTQVTVSS >SEQ ID NO: 27 antibody No. 38
QVQLQESGGGSVQAGGSLRLSCAVEGFISSRRCMGWFRQAPGKERVGVANIT
GTGNTYLADSVKGRFTISQNNAKSTVYLQMNSLKPEDTAMYYCAADSFPTCT
VVASSGAFQYWGQGTQVTVSS

```
>SEQ ID NO: 28 antibody No. 56
QVQLQESGGGLVQPGGSLRLSCAASGKMSSRRCMAWFRQAPGKERERVAKLLT
TSGSTYLADSVKGRFTISQNNAKSTVYLQMNSLKPEDTAMYYCAADSFEDPT
CTLVTSSGAFQYWGQGTQVTVSS >SEQ ID NO: 29 antibody No. 69
QVQLQESGGGSVQAGGSLRLSCAVQRNISSSYCMAWFRQAPGKQRERVDKIL
TTPGNTYLADSVKGRFTISQNNAKSTVYLQMNSLKPEDTAMYYCAADSFQKP
TCTVVASWPAFQYWGQGTQVTVSS >SEQ ID NO: 30 antibody No. 81
QVQLQESGGSVQAGGSLRLSCAASGNIIRVRCMAWFRQAPGKEPERGPNILT
TTISTYLADSVKGRFTISQNNAKSTVYLQMNSLKPEDTAMYYCAADSFGYPT
CPGPASSGAFQYWGQGTWTVSS >SEQ ID NO: 31 antibody No. 87
QVQLQESGGGSVQAGGSLKLSCAASGYIFSSCGMGWYRQAPGKERELVSTIS
SDGTTSYADSVKGRFTISDNAKNTLYLQMNSLKTEDTAVYYCVADCPPIPEF
TSCSGGYCLSGDYWGQGTQVTVSS >SEQ ID NO: 32 antibody No. 94
QVQLQESGGGSVQAGGSLRLSCAASLNIFSSYCMGWFRQAPGKQRVGVATID
SDGTTRYVDSVKGRFTISKDNAKNTLDLQMNSLKPEDTAMYYCAARLNCPGP
VDWVPMFPYRGQGTQVTVSS >SEQ ID NO: 33 Hu56V1
QVQLVESGGGLVQPGGSLRLSCAASGKMSSRRCMAWFRQAPGKERERVAKLL
TTSGSTYLADSVKGRFTISRDNSKNTVYLQMNSLRAEDTAVYYCAADSFEDP
TCTLVTSSGAFQYWGQGTLVTVSS >SEQ ID NO: 34 Hu56V2
QVQLVESGGGLVQPGGSLRLSCAASGFTFSRRCMAWFRQAPGKERERVAKLL
TTSGSTYLADSVKGRFTISRDNSKNTVYLQMNSLRAEDTAVYYCAADSFEDP
TCTLVTSSGAFQYWGQGTLVTVSS >SEQ ID NO: 35 Hu56V3
QVQLVESGGGLVQPGGSLRLSCAASGKMSSRRCMAWFRQAPGKGLERVAKLL
TTSGSTYLADSVKGRFTISRDNSKNTVYLQMNSLRAEDTAVYYCAADSFEDP
TCTLVTSSGAFQYWGQGLVTVSS >SEQ ID NO: 36 Hu56V4
QVQLVESGGGLVQPGGSLRLSCAASFTFSRRCMAWFRQAPGKGLERVAKLLT
TSGSTYLADSVKGRFTISRDNSKNTVYLQMNSLRAEDTAVYYCAADSFEDPT
CTLVTSSGAFQYWGQGTLVTVSS >SEQ ID NO: 37 Hu56V5
QVQLVESGGGLVQPGGSLRLSCAASGKMSSRRCMAWFRQAPGKERERVAKLL
TTSGSTYLADSVKGRFTISRDNSKNTVYLQMNSLKAEDTAVYYCAADSFEDP
TCTLVTSSGAFQYWGQGTLVTVSS >SEQ ID NO: 38 Human IgG1 Fc
EPKSCDKTHTCPPCPAPELLGGPSVFLFPPKPKDTLMISRTPEVTCVVVDVS
HEDPEVKFNWYVDGVEVHNAKTKPREEQYNSTYRVVSVLTVLHQDWLNGKEY
KCKVSNKALPAPIEKTISKAKGQPREPQVYTLPPSRDELTKNQVSLTCLVKG
FYPSDIAVEWESNGQPENNYKTTPPVLDSDGSFFLYSKLTVDKSRWQQGNVF
SCSVMHEALHNHYTQKSLSLSPGK >SEQ ID NO: 39 10-Fc
QVQLQESGGGSVQAGGSLRLSCAASGNIVSSYCMGWFRQAPGKERVGVAAID
SDGTTKYADSMKGRFTISKDNAKNTLDLQMNSLKPEDTAMYYCVARLNCPGP
VDWVPMFPYPGQGTQVTVSSEPKSCDKTHTCPPCPAPELLGGPSVFLFPPKP
KDTLMISRTPEVTCVVVDVSHEDPEVKFNWYVDGVEVHNAKTKPREEQYNST
YRVVSVLTVLHQDWLNGKEYKCKVSNKALPAPIEKTISKAKGQPREPQVYTL
PPSRDELTKNQVSLTCLVKGFYPSDIAVEWESNGQPENNYKTTPPVLDSDGS
FFLYSKLTVDKSRWQQGNVFSCSVMHEALHNHYTQKSLSLSPGK >SEQ ID NO: 40 27-Fc
QVQLQESGGGSVQAGGSLRLSCAASGNISSRRCMAWFRQAPGKERERVANIL
TTTGNTYLADSVKGRFTISQNNAKSTVYLQMNSLKPEDTAMYYCAADSFHDP
TCTVVASSGAFQYWGQGTQVTVSSEPKSCDKTHTCPPCPAPELLGGPSVFLF
PPKPKDTLMISRTPEVTCVVVDVSHEDPEVKFNWYVDGVEVHNAKTKPREEQ
YNSTYRVVSVLTVLHQDWLNGKEYKCKVSNKALPAPIEKTISKAKGQPREPQ
VYTLPPSRDELTKNQVSLTCLVKGFYPSDIAVEWESNGQPENNYKTTPPVLD
SDGSFFLYSKLTVDKSRWQQGNVFSCSVMHEALHNHYTQKSLSLSPGK
```

Sequence Listing

>SEQ ID NO: 41 38-Fc
QVQLQESGGGSVQAGGSLRLSCAVSGFISSRRCMGWFPQAPGKERVGVANIT
GTGNTYLADSVKGRFTISQNNAKSTVYLQMNSLKPEDTAMYYCAADSFPTCT
VVASSGAFQYWGQGTQVTVSSEPKSCDKTHTCPPCPAPELLGGPSVFLFPPK
PKDTLMISRTPEVTCVVVDVSHEDPEVKFNWYVDGVEVENAKTKPREEQYNS
TYRVVSVLTVLHQDWLNGKEYKCKVSNKALPAPIEKTISKAKGQPREPQVYT
LPPSPDELTKNQVSLTCLVKGFYPSDIAVEWESNGQPENNYKTTPPVLDSDG
SFFLYSKLTVDKSRWQQGNVFSCSVMHEALHNHYTQKSLSLSPGK

>SEQ ID NO: 42 56-Fc
QVQLQESGGGLVQPGGSLRLSCAASGKMSSRRCMAWFRQAPGKERERVAKLL
TTSGSTYLADSVKGRFTISQNNAKSTVYLQMNSLKPEDTAMYYCAADSFEDP
TCTLVTSSGAFQYWGQGTQVTVSSEPKSCDKTHTCPPCPAPELLGGPSVFLF
PPKPKDTLMISRTPEVTCVVVDVSHEDPEVKFNWYVDGVEVHNAKTKPREEQ
YNSTYRVVSVLTVLHQDWLNGKEYKCKVSNKALPAPIEKTISKAKGQPREPQ
VYTLPPSRDELTKNQVSLTCLVKGFYPSDIAVEWESNGQPENNYKTTPPVLD
SDGSFFLYSKLTVDKSRWQQGNVFSCSVMHEALHNHYTQKSLSLSPGK

>SEQ ID NO: 43 69-Fc
QVQLQESGGGSVQAGGSLRLSCAVQRNISSSYCMAWFRQAPGKQRERVDKIL
TTPGNTYLADSVKGRFTISQNNAKSTVYLQMNSLKPEDTAMYYCAADSFQKP
TCTVVASWPAFQYWGQGTQVTVSSEPKSCDKTHTCPPCPAPELLGGPSVFLF
PPKPKDTLMISRTPEVTCVVVDVSHEDPEVKFNWYVDGVEVHNAKTKPREEQ
YNSTYRVVSVLTVLHQDWLNGKEYKCKVSNKALPAPIEKTISKAKGQPREPQ
VYTLPPSRDELTKNQVSLTCLVKGFYPSDIAVEWESNGQPENNYKTTPPVLD
SDGSFFLYSKLTVDKSRWQQGNVFSCSVMHEALHNHYTQKSLSLSPGK

>SEQ ID NO: 44 81-Fc
QVQLQESGGGSVQAGGSLRLSCAASGNIIRVRCMAWFRQAPGKERERGPNIL
TTTISTYLADSVKGRFTISQNNAKSTVYLQMNSLKPEDTAMYYCAADSFGYP
TCPGPASSGAFQYWGQGTQVTVSSEPKSCDKTHTCPPCPAPELLGGPSVFLF
PPKPKDTLMISRTPEVTCVVVDVSHEDPEVKFNWYVDGVEVHNAKTKPREEQ
YNSTYRVVSVLTVLHQDWLNGKEYKCKVSNKALPAPIEKTISKAKGQPREPQ
VYTLPPSRDELTKNQVSLTCLVKGFYPSDIAVEWESNGQPENNYKTTPPVLD
SDGSFFLYSKLTVDKSRWQQGNVFSCSVMHEALHNHYTQKSLSLSPGK

>SEQ ID NO: 45 87-Fc
QVQLQESGGGSVQAGGSLKLSCAASGYIFSSCGMGWYRQAPGKERELVSTIS
SDGTTSYADSVKGRFTISQDNAKNTLYLQMNSLKTEDTAVYYCVADCPPIPE
FTSCSGGYCLSGDYWGQGTQVTVSSEPKSCDKTHTCPPCPAPELLGGPSVFL
FPPKPKDTLMISRTPEVTCVVVDVSHEDPEVKFNWYVDGVEVHNAKTKPREE
QYNSTYRVVSVLTVLHQDWLNGKEYKCKVSNKALPAPIEKTISKAKGQPREP
QVYTLPPSPDELTKNQVSLTCLVKGFYPSDIAVEWESNGQPENNYKTTPPVL
DSDGSFFLYSKLTVDKSRWQQGNVFSCSVMHEALHNHYTQKSLSLSPGK

>SEQ ID NO: 46 94-Fc
QVQLQESGGGSVQAGGSLRLSCAASLNIFSSYCMGWFRQAPGKQRVGVATID
SDGTTRYVDSVKGRFTISKDNAKNTLDLQMNSLKPEDTAMYYCAARLNCPGP
VDWVPMFPYRGQGTQVTVSSEPKSCDKTHTCPPCPAPELLGGPSVFLFTPKP
KDTLMISRTPEVTCVVVDVSHEDPEVKFNWYVDGVEVHNAKTKPREEQYNST
YRVVSVLTVLHQDWLNGKEYKCKVSNKALPAPIEKTISKAKGQPREPQVYTL
PPSRDELTKNQVSLTCLVKGFYPSDIAVEWESNGQPENNYKTTPPVLDSDGS
FFLYSKLTVDKSRWQQGNVFSCSVMHEALHNHYTQKSLSLSPGK

>SEQ ID NO: 47 Hu56V1-Fc
QVQLVESGGGLVQPGGSLRLSCAASGKMSSRRCMAWFRQAPGKERERVAKLL
TTSGSTYLADSVKGRFTISRDNSKNTVYLQMNSLRAEDTAVYYCAADSFEDP
TCTLVTSSGAFQYWGQGTLVTVSSEPKSCDKTHTCPPCPAPELLGGPSVFLF
PPKPKDTLMISRTPEVTCVVVDVSHEDPEVKFNWYVDGVEVHNAKTKPREEQ
YNSTYRVVSVLTVLHQDWLNGKEYKCKVSNKALPAPIEKTISKAKGQPREPQ
VYTLPPSRDELTKNQVSLTCLVKGFYPSDIAVEWESNGQPENNYKTTPPVLD
SDGSFFLYSKLTVDKSRWQQGNVFSCSVMHEALHNHYTQKSLSLSPGK

>SEQ ID NO: 48 Hu56V2-Fc
QVQLVESGGGLVQPGGSLRLSCAASGFTFSRRCKAWFRQAPGKERERVAKIL
TTSGSTYLADSVKGRFTISRDNSKNTVYLQMNSLRAEDTAVYYCAADSFEDP
TCTLVTSSGAFQYWGQGTLVTVSSEPKSCDKTHTCPPCPAPELLGGPSVFLF
PPKPKDTLMISRTPEVTCVVVDVSHEDPEVKFNWYVDGVEVHNAKTKPREEQ
YNSTYRVVSVLTVLHQDWLNGKEYKCKVSNKALPAPIEKTISKAKGQPREPQ
VYTLPPSRDELTKNQVSLTCLVKGFYPSDIAVEWESNGQPENNYKTTPPVLD
SDGSFFLYSKLTVDKSRWQQGNVFSCSVMHEALHNHYTQKSLSLSPGK

>SEQ ID NO: 49 Hu56V3-Fc
QVQLVESGGGLVQPGGSLRLSCAASGKMSSRRCMAWFRQAPGKGLERVAKLL
TTSGSTYLADSVKGRFTISRDNSKNTVYLQMNSLRAEDTAVYYCAADSFEDP
TCTLVTSSGAFQYWGQGTLVTVSSEPKSCDKTHTCPPCPAPELLGGPSVFLF

Sequence Listing

PPKPKDTLMISRTPEVTCVVVDVSHEDPEVKFNWYVDGVEVHNAKTKPREEQ
YNSTYRVVSVLTVLHQDWLNGKEYKCKVSNKALPAPIEKTISKAKGQPREPQ
VYTLPPSRDELTKNQVSLTCLVKGFYPSDIAVEWESNGQPENNYKTTPPVLD
SDGSFFLYSKLTVDKSRWQQGNVFSCSVMHEALHNHYTQKSLSLSPGK

>SEQ ID NO: 50 Hu56V4-Fc
QVQLVESGGGLVQPGGSLRLSCAASGFTFSRRCMAWFPQAPGKGLERVAKLL
TTSGSTYLADSVKGRFTISRDNSKNTVYLQMNSLRAEDTAVYYCAADSFEDP
TCTLVTSSGAFQYWGQGTLVTVSSEPKSCDKTHTCPPCPAPELLGGPSVFLF
PPKPKDTLMISRTPEVTCVVVDVSHEDPEVKFNWYVDGVEVHNAKTKPREEQ
YNSTYRVVSVLTVLHQDWLNGKEYKCKVSNKALPAPIEKTISKAKGQPREPQ
VYTLPPSPDELTKNQVSLTCLVKGFYPSDIAVEWESNGQPENNYKTTPPVLD
SDGSFFLYSKLTVDKSRWQQGNVFSCSVMHEALHNHYTQKSLSLSPGK

>SEQ ID NO: 51 Hu56V5-Fc
QVQLVESGGGLVQPGGSLRLSCAASGKMSSRRCMAWFRQAPGKERERVAKLL
TTSGSTYLADSVKGRFTISRDNSKNTVYLQMNSLKAEDTAVYYCAADSFEDP
TCTLVTSSGAFQYWGQGTLVTVSSEPKSCDKTHTCPPCPAPELLGGPSVFLF
PPKPKDTLMISRTPEVTCVVVDVSHEDPEVKFNWYVDGVEVHNAKTKPREEQ
YNSTYRVVSVLTVLHQDWLNGKEYKCKVSNKALPAPIEKTISKAKGQPREPQ
VYTLPPSRDELTKNQVSLTCLVKGFYPSDIAVEWESNGQPENNYKTTPPVLD
SDGSFFLYSKITVDKSRWQQGNVFSCSVMHEALHNHYTQKSLSLSPGK

>SEQ ID NO: 52 Human PDL1-Fc
TVTVPKDLYVVEYGSNMTIECKFPVEKQLDLAALIVYWEMEDKNIIQFVHGE
EDLKVQHSSYRQRARLLKDQLSLGNAALQITDVKIQDAGVYRQMISYGGADY
KRITVKVNAPYNKINQRILVVDPVTSEHELTCQAEGYPKAEVIWTSSDHQVL
SGKTTTTNSKREENLFNVTSTLRINTTTNEIFYCTFRRLDPEENHTAELVIP
ELPLAHPPNERTDDKTHTCPPCPAPELLGGPSVFLFPPKPKDTLMISRTPEV
TCVVVDVSHEDPEVKFNWYVDGYEVHNAKTKPREEQYNSTYRVVSVLTVLHQ
DWLNGKEYKCKVSNKALPAPIEKTISKAKGQPREPQVYTLPPSRDELTKNQV
SLTCLVKGFYPSDIAVEWESNGQPENNYKTTPPVLDSDGSFFLYSKLTVDKS
RWQQGNVFSCSVMHEALHNHYTQKSLSLSPGK >SEQ ID NO: 53 mice PDL1-Fc
FTITAPKDLYVVEYGSNVTMECRFPVERELDLLALVVYWEKEDEQVIQFVAG
EEDLKPQHSNFRGRASLPKDQLLKGNAALQITDVKLQDAGVYCCIISYGGAD
YKRITLKVNAPYRKINQRISVDPATSEHELICQAEGYPEAEVIWTNSDHQPV
SGKRSVTTSRTEGMLLNVTSSLRVNATANDVFYCTFWRSQPGQNHTAELIIP
ELPATHPPQNRTHDKTHTCPPCPAPELLGGPSVFLFPPKPKDTLMISRTPEV
TCVVVDVSHEDPEVKFNWYVDGVEVHNAKTKPREEQYNSTYRVVSVLTVLHQ
DWLNGKEYKCKVSNKALPAPIEKTISKAKGQPREPQVYTLPPSRDELTKNQV
SLTCLVKGFYPSDIAVEWESNGQPENNYKTTPPVLDSDGSFFLYSKLTVDKS
RWQQGNVFSCSVMHEALHNHYTQKSLSLSPGK >SEQ ID NO: 54 Human PD1-Fc
PGWFLDSPDRPWNPPTFSPALLVVTEGDNATFTCSFSNTSESFVLNWYRMSP
SNQTDKLAAFPEDRSQPGQDCRFRVTQLPNGRDFHMSVVRARRNDSGTYLCG
AISLAPKAQIKESLRAELRVTERRAEVPTAHPSPSPRPAGQFQDKTHTCPPC
PAPELLGGPSVFLFPPKPKDTLMISRTPEVTCVVVDVSHEDPEVKFNWYVDG
VEVHNAKTKPREEQYNSTYRVVSVLTVLHQDWLNGKEYKCKVSNKALPAPIE
KTISKAKGQPREPQVYTLPPSRDELTKNQVSLTCLVKGFYPSDIAVEWESNG
QPENNYKTTPPVLDSDGSFFLYSKLTVDKSRWQQGNVFSCSVMHEALHNHYT
QKSLSLSPGK >SEQ ID NO: 55 PDL1-Chis
TVTVPKDLYVVEYGSNMTIECKFPVEKQLDLAALIVYWEMEDKNIIQFVHGE
EDLKVQHSSYRQRARLLKDQLSLGNAALQITDVKLQDAGVYRCMISYGGADY
KRITVKVNAPYNKINQRILVVDPVTSEHELTCQAEGYPKAEVIWTSSDHQVL
SGKTTTTNSKREENLFNVTSTLRINTTTNEIFYCTFRRLDPEENHTAELVIP
ELPLAHPPNEETDGSHHHHHH >SEQ ID NO: 56 CD80-Chis
VIHVTKEVKEVATLSCGHNVSVEELAQTRIYWQKEKKMVLTMMSGDMNIWPE
YKNRTIFDITNNLSIVILALRPSDEGTYECVVLKYEKDAFKREHLAEVTLSV
KADFPTPSISDFEIPTSNIRRIICSTSGGFPEPHLSWLENGEELNAINTTVS
QDPETELYAVSSKLDFNMTTNHSFMCLIKYGHLRVNQTFNWNTTKQEHFPDN
DKTHTCPPCPAPELLGGPSVFLFPPKPKDTLMISRTPEVTCVVVDVSHEDPE
VYFNWYVDGVEVENAKTKPREEQYNSTYRVVSVLTVLHQDWLNGKEYKCKVS
NKALPAPIEKTISKAKGQPREPQVYTLPPSRDELTKNQVSLTCLVKGFYPSD
IAVEWESNGQPENNYKTTPPVLDSDGSFFLYSKLTVDKSRWQQGNVFSCSVM
HEALHNHYTQKSLSLSPGK >SEQ ID NO: 57 monkey PDL1
FTVTVPKDLYVVEYGSNMTIECKFPVEKQLDLTSLIVYWEMEDKNIIQFVHG
EEDLKVQHSNYKRAQLLKDQLSLGNAALRITDVKLQDAGVYRCMISYGGADY
KRITVKVNAPYNKINQRILVVDPVTSEHELTCQAEGYPKAEVIWTSSDHQVL SGKTTTTNSKREEKLLNVTSTLRINTTANEIFYCIFRRLDPEENHTAELVIP
ELPLALPPNERTHLVILGAIFLLLGVALTFIFYLRKGRMMDMKKSGIRVTNS
KKQRDTQLEET >SEQ ID NO: 58 10
aAGGTGCAGCTGCAGGAGTCTGGaGGAGGCTCGGTGCAGGCTGGAGGGTCTC
TGCGACTCTCCTGTGCACCCTCTGGAAACATTGTTAGTAGCTACTGTATGGG
CTGGTTCCGACAGGCTCCAGGGAAAGAGCGCGTGGGGGTCGCCGCTATTGAT
AGTGATGGTACCACAAAATACGCAGACTCCATGAAGGGCCGATTCACCATCT
CCAAAGACAACGCCAAGAACACTCTAGATCTCAAATGAACACCCTGAAAACC
TGAGGACACTGCCATGTACTACTGTGTGGCACGTTTGAACTGCCCCGGACCA
GTTGATTGGGTCCCGATGTTCCCTTACAGGGGCCAGGGGACCCAGGTCACCG
TCTCCTCA >SEQ ID NO:59 27
aAGGTGCAGCTGCAGGAGTCTGGAGGAGGCTCGGTGCAGGCTGGAGGGTCTC
TGAGACTCTCCTGTGCAGCCTCTGGAAACATCAGCAGTAGGCGATGTATGGC
CTGGTTCCGCCAGGCTCCAGGGAAGGAGCGCGAAAGAGTCGCGAACATTCTA
ACTACTACTGGTAACACATACTTGGCCGACTCCGTGAAGGGCCGATTCACCA
TCTCCCAAAACAACGCCAAGAGCACGGTGTATCTGCAAATGAACAGCCTGAA
ACCTGAGGACACTGCCATGTACTACTGTGCGGCAGATTCTTTCCATGATCCG
ACTTGTACGGTGGTACCTAGTTCGGGGGCCTTTCAGTACTGGGGCCAGGGGA
CCCAGGTCACCGTCTCCTCA >SEQ ID NO: 60 38
CAGGTGCAGCTGCAGGAGTCTGaAGGAGGCTCGGTGCAGGCTGGAGGGTCTC
TGAGACTCTCCTGTGCAGTATCTGGTTTCATCAGCAGTAGGCGATGTATGGG
CTGGTTCCGACAGGCTCCAGGGAACCAGCGCGTGGGGGTCGCGAACATTACT
GGTACTGGTAACACATACTTGGCCGACTCCGTGAAGGGCCGATTCACCATCT
CCCAAAACAACGCCAAGAGCACGGTGTATCTGCAAATGAACAGCCTGAAACC
TGAGGACACTGCCATGTACTACTGTGCGGCAGATTCTTTCCCGACTTGTACG
GTGGTAGCTAGTTCGGGGGCCTTTCAGTACTGGGGCCAGGGGACCCAGGTCA
CCGTCTCCCA >SEQ ID NO: 61 56
CAGGTGCAGCTGCAGGAGTCTGGGGGAGGCTTGGTGCAGCCTGGGGGGTCCC
TGAGACTCTCCTGTGCAGCCTCTGGAAAGATGTCCCGTAGGCGATGTATGGC
CTGGTTCCGCCAGGCTCCAGGGAAGGAGCGCGAAAGGGTCGCGAAGCTGCTT
ACTACTAGTGGTAGCACATACTTGGCCGACTCCGTGAAGGGCCGATTCACCA
TCTCCCAAAACAACGCCAAGAGCACGGTGTATCTGCAAATGAATAAGCCTGAA
ACCTGAGGACACTGCCATGTACTACTGTGCGGCAGATTCTTTCGAAGATCCT
ACTTGTACGCTAGTAACTAGTTCGGGGGCCTTTCAGTACTGGGGCCAGGGGA
CCCAGGTCACCGTCTCCTCA >SEQ ID NO: 62 69
CAGGTGCAGCTGCAGGAGTCTGGAGGAGGCTCGGTGaAGGCTGGAGGGTCTC
TGAGACTCTCCTGTGCAGTTCAACGAAACATCAGCAGTAGCTACTGTATGGC
CTGGTTCCGCCAGGCTCCAGGGAAGCAGCGCGAAAGAGTCGATAAGATTCTA
ACTACTCCAGGTAACACATACTTGGCCGACTCCGTGAAGGGCCGATTCACCA
TCTCCCAAAACAACGCCAAGAGCACGGTGTATCTGaAAATGAACAGCCTGAA
ACCTGAGGACACTGCCATGTACTACTGTGCGGCAGATTCTTTCCAAAAGCCG
ACTTGTACGGTGGTAGCTTCTTGGCCAGCCTTTCAGTACTGGGGCCAGGGGA
CCCAGGTCACCGTCTCCTCA >SEQ ID NO: 63 81
CAGGTGCAGCTGCAGGAGTCTGGGGGAGGCTCGGTGCAGGCTGGAGGGTCTC
TGAGACTCTCCTGTGCAGCCTCTGGAAACATCATTCGTGTGCGATGTATGGC
CTGGTTCCGCCAGGCTCCAGGGAAGGAGCGCGAAAGAGGCCCGAACATTCTA
ACTACTACTATTAGCACATACTTGGCCGACTCCGTGAAGGGCCGATTCACCA
TCTCCCAAAACAACGCCAAGAGCACGGTGTATCTGCAAATGAACAGCCTGAA
ACCTGAGGACACTGCCATGTACTACTGTGCGGCAGATTCTTTCGGTTATCCG
ACTTGCCCCGGACCAGCTAGTTCGGGGGCCTTTCAGTACTGGGGCCAGGGGA
CCCAGGTCACCGTCTCCTCA >SEQ ID NO: 64 87
CAGGTGCAGCTGCAGGAGTCTGGGGGAGGCTCGGTGCAGGCTGGAGGGTCTC
TGAAACTCTCCTGTGCAGCCTCTGGATACATCTTCAGTAGCTGCGGAATGGG
CTGGTACCGCCAGGCTCCAGGGAAGGAGCGCGAGTTGGTCTCAACTATTAGT
AGTGATGGTACCACAAGCTATGCAGACTCCGTGAAGGGCCGATTCACCATCT
CCCAAGACAATGCCAAGAACACGCTGTATCTGCAAATGAACAGCCTGAAAAC
TGAGGACACGGCCGTGTATTACTGTGTGGCAGATTGTCCACCCATACCGGAA
TTTACAAGTTGTAGTGGTGGTTACTGCTTGAGTGGCGACTACTGGGGCCAGG
GGACCCAGGTCACCGTCTCCTCA >SEQ ID NO: 65 94
CAGGTGCAGCTGCAGGAGTCTGGGGGAGGCTCGGTGCAGGCTGGAGGGTCTC
TGAGACTCTCCTGTGCAGCCTCTCTAAATATTTTTAGTAGCTACTGTATGGG

```
CTGGTTCCGCCAGGCTCCAGGGAAGCAGCGCGTGGGGGTCGCGACTATTGAT
AGTGATGGTACTACAAGATACGTAGACTCCGTGAAGaGCCGATTCACCATCT
CCAAAGACAACGCCAAGAACACTCTAGATCTCCAAATGAACAGCCTGAAACC
TGAGGACACTGCCATGTACTACTGTGCGGCACGTTTGAACTGCCCCGGGCCA
GTTGATTGGGTCCCGATGTTTCCTTACAGGGGCCAGGGGACCCAGGTCACCG
TCTCCTCA

>SEQ ID NO: 66
GTCCTGGCTGCTCTTCTACAAGGC

>SEQ ID NO: 67
GGTACGTGCTGTTGAACTGTTCC

>SEQ ID NO: 68
GATGTGCAGCTGCAGGAGTCTGGRGGAGG

>SEQ ID NO: 69
GGACTAGTGCGGCCGCTGGAGACGGTGACCTGGGT

>SEQ ID NO: 70 mutant Fc IgiGa-Fc-ml
EPKSSDKTHTCPPCPAPELLGGPSVFLFPPKPKDTLMISRTPEVTCVVVAVS
HEDPEVKFNWYVDGVEVHNAKTKPREEQYNSTYRVVSVLTVLHQDWLNGKEY
KCKVSNKALPAGIEKTISKAKGQPREPQVYTLPPSRDELTKNQVSLTCLVKG
FYPSDIAVEWESNGQPENNYKTTPPVLDSDGSFFLYSKLTVDKSRWQQGNVF
SCSVMHEALHNHYTQKSLSLSPGK >SEQ ID NO: 71 mutant Fc IgG1-Fc-m2
EPKSSDKTHTCPPCPAPELLGGPSVFLFPPKPKDTLMISRTPEVTCVVVDVS
HEDPEVKFNWYVDGVEVHNAKTKPREEQYASTYRVVSVLTVLHQDWLNGKEY
KCKVSNKALPAPIEKTISKAKGQPREPQVYTLPPSRDELTKNQVSLTCLVKG
FYPSDIAVEWESNGQPENNYKTTPPVLDSDGSFFLYSKLTVDKSPWQQGNVF
SCSVMHEALHNHYTQKSLSLSPGK >SEQ ID NO: 72 56-Fc-m2
QVQLQESGGGLVQPGGSLPLSCAASGKMSSRRCMAWFRQAPGKERERVAKLL
TTSGSTYLADSVKGRFTISQNNAKSTVYLQMNSLKPEDTAMYYCAADSFEDP
TCTLVTSSGAFQYWGQGTQVTVSSEPKSSDKTHTCPPCPAPELLGGPSVFLF
PPKPKDTLMISRTPEVTCVVVDVSHEDPEVKFNWYVDGVEVENAKTKPREEQ
YASTYRVVSVLTVLHQDWLNGKEYKCKVSNKALPAPIEKTISKAKGQPREPQ
VYTLPPSRDELTKNQVSLTCLVKGFYPSDIAVEWESNGQPENNYKTTPPVLD
SDGSFFLYSKLTVDKSRWQQGNVFSCSVMHEALHNHYTQKSLSLSPGK >SEQ ID NO: 73 Hu56V1-Fc-m2
QVQLVESGGGLVQPGGSLRLSCAASGKMSSRRCMAWFRQAPGKERERVAKLL
TTSGSTYLADSVKGRFTISRDNSKNTVYLQMNSLRAEDTAVYYCAADSFEDP
TCTLVTSSGAFQYWGQGTLVTVSSEPKSSDKTHTCPPCPAPELLGGPSVFLF
PPKPKDTLMISRTPEVTCVVVDVSHEDPEVKFNWYVDGVEVHNAKTKPREEQ
YASTYRVVSVLTVLHQDWLNGKEYKCKVSNKALPAPIEKTISKAKGQPPEPQ
VYTLPPSPDELTKNQVSLTCLVKGFYPSDIAVEWESNGQPENNYKTTPPVLD
SDGSFFLYSKLTVDKSRWQQGNVFSCSVMHEALHNHYTQKSLSLSPGK >SEQ ID NO: 74 Hu56V2-Fc-m2
QVQLVESGGGLVQPGGSLRLSCAASGFTFSRRCMAWFRQAPGKERERVAKLL
TTSGSTYLADSVKGRFTISRDNSKNTVYLQMNSLRAEDTAVYYCAADSFEDP
TCTLVTSSGAFQYWGQGTLVTVSSEPKSSDKTHTCPPCPAPELLGGPSVFLF
PPKPKDTLMISRTPEVTCVVVDVSHEDPEVKFNWYVDGVEVHNAKTKPREEQ
YASTYPVVSVLTVLHQDWLNGKEYKCKVSNKALPAPIEKTISKAEGQPREPQ
VYTLPPSRDELTKNQVSLTCLVKGFYPSDIAVEWESNGQPENNYKTTPPVLD
SDGSFFLYSKLTVDKSRWQQGNVFSCSVMHEALHNHYTQKSLSLSPGK >SEQ ID NO: 75 Hu56V3-Fc-m2
QVQLVESGGGLVQPGGSLRLSCAASGKMSSRRCMAWFRQAPGKGLERVAKLL
TTSGSTYLADSVHGRFTISRDNSKNTVYLQMNSLRAEDTAVYYCAADSFEDP
TCTLVTSSGAFQYWGQGTLVTVSSEPKSSDKTHTCPPCPAPELLGGPSVFLF
PPKPKDTLMISPTPEVTCVVVDVSHEDPEVKFNWYVDGVEVENAKTKPREEQ
YASTYRVVSVLTVLHQDWLNGKEYKCKVSNKALPAPIEKTISKAKGQPREPQ
VYTLPPSRDELTKNQVSLTCLVKGFYPSDIAVEWESNGQPENNYKTTPPVLD
SDGSFFLYSKLTVDKSPWQQGNVFSCSVMHEALHNHYTQKSLSLSPGK >SEQ ID NO: 76 Hu56V4-Fc-m2
QVQLVESGGGLVQPGGSLRLSCAASGFTFSRRCMAWFPQAPGKGLERVAKLL
TTSGSTYLADSVKGRFTISRDNSKNTVYLQMNSLRAEDTAVYYCAADSFEDP
TCTLVTSSGAFQYWGQGTLVTVSSEPKSSDKTHTCPPCPAPELLGGPSVFLF
PPKPKDTLMISRTPEVTCVVVDVSHEDPEVKFNTWVDGVEVHNAKTKPREEQ
YASTYRVVSVLTVLHQDWLNGKEYKCKVSNKALPAPIEKTISKAKGQPREPQ
VYTLPPSRDELTKNQVSLTCLVKGFYPSDIAVEWESNGQPENNYKTTPPVLD
SDGSFFLYSKLTVDKSRWQQGNVFSCSVMHEALHNHYTQKSLSLSPGK
```

>SEQ ID NO: 77 Hu56V5-Fc-m2
QVQLVESGGGLVQPGGSLRLSCAASGKMSSRRCMAWFRQAPGKERERVAKLL
TTSGSTYLADSVKGRFTISRDNSKNTVYLQMNSLKAEDTAVYYCAADSFEDP
TCTLVTSSGAFQYWGQGTLVTVSSEPKSSDKTHTCPPSPAPELLGGPSVFLF
PPKPKDTLMISRTPEVTCVVVDVSHEDPEVKFNWYVDGVEVHNAKTKPREEQ
YASTYRVVSVLTVLHQDWLNGKEYKCKVSNKALPAPIEKTISKAKGQPREPQ
VYTLPPSRDELTKNQVSLTCLVKGFYPSDIAVEWESNGQPENNYKTTPPVLD
SDGSFFLYSKLTVDKSRWQQGNVFSCSVMHEALHNHYTQKSLSLSPGK

>SEQ ID NO: 78 56-Fc-m1
QVQLQESGGGLVQPGGSLRLSCAASGKMSSRRCMAWFPQAPGKERERVAKLL
TTSGSTYLADSVKGRFTISQNNAKSTVYLQMNSLKPEDTAMYYCAADSFEDP
TCTLVTSSGAFQYWGQGTQVTVSSEPKSSDKTHTCPPCPAPELLGGPSVFLF
PPKPKDTLMISRTPEVTCVVVAVSHEDPEVKFNWYVDGVEVHNAKTKPREEQ
YNSTYRVVSVLTVLHQDWLNGKEYKCKVSNKALPAGIEKTISKAKGQPREPQ
VYTLPPSPDELTKNQVSLTCLVKGFYPSDIAVEWESNGQPENNYKTTPPVLD
SDGSFFLYSKLTVDKSRWQQGNVFSCSVMHEALHNHYTQKSLSLSPGK

>SEQ ID NO: 79 Hu56V1-Fc-m1
QVQLVESGGGLVQPGGSLRLSCAASGKMSSRRCMAWFRQAPGKERERVAKLL
TTSGSTYLADSVKGRFTISRDNSKNTVYLQMNSLRAEDTAVYYCAADSFEDP
TCTLVTSSGAFQYWGQGTLVTVSSEPKSSDKTHTCPPCPAPELLGGPSVFLF
PPKPKDTLMISRTPEVTCVVVAVSHEDPEVKFNWYVDGVEVHNAKTKPREEQ
YNSTYRVVSVLTVLHQDWLNGKEYKCKVSNKALPAGIEKTISKAKGQPREPQ
VYTLPPSRDELTKNQVSLTCLVKGFYPSDIAVEWESNGQPENNYKTTPPVLD
SDGSFFLYSKLTVDKSPWQQGNVFSCSVMHEALHNHYTQKSLSLSPGK

>SEQ ID NO: 80 Hu56V2-Fc-m1
QVQLVESGGGLVQPGGSLRLSCAASGFTFSRRCMAWFRQAPGKERERVAKIL
TTSGSTYLADSVKGRFTISRDNSKNTVYLQMNSLRAEDTAVYYCAADSFEDP
TCTLVTSSGAFQYWGQGTLVTVSSEPKSSDKTHTCPPCPAPELLGGPSVFLF
PPKPKDTLMISRTPEVTCVVVAVSHEDPEVKFNWYVDGVEVHNAKTKPREEQ
YNSTYRVVSVLTVLHQDWLNGKEYKCKVSNKALPAGIEFTISKAKGQPREPQ
VYTLPPSRDELTKNQVSLTCLVKGEYPSDIAVEWESNGQPENNYKTTPPVLD
SDGSFFLYSKLTVDKSRWQQGNVFSCSVMEHALHNHYTQKSLSLSPGK

>SEQ ID NO: 81 Hu56V3-Fc-m1
QVQLVESGGGLVQPGGSLPLSCAASGKMSSRPCMAWFRQAPGKGLERVAKLL
TTSGSTYLADSVKGRFTISRDNSKNTVYLQMNSLPAEDTAVYYCAADSFEDP
TCTLVTSSGAFQYWGQGTLVTVSSEPKSSDKTHTCPPCPAPELLGGPSVFLF
PPKPKDTLMISRTPEVTCVVVAVSHEDPEVKFNWYVDGVEVHNAKTKPREEQ
YNSTYRVVSVLTVLHNWLNGKEYKCKVSNKALPAPGIEKTISKAKGQPREPQ
VYTLPPSRDELTKNQVSLTCLVKGFYPSDIAVEWESNGQPENNYKTTPPVLD
SDGSFFLYSKLTVDKSRWQQGNVFSCSVMHEALHNHYTQKSLSLSPGK

>SEQ ID NO: 82 Hu56V4-Fc-m1
QVQLVESGGGLVQPGGSLRLSCAASGFTFSRRCMAWFPQAPGKGLERVAKLL
TTSGSTYLADSVKGRFTISRDNSKNTVYLQMNSLRAEDTAVYYCAADSFEDP
TCTLVTSSGAFQYNGQGTLVTVSSEPKSSDKTHTCPPCPAPELLGGPSVFLF
PPKPKDTLMISRTPEVTCVVVAVSHEDPEVKFNWYVDGVEVHNAKTKPREEQ
YNSTYRVVSVLTVLHQDWLNGKEYKCKVSNKALPAGIEKTISKAKGQPREPQ
VYTLPPSPDELTKNQVSLTCLVKGFYPSDIAVEWESNGQPENNYKTTPPVLD
SDGSFFLYSKLTVDKSRWQQGNVFSCSVMHEALHNHYTQKSLSLSPGK

>SEQ ID NO: 83 Hu56V5-Fc-m1
QVQLVESGGGLVQPGGSLRLSCAASGKMSSRRCMAWFRQAPGKERERVAKLL
TTSGSTYLADSVKGRFTISRDNSKNTVYLQMNSLRAEDTAVYYCAADSFEDP
TCTLVTSSGAFQYWGQGTLVTVSSEPKSSDKTHTCPPCPAPELLGGPSVFLF
PPKTKDTLMISRTPEVTCVVVAVSHEDPEVKFNWYVDGVEVHNAKTKPREEQ
YNSTYRVVSVLTVLHQDWLNGKEYHCKVSNKALPAGIEKTISKAKGQPREPQ
VYTLPPSRDELTKNQVSLTCLVKGFYPSDIAVEWESNGQPENNYKTTPPVLD
SDGSFFLYSKLTVDKSPWQQGNVFSCSVMHEALHNHYTQKSLSLSPGK

>SEQ ID NO: 84 human PDL1-muFc
FTVTVPKDLYVVEYGSNMTIECKFPVEKQLDLAALIVYWEMEDKNIIQFVHG
EEDLKVQHSSYRQRARLLKDQLSLGNAALQITDVKLQDAGVYRCMISYGGAD
YKRITVKVNAPYNKINQRILVVDPVTSEHELTCQAEGYPKAEVIWTSSDHQV
LSGKTTTTNSKREEKLFNVTSTLRINTTTNEIFYCTFRRLDPEENHTAELVI
PELPLAHPPNERTDIEGRMDPKSSDKTHTCPPCPAPEVSSVFIFPPKPKDVL
TITLTPKVTCVVVDISKDDPEVQFSWFVDDVEVHTAQTQPREEQFNSTFRSV
SELPIMHQDWLNGKEFKCRVNSAAFPAPIEKTISKTKGRPKAPQVYTIPPPK
EQMAKDKVSLTCMITDFFPEDITVEWQWNGQPAENYKNTQPIMNTNGSYFVY
SKLNVQKSNWEAGNTFTCSVLHEGLHNHHTEKSLSHSPGK

| Sequence Listing |
|---|
| >SEQ ID NO: 85 Human PD1-muFc<br>PGWFLDSPDRPWNPPTFSPALLVVTEGDNATFTCSFSNTSESFVLNWYRMSP<br>SNQTDKLAAFPEDRSQPGQDCRFRVTQLPNGRDFHMSVVRARPNDSGTYLCG<br>AISLAPKAQIKESLRAELRVTERRAEVPTAHPSPSPRPAGQFQIEGPMDPKS<br>SDKTHTCPPCPAPEVSSVFIFPPKPKDVLTITLTPKVTCVVVDISKDDPEVQ<br>FSWFVDDVEVHTAQTQPREEQFNSTFRSVSELPIMHQDWLNGKEFKCRVNSA<br>AFPAPIEKTISKTKGRPKAPQVYTIPPPKEQMAKDKVSLTCMITDFFPEDIT<br>VEWQWNGQPAENYKNTQPIMNTNGSYFVYSKLNVQKSNWEAGNTFTCSVLHE<br>GLHNHHTEKSLSHSPGK |

What is claimed is:

1. A programmed death ligand 1 (PDL1) antibody, which specifically binds to PDL1 and comprises at least one immunoglobulin single variable domain, said immunoglobulin single variable domain comprises CDR1, CDR2 and CDR3 selected from the group consisting of:
   (1) CDR1 set forth in SEQ ID NO:1, CDR2 set forth in SEQ ID NO:2, CDR3 set forth in SEQ ID NO:3;
   (2) CDR1 set forth in SEQ ID NO:4, CDR2 set forth in SEQ ID NO:5, CDR3 set forth in SEQ ID NO:6;
   (3) CDR1 set forth in SEQ ID NO:7, CDR2 set forth in SEQ ID NO:8, CDR3 set forth in SEQ ID NO:9;
   (4) CDR1 set forth in SEQ ID NO:10, CDR2 set forth in SEQ ID NO:11, CDR3 set forth in SEQ ID NO:12;
   (5) CDR1 set forth in SEQ ID NO:13, CDR2 set forth in SEQ ID NO:14, CDR3 set forth in SEQ ID NO:15;
   (6) CDR1 set forth in SEQ ID NO:16, CDR2 set forth in SEQ ID NO:17, CDR3 set forth in SEQ ID NO:18;
   (7) CDR1 set forth in SEQ ID NO:19, CDR2 set forth in SEQ ID NO:20, CDR3 set forth in SEQ ID NO:21; and
   (8) CDR1 set forth in SEQ ID NO:22, CDR2 set forth in SEQ ID NO:23, CDR3 set forth in SEQ ID NO:24,
   wherein said immunoglobulin single variable domain is a VHH.

2. The PDL1 antibody of claim 1, wherein said VHH comprises an amino acid sequence having at least 80% sequence identity to any one of SEQ ID NOs:25-32, wherein there is no variation in CDRs of (1)-(8).

3. The PDL1 antibody of claim 1, wherein said VHH is humanized and comprises an amino acid sequence of any one of SEQ ID NOs:33-37.

4. The PDL1 antibody of claim 1, which has at least one of the following features:
   (a) binding to human PD-PDL1 with a KD of between $1\times10^{-7}$ M and $1\times10^{-11}$ M;
   (b) blocking the interaction between PDL1 and PD-1; and
   (c) enhancing activation of PBMCs and/or T cells.

5. The PDL1 antibody of claim 1, wherein said VHH comprises an amino acid sequence of any one of SEQ ID NOs:25-32.

6. The PDL1 antibody of claim 1, which further comprises an immunoglobulin Fc region.

7. The PDL1 antibody of claim 6, wherein the immunoglobulin Fc region is an Fc region of human immunoglobulin.

8. The PDL1 antibody of claim 7, wherein the amino acid sequence of the immunoglobulin Fc region is selected from SEQ ID NOs:38, 70 and 71.

9. The PDL1 antibody of claim 8, which comprises an amino acid sequence selected from SEQ ID NOs:39-51 and 72-83.

10. An immunoconjugate, which comprises the PDL1 antibody of claim 1 that is conjugated with a therapeutic moiety.

11. The immunoconjugate of claim 10, wherein said therapeutic moiety comprises a cytotoxin, a biologically active protein or a radioactive isotope.

12. A pharmaceutical composition comprising the PDL1 antibody of claim 1, and a pharmaceutically acceptable carrier.

13. A pharmaceutical composition comprising the immunoconjugate of claim 10, and a pharmaceutically acceptable carrier.

14. A PDL1 antibody, which is obtained by affinity maturation of the PDL1 antibody of claim 1.

15. A nucleic acid molecule encoding the PDL1 antibody of claim 1.

16. An expression vector, which comprises the nucleic acid molecule of claim 15 operably linked to an expression regulation element.

17. A host cell which comprises the nucleic acid molecule of claim 15 and is capable of expressing said PDL1 antibody.

18. A host cell which is transformed with the expression vector of claim 16 and is capable of expressing said PDL1 antibody.

19. A method for producing a PDL1 antibody, which comprises:
   a) culturing the host cell of claim 17 under conditions that allow expression of the PDL1 antibody;
   b) recovering the PDL1 antibody expressed by the host cell from the culture of step a); and
   c) optionally further purifying and/or modifying the PDL1 antibody obtained from step b).

20. A method for detecting the presence of PDL1 and/or the expression level of PDL1 in a biological sample, comprising:
   a) contacting the PDL1 antibody of claim 1 with the biological sample and a control sample under conditions allowing formation of a complex between the PDL1 antibody of claim 1 and PDL1.
   b) detecting the formation of the complex,
   wherein the difference of the complex formation between the biological sample and the control sample indicates the presence of PDL1 and/or the expression level of PDL1 in the sample.

* * * * *